(12) United States Patent
Pestka

(10) Patent No.: US 7,666,995 B2
(45) Date of Patent: Feb. 23, 2010

(54) INTERFERONS, USES AND COMPOSITIONS RELATED THERETO

(75) Inventor: Sidney Pestka, North Caldwell, NJ (US)

(73) Assignee: Pestka Biomedical Laboratories, Piscataway, NJ (US)

( * ) Notice: Subject to any disclaimer, the term of this patent is extended or adjusted under 35 U.S.C. 154(b) by 0 days.

(21) Appl. No.: 10/415,969

(22) PCT Filed: Nov. 5, 2001

(86) PCT No.: PCT/US01/47226

§ 371 (c)(1),
(2), (4) Date: May 2, 2003

(87) PCT Pub. No.: WO02/36627

PCT Pub. Date: May 10, 2002

(65) Prior Publication Data

US 2004/0105841 A1    Jun. 3, 2004

Related U.S. Application Data

(60) Provisional application No. 60/245,754, filed on Nov. 3, 2000, provisional application No. 60/246,234, filed on Nov. 3, 2000.

(51) Int. Cl.
*C07K 14/52* (2006.01)
*C12N 15/21* (2006.01)
*A61K 38/21* (2006.01)

(52) U.S. Cl. .................. 530/351; 435/69.51; 424/85.4

(58) Field of Classification Search ............... None
See application file for complete search history.

(56) References Cited

U.S. PATENT DOCUMENTS

| | | | |
|---|---|---|---|
| 5,089,400 A | | 2/1992 | Meyer |
| 5,780,021 A | * | 7/1998 | Sobel ................... 424/85.4 |
| 6,299,877 B1 | * | 10/2001 | Chen et al. ............. 424/158.1 |
| 6,350,443 B1 | | 2/2002 | Kajimoto et al. |
| 6,703,225 B1 | | 3/2004 | Kojima et al. |

FOREIGN PATENT DOCUMENTS

| | | |
|---|---|---|
| EP | 0076489 | 4/1983 |
| EP | 322 870 | 7/1989 |
| EP | 414 355 | 2/1991 |
| EP | 0439997 | 8/1991 |
| EP | 875 251 | 10/1996 |
| JP | 3-139276 | 6/1990 |
| JP | 2-195884 | 8/1990 |
| JP | 130693 | 5/1999 |
| JP | 151692 | 6/2001 |
| WO | WO-84/01153 | 3/1984 |
| WO | WO 99/61618 | 12/1999 |
| WO | WO00/42186 | 7/2000 |
| WO | WO 01/40313 | 6/2001 |
| WO | WO-2005/023290 | 3/2005 |

OTHER PUBLICATIONS

Ueda et al., J Vet Med Sci. 1993, vol. 55(2): pp. 251-258, esp. 257: Figure 10.*
Ngo et al., 1994, The Protein Folding Problem and Tertiary Structure Prediction, pp. 492-495.*
Wells, Aditivity of Mutational Effects in Proteins, 1990, Biochemistry, vol. 26, No. 37, pp. 8509-8517.*
Ueda, et al., "Homogeneous Production of Feline Interferon in Silkworm by Replacing Single Amino Acid Code in Signal Peptide in Recombinant Baculovirus and Characterization of the Product," *J. Vet. Med. Sci.* 55(2): 251-258, (1993).
Pestka, "The Human Interferon α Species and Receptors," *Biopolymers (Pept Sci)* 55: 254-287 (2000).
Office Action dated Oct. 28, 1997, Amendment Under 37 C.F.R. 1.115, including Declaration of Sidney Pestka Pursuant to 37 C.F.R. § 1.132 filed on Apr. 28, 1998, in connection with corresponding U.S. Appl. No. 08/489,071 (now U.S. Patent No. 6,300,474).
Database UniProt (on-line) Uniprot: P32881 "Interferon alpha-8 precursor" Jul. 21, 1986.

* cited by examiner

*Primary Examiner*—Christine J Saoud
*Assistant Examiner*—Jegatheesan Seharaseyon
(74) *Attorney, Agent, or Firm*—Ropes & Gray LLP; Barbara A. Ruskin; Teresa A. Chen

(57) ABSTRACT

The present disclosure provides isolated Interferonα nucleic acids and polypeptides. The disclosure also provides antibodies which specifically recognize the subject Interferonα polypeptides, expression vectors containing the subject nucleic acids, and host cells expressing the subject polypeptides. In addition, methods of treatment using Interferonα are provided.

6 Claims, No Drawings

US 7,666,995 B2

INTERFERONS, USES AND COMPOSITIONS RELATED THERETO

This application is a national stage filing under 35 U.S.C. 371 of International Application No. PCT/US01/47226, filed Nov. 5, 2001, which claims priority from U.S. Provisional Patent Application No. 60/245,754, filed Nov. 3, 2000, and U.S. Provisional Patent Application No. 60/246,234, filed Nov. 3, 2000, the specification of each of which are incorporated by reference herein. International Application No. PCT/US01/47226 was published under PCT Article 21(2) in English.

BACKGROUND OF THE INVENTION

Interferons (IFNs) are a well known family of cytokines secreted by a large variety of eukaryotic cells upon exposure to various stimuli. The interferons have been classified by their chemical and biological characteristics into four groups: IFN-α. (leukocytes), IFN-β (fibroblasts), IFN-γ (lymphocytes), and IFN-ω (leukocytes). IFN-α and β are known as Type I interferons: IFN-γ is known as a Type-II or immune interferon. The IFNs exhibit anti-viral, immunoregulatory, and antiproliferative activity. The clinical potential of interferons has been recognized.

Human leulcocyte interferon was first discovered and prepared in the form of very crude fractions by Isaacs and Lindenmann. Efforts to purify and characterize the material have led to the preparation of relatively homogeneous leukocyte interferons derived from normal or leukemic (chronic myelogenous leukemia or "CML") donor leukocytes. These interferons are a family of proteins characterized by a potent ability to confer a virus-resistant state in their target cells. In addition, interferon can inhibit cell proliferation, modulate immune responses and alter expression of proteins. These properties have prompted the clinical use of leukocyte interferon as a therapeutic agent for the treatment of viral infections and malignancies.

During the past several decades a large number of human and animal interferons have been produced, identified, purified and cloned. Several of the interferon preparations have been prepared for clinical trial in both crude form, for some of the original interferon preparations, as well as in purified form. Several individual recombinant interferon-α species have been cloned and expressed. The proteins have then been purified by various procedures and formulated for clinical use in a variety of formulations. Most of the interferons in clinical use that have been approved by various regulatory agencies throughout the world are mixtures or individual species of human α interferon (Hu-IFN-α). In some countries Hu-IFN-β and γ have also been approved for clinical trial and in some cases approved for therapeutic use. The major thesis underlying clinical use of these interferons was that they were natural molecules produced by normal individuals. Indeed, the specific thesis was that all the interferons prepared for clinical use, be they natural-or recombinant-generated products, represented interferons that were produced naturally by normal people. This is true for a large number of interferons as well as specific growth factors, lymphokines, cytokines, hormones, clotting factors and other proteins that have been produced.

SUMMARY OF THE INVENTION

The present invention provides isolated nucleic acid molecules comprising a polynucleotide encoding at least a portion of an Interferon polypeptide including an amino acid sequence shown in at least one of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86 or a fragment thereof. Thus, one aspect of the invention provides an isolated polynucleotide comprising a nucleotide sequence selected from the group consisting of: (a) a nucleotide sequence encoding an Interferon polypeptide including an amino acid sequence in at least one of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84 or 86; (b) a nucleotide sequence encoding a biologically active fragment of a polypeptide shown in at least one of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84 or 86; and (c) a nucleotide sequence complementary to at least one of any of the nucleotide sequences in (a) or (b) above.

Further embodiments of the invention include isolated nucleic acid molecules that comprise a polynucleotide having a nucleotide sequence at least 90% identical, and more preferably at least 95%, 96%, 97%, 98% or 99% identical, to any of the nucleotide sequences in (a), (b) or (c), above, or a polynucleotide which hybridizes under stringent hybridization conditions to a polynucleotide in (a), (b) or (c), above, and preferably to a polynucleotide shown in at least one of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83 or 85. By "stringent hybridization conditions" is intended overnight incubation at 42° C. in a solution comprising: 50% formamide, 5×SSC (150 mM NaCl, 15 mM trisodium citrate), 50 mM sodium phosphate (pH 7.6), 5× Denhardt's solution, 10% dextran sulfate, and 20 mu g/ml denatured, sheared salmon sperm DNA, followed by washing the filters in 0.1×SSC at about 65° C.

More generally, by a fragment of an isolated nucleic acid molecule having the nucleotide sequence shown in at least one of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83 or 85, is intended fragments at least about 15 nucleotides, and more preferably at least about 20 nucleotides, still more preferably at least about 30 nucleotides, and even more preferably, at least about 40 nucleotides in length which are useful as diagnostic probes and primers as discussed herein. Of course, larger fragments 50-300 nucleotides in length are also useful according to the present invention as are fragments corresponding to most, if not all, of at least one of the nucleotide sequences shown in at least one of SEQ D NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83 or 85. By a fragment at least 20 nucleotides in length, for example, is intended fragments which include 20 or more contiguous bases from at least one of the nucleotide sequences as shown in at least one of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83 or 85.

By a polynucleotide which hybridizes to a "portion" of a polynucleotide is intended a polynucleotide (either DNA or RNA) hybridizing to at least about 15 nucleotides, and more preferably at least about 20 nucleotides, still more preferably at least about 30 nucleotides, and even more preferably about 30-70 (e.g., 50) nucleotides of the reference polynucleotide. These are useful as diagnostic probes and primers as discussed above and in more detail below.

In another aspect, the present invention provides isolated nucleic acid molecules comprising a polynucleotide encoding at least a portion of a feline Interferon polypeptide including an amino acid sequence shown in at least one of SEQ ID NO: 2, 4, 6, 8, 10, 12, 14, 16, 18, 20, 22, 24, 26 or a fragment thereof. Thus, one aspect of the invention provides an isolated polynucleotide comprising a nucleotide sequence selected from the group consisting of: (a) a nucleotide sequence encoding a feline Interferon polypeptide including an amino acid sequence in at least one of SEQ ID NO: 2, 4, 6, 8, 10, 12, 14, 16, 18, 20, 22, 24 or 26; (b) a nucleotide sequence encoding a biologically active fragment of a polypeptide shown in at least one of SEQ ID NO: 2, 4, 6, 8, 10, 12, 14, 16, 18, 20, 22, 24 or 26; and (c) a nucleotide sequence complementary to at least one of any of the nucleotide sequences in (a) or (b) above.

Further embodiments of the invention include isolated nucleic acid molecules that comprise a polynucleotide having a nucleotide sequence at least 90% identical, and more preferably at least 95%, 96%, 97%, 98% or 99% identical, to any of the nucleotide sequences in (a), (b) or (c), above, or a polynucleotide which hybridizes under stringent hybridization conditions to a polynucleotide in (a), (b) or (c), above, and preferably to a polynucleotide shown in at least one of SEQ ID NO: 1, 3, 5, 7, 9, 11, 13, 15, 17, 19, 21, 23 or 25. By "stringent hybridization conditions" is intended overnight incubation at 42° C. in a solution comprising: 50% formamide, 5×SSC (150 mM NaCl, 15 mM trisodium citrate), 50 mM sodium phosphate (pH 7.6), 5× Denhardt's solution, 10% dextran sulfate, and 20 mu g/ml denatured, sheared salmon sperm DNA, followed by washing the filters in 0.1× SSC at about 65° C.

More generally, by a fragment of an isolated nucleic acid molecule having the nucleotide sequence shown in at least one of SEQ ID NO: 1, 3, 5, 7, 9, 11, 13, 15, 17, 19, 21, 23 or 25, is intended fragments at least about 15 nucleotides, and more preferably at least about 20 nucleotides, still more preferably at least about 30 nucleotides, and even more preferably, at least about 40 nucleotides in length which are useful as diagnostic probes and primers as discussed herein. Of course, larger fragments 50-300 nucleotides in length are also useful according to the present invention as are fragments corresponding to most, if not all, of at least one of the nucleotide sequences shown in at least one of SEQ ID NO: 1, 3, 5, 7, 9, 11, 13, 15, 17, 19, 21, 23 or 25. By a fragment at least 20 nucleotides in length, for example, is intended fragments which include 20 or more contiguous bases from at least one of the nucleotide sequences as shown in at least one of SEQ ID NO: 1, 3, 5, 7, 9, 11, 13, 15, 17, 19, 21, 23 or 25.

By a polynucleotide which hybridizes to a "portion" of a polynucleotide is intended a polynucleotide (either DNA or RNA) hybridizing to at least about 15 nucleotides, and more preferably at least about 20 nucleotides, still more preferably at least about 30 nucleotides, and even more preferably about 30-70 (e.g., 50) nucleotides of the reference polynucleotide. These are useful as diagnostic probes and primers as discussed above and in more detail below.

In another aspect, the present invention further provides isolated nucleic acid molecules comprising a polynucleotide encoding at least a portion of a Rhesus Interferon polypeptide including an amino acid sequence shown in at least one of SEQ ID NO: 28, 30, 32, 34, 36 or a fragment thereof. Thus, one aspect of the invention provides an isolated polynucleotide comprising a nucleotide sequence selected from the group consisting of: (a) a nucleotide sequence encoding a Rhesus Interferon polypeptide including an amino acid sequence in at least one of SEQ ID NO: 28, 30, 32, 34 or 36; (b) a nucleotide sequence encoding a biologically active fragment of a polypeptide shown in at least one of SEQ ID NO: 28, 30, 32, 34 or 36; and (c) a nucleotide sequence complementary to any of the nucleotide sequences in (a) or (b) above.

Further embodiments of the invention include isolated nucleic acid molecules that comprise a polynucleotide having a nucleotide sequence at least 90% identical, and more preferably at least 95%, 96%, 97%, 98% or 99% identical, to any of the nucleotide sequences in (a), (b) or (c), above, or a polynucleotide which hybridizes under stringent hybridization conditions to a polynucleotide in (a), (b) or (c), above, and preferably to a polynucleotide shown in at least one of SEQ ID NO: 27, 29, 31, 33 or 35. By "stringent hybridization conditions" is intended overnight incubation at 42° C. in a solution comprising: 50% formamide, 5×SSC (150 mM NaCl, 15 mM trisodium citrate), 50 mM sodium phosphate (pH 7.6), 5× Denhardt's solution, 10% dextran sulfate, and 20 mu g/ml denatured, sheared salmon sperm DNA, followed by washing the filters in 0.1×SSC at about 65° C.

More generally, by a fragment of an isolated nucleic acid molecule having the nucleotide sequence shown in at least one of SEQ ID NO: 27, 29, 31, 33 or 35, is intended fragments at least about 15 nucleotides, and more preferably at least about 20 nucleotides, still more preferably at least about 30 nucleotides, and even more preferably, at least about 40 nucleotides in length which are useful as diagnostic probes and primers as discussed herein. Of course, larger fragments 50-300 nucleotides in length are also useful according to the present invention as are fragments corresponding to most, if not all, of the nucleotide sequence shown in at least one of SEQ ID NO: 27, 29, 31, 33 or 35. By a fragment at least 20 nucleotides in length, for example, is intended fragments which include 20 or more contiguous bases from the nucleotide sequence as shown in at least one of SEQ ID NO: 27, 29, 31, 33 or 35.

By a polynucleotide which hybridizes to a "portion" of a polynucleotide is intended a polynucleotide (either DNA or RNA) hybridizing to at least about 15 nucleotides, and more preferably at least about 20 nucleotides, still more preferably at least about 30 nucleotides, and even more preferably about 30-70 (e.g., 50) nucleotides of the reference polynucleotide. These are useful as diagnostic probes and primers as discussed above and in more detail below.

In another aspect, the present invention provides isolated nucleic acid molecules comprising a polynucleotide encoding at least a portion of a human Interferon polypeptide including an amino acid sequence shown in at least one of SEQ ID NO: 38, 40, 42, 44, 46, 48, 50, 52, 54, 56, 58, 60, 62, 64, 66, 68, 70, 72, 74, 76, 78, 80, 82, 84, 86 or a fragment thereof. Thus, one aspect of the invention provides an isolated polynucleotide comprising a nucleotide sequence selected from the group consisting of: (a) a nucleotide sequence encoding a human Interferon polypeptide including an amino acid sequence in at least one of SEQ ID NO: 38, 40, 42, 44, 46, 48, 50, 52, 54, 56, 58, 60, 62, 64, 66, 68, 70, 72, 74, 76, 78, 80, 82, 84 or 86; (b) a nucleotide sequence encoding a biologically active fragment of a polypeptide shown in at least one of SEQ ID NO: 38, 40, 42, 44, 46, 48, 50, 52, 54, 56, 58, 60, 62, 64, 66, 68, 70, 72, 74, 76, 78, 80, 82, 84 or 86; and (c) a nucleotide sequence complementary to any of the nucleotide sequences in (a) or (b) above.

Further embodiments of the invention include isolated nucleic acid molecules that comprise a polynucleotide having a nucleotide sequence at least 90% identical, and more preferably at least 95%, 96%, 97%, 98% or 99% identical, to any of the nucleotide sequences in (a), (b) or (c), above, or a polynucleotide which hybridizes under stringent hybridization conditions to a polynucleotide in (a), (b) or (c), above, and preferably to a polynucleotide shown in at least one of SEQ ID NO: 37, 39, 41, 43, 45, 47, 49, 51, 53, 55, 57, 59, 61, 63, 65, 67, 69, 71, 73, 75, 77, 79, 81, 83 or 85. By "stringent hybridization conditions" is intended overnight incubation at 42° C. in a solution comprising: 50% formamide, 5×SSC (150 mM NaCl, 15 mM trisodium citrate), 50 mM sodium phosphate (pH 7.6), 5× Denhardt's solution, 10% dextran sulfate, and 20 mu g/ml denatured, sheared salnon sperm DNA, followed by washing the filters in 0.1×SSC at about 65° C.

More generally, by a fragment of an isolated nucleic acid molecule having the nucleotide sequence shown in at least one of SEQ ID NO: 37, 39, 41, 43, 45; 47, 49, 51, 53, 55, 57, 59, 61, 63, 65, 67, 69, 71, 73, 75, 77, 79, 81, 83 or 85, is intended fragments at least about 15 nucleotides, and more preferably at least about 20 nucleotides, still more preferably at least about 30 nucleotides, and even more preferably, at least about 40 nucleotides in length which are useful as diagnostic probes and primers as discussed herein. Of course, larger fragments 50-300 nucleotides in length are also useful according to the present invention as are fragments corresponding to most, if not all, of the nucleotide sequence shown in at least one of SEQ ID NO: 37, 39, 41, 43, 45, 47, 49, 51, 53, 55, 57, 59, 61, 63, 65, 67, 69, 71, 73, 75, 77, 79, 81, 83 or 85. By a fragment at least 20 nucleotides in length, for example, is intended fragments which include 20 or more contiguous bases from the nucleotide sequence as shown in at least one of SEQ ID NO: 37, 39, 41, 43, 45, 47, 49, 51, 53, 55, 57, 59, 61, 63, 65, 67, 69, 71, 73, 75, 77, 79, 81, 83 or 85.

By a polynucleotide which hybridizes to a "portion" of a polynucleotide is intended a polynucleotide (either DNA or RNA) hybridizing to at least about 15 nucleotides, and more preferably at least about 20 nucleotides, still more preferably at least about 30 nucleotides, and even more preferably about 30-70 (e.g., 50) nucleotides of the reference polynucleotide. These are useful as diagnostic probes and primers as discussed above and in more detail below.

In another aspect, any of the nucleic acid molecules of the present invention which encode Interferon polypeptides may include, but are not limited to, those encoding the amino acid sequence of the complete polypeptide, by itself; and the coding sequence for the complete polypeptide and additional sequences, such as those encoding an added secretory leader sequence, such as a pre-, or pro- or prepro-protein sequence.

Also encoded by nucleic acids of the invention are the above protein sequences together with additional, non-coding sequences, including, for example, but not limited to introns and non-coding 5' and 3' sequences, such as the transcribed, non-translated sequences that play a role in transcription, mRNA processing, including splicing and polyadenylation signals, for example-ribosome binding and stability of mRNA; and an additional coding sequence which codes for additional amino acids, such as those which provide additional functionalities.

Thus, the sequence encoding the polypeptide may be fused to a marker sequence, such as a sequence encoding a peptide which facilitates purification of the fused polypeptide. In certain preferred embodiments of this aspect of the invention, the marker amino acid sequence is a hexa-histidine peptide, such as the tag provided in a pQE vector (QIAGEN, Inc., 9259 Eton Avenue, Chatsworth, Calif. 91311), among others, many of which are commercially available. For instance, hexa-histidine as described by Gentz et al. provides for convenient purification of the fusion protein (Gentz et al. (1989) Proc. Natl. Acad. Sci. USA 86: 821-824). The "HA" tag is another peptide useful for purification which corresponds to an epitope derived from the influenza hemagglutinin protein (Wilson et al. (1984) Cell 37: 767). As discussed below, other such fusion proteins include an Interferon fused to Fc at the N- or C-terminus.

The present invention also relates to recombinant vectors, which include the isolated nucleic acid molecules of the present invention, and to host cells containing the recombinant vectors, as well as to methods of making such vectors and host cells and for using them for production of Interferon polypeptides or peptides by 15 recombinant techniques.

In another aspect, the invention further provides an isolated Interferon polypeptide comprising an amino acid sequence selected from: (a) the amino acid sequence of an Interferon polypeptide including an acid sequence shown in at least one of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84 or 86; and (b) the amino acid sequence of a biologically active fragment of a polypeptide shown in at least one of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84 or 86. The polypeptides of the present invention also include polypeptides having an amino acid sequence at least 80% identical, more preferably at least 90% identical, and still more preferably 95%, 96%, 97%, 98% or 99% identical to those described in (a) or (b) above, as well as polypeptides having an amino acid sequence with at least 90% similarity, and more preferably at least 95% similarity, to those above. Polynucleotides encoding such polypeptides are also provided.

An additional embodiment of this aspect of the invention relates to a peptide or polypeptide which comprises the amino acid sequence of an epitope-bearing portion of an Interferon polypeptide having an amino acid sequence described in (a) or (b), above. Peptides or polypeptides having the amino acid sequence of an epitope-bearing portion of an Interferon polypeptide of the invention include portions of such polypeptides with at least six or seven, preferably at least nine, and more preferably at least about 30 amino acids to about 50 amino acids, although epitope-bearing polypeptides of any length up to and including the entire amino acid sequence of a polypeptide of the invention described above also are included in the invention.

In another embodiment, the invention provides an isolated antibody that binds specifically to an Interferon polypeptide having an amino acid sequence described in (a) or (b) above. The invention further provides methods for isolating antibodies that bind specifically to an Interferon polypeptide having an amino acid sequence as described herein. Such antibodies are useful therapeutically as described below.

In another aspect, the invention further provides an isolated feline Interferon polypeptide comprising an amino acid sequence selected from: (a) the amino acid sequence of an Interferon polypeptide including an acid sequence shown in at least one of SEQ ID NO: 2, 4, 6, 8, 10, 12, 14, 16, 18, 20, 22, 24 or 26; and (b) the amino acid sequence of a biologically active fragment of a polypeptide shown in at least one of SEQ ID NO: 2, 4, 6, 8, 10, 12, 14, 16, 18, 20, 22, 24 or 26. The polypeptides of the present invention also include polypeptides having an amino acid sequence at least 80% identical, more preferably at least 90% identical, and still more preferably 95%, 96%, 97%, 98% or 99% identical to those described in (a) or (b) above, as well as polypeptides having an amino acid sequence with at least 90% similarity, and more preferably at least 95% similarity, to those above. Polynucleotides encoding such polypeptides are also provided.

An additional embodiment of this aspect of the invention relates to a peptide or polypeptide which comprises the amino acid sequence of an epitope-bearing portion of a feline Interferon polypeptide having an amino acid sequence described in (a) or (b), above. Peptides or polypeptides having the amino acid sequence of an epitope-bearing portion of a feline Interferon polypeptide of the invention include portions of such polypeptides with at least six or seven, preferably at least nine, and more preferably at least about 30 amino acids to about 50 amino acids, although epitope-bearing polypeptides of any length up to and including the entire amino acid sequence of a polypeptide of the invention described above also are included in the invention.

In another embodiment, the invention provides an isolated antibody that binds specifically to a feline Interferon polypeptide having an amino acid sequence described in (a) or (b) above. The invention further provides methods for isolating antibodies that bind specifically to a feline Interferon polypeptide having an amino acid sequence as described herein. Such antibodies are useful therapeutically as described below.

In another aspect, the invention further provides an isolated Rhesus Interferon polypeptide comprising an amino acid sequence selected from: (a) the amino acid sequence of an Interferon polypeptide including an acid sequence shown in at least one of SEQ ID NO: 28, 30, 32, 34 or 36; and (b) the amino acid sequence of a biologically active fragment of a polypeptide shown in at least one of SEQ ID NO: 28, 30, 32, 34 or 36. The polypeptides of the present invention also include polypeptides having an amino acid sequence at least 80% identical, more preferably at least 90% identical, and still more preferably 95%, 96%, 97%, 98% or 99% identical to those described in (a) or (b) above, as well as polypeptides having an amino acid sequence with at least 90% similarity, and more preferably at least 95% similarity, to those above. Polynucleotides encoding such polypeptides are also provided.

An additional embodiment of this aspect of the invention relates to a peptide or polypeptide which comprises the amino acid sequence of an epitope-bearing portion of a Rhesus Interferon polypeptide having an amino acid sequence described in (a) or (b), above. Peptides or polypeptides having the amino acid sequence of an epitope-bearing portion of a Rhesus Interferon polypeptide of the invention include portions of such polypeptides with at least six or seven, preferably at least nine, and more preferably at least about 30 amino acids to about 50 amino acids, although epitope-bearing polypeptides of any length up to and including the entire amino acid sequence of a polypeptide of the invention described above also are included in the invention.

In another embodiment, the invention provides an isolated antibody that binds specifically to a Rhesus Interferon polypeptide having an amino acid sequence described in (a) or (b) above. The invention further provides methods for isolating antibodies that bind specifically to a Rhesus Interferon polypeptide having an amino acid sequence as described herein. Such antibodies are useful therapeutically as described below.

In another aspect, the invention further provides an isolated human Interferon polypeptide comprising an amino acid sequence selected from: (a) the amino acid sequence of an Interferon polypeptide including an acid sequence shown in at least one of SEQ ID NO: 38, 40, 42, 44, 46, 48, 50, 52, 54, 56, 58, 60, 62, 64, 66, 68, 70, 72, 74, 76, 78, 80, 82, 84 or 86; and (b) the amino acid sequence of a biologically active fragment of at least one of a polypeptide shown in SEQ ID NO: 38, 40, 42, 44, 46, 48, 50, 52, 54, 56, 58, 60, 62, 64, 66, 68, 70, 72, 74, 76, 78, 80, 82, 84 or 86. The polypeptides of the present invention also include polypeptides having an amino acid sequence at least 80% identical, more preferably at least 90% identical, and still more preferably 95%, 96%, 97%, 98% or 99% identical to those described in (a) or (b) above, as well as polypeptides having an amino acid sequence with at least 90% similarity, and more preferably at least 95% similarity, to those above. Polynucleotides encoding such polypeptides are also provided.

An additional embodiment of this aspect of the invention relates to a peptide or polypeptide which comprises the amino acid sequence of an epitope-bearing portion of a human Interferon polypeptide having an amino acid sequence described in (a) or (b), above. Peptides or polypeptides having the amino acid sequence of an epitope-bearing portion of a human Interferon polypeptide of the invention include portions of such polypeptides with at least six or seven, preferably at least nine, and more preferably at least about 30 amino acids to about 50 amino acids, although epitope-bearing polypeptides of any length up to and including the entire amino acid sequence of a polypeptide of the invention described above also are included in the invention.

In another embodiment, the invention provides an isolated antibody that binds specifically to a human Interferon polypeptide having an amino acid sequence described in (a) or (b) above. The invention further provides methods for isolating antibodies that bind specifically to a human Interferon polypeptide having an amino acid sequence as described herein. Such antibodies are useful therapeutically as described below.

In another aspect, the invention further provides compositions comprising any of the Interferon polynucleotides or Interferon polypeptides, described herein, for administration to cells in vitro to cells ex vivo and to cells in vivo, or to a multicellular organism. In certain particularly preferred embodiments of this aspect of the invention, the compositions comprise an Interferon polynucleotide for expression of an Interferon polypeptide in a host organism for treatment of disease. Particularly preferred in this regard is expression in a human patient for treatment of a dysfunction associated with loss of endogenous activity of an interferon.

The invention also provides for pharmaceutical compositions comprising Interferon polypeptides which may be employed, for instance, to treat immune system-related disorders such as viral infection, parasitic infection, bacterial infection, cancer, autoimmune disease, multiple sclerosis, lymphoma and allergy. Methods of treating individuals in need of interferon polypeptides are also provided. In certain preferred embodiments, the subject pharmaceutical composition is a veterinary composition for adminstration to a non-human animal, preferably a non-human primate. Exemplary conditions which can be treated with an Interferon include but are not limited to cell proliferation disorders, in particular cancer (e.g., hairy cell leukemia, Kaposi's sarcoma, chronic myelogenous leukemia, multiple myeloma, basal cell carcinoma and malignant melanoma, ovarian cancer, cutaneous T cell lymphoma), and viral infections. Without limitation, treatment with Interferon may be used to treat conditions which would benefit from inhibiting the replication of interferon-sensitive viruses. Viral infections which may be treated in accordance with the invention include hepatitis A, hepatitis B, hepatitis C, other non-A/non-B hepatitis, herpes virus, Epstein-Barr virus (EBV), cytomegalovirus (CMV), herpes simplex, human herpes virus type 6 (HHV-6), papilloma, poxvirus, picomavirus, adenovirus, rhinovirus, human T lymphotropic virus-type 1 and 2 (HTLV-1-2), human rotavirus, rabies, retroviruses including human immunodeficiency virus (HIV), encephalitis and respiratory viral infections. The method of the invention can also be used to modify various immune responses.

In one embodiment, the subject interferons can be used as anti-viral agents. Interferons have been used clinically for anti-viral therapy, for example, in the treatment of acquired immune disorders, viral hepatitis including chronic hepatitis B, hepatitis C, hepatitis D, papilloma viruses, herpes, viral encephalitis, and in the prophylaxis of rhinitis and respiratory infections.

In another embodiment, the subject Interferon can be used as anti-parasitic agents. The subject Interferons may be used, for example, for treating Cryptosporidium parvum infection.

In still another embodiment, the subject Interferons can be used as anti-bacterial agents. Interferons have been used clinically for anti-bacterial therapy. For example, the subject Interferons can be used in the treatment of multidrug-resistant pulmonary tuberculosis.

In yet another embodiment, the subject Interferons can be used as anti-cancer agents. Interferon therapy using the subject Interferons can be used in the treatment of numerous cancers e.g., hairy cell leukemia, acute myeloid leukemia, osteosarcoma, basal cell carcinoma, glioma, renal cell carcinoma, multiple myeloma, melanoma, and Hodgkin's disease.

In yet another embodiment, the subject Interferons can be used as part of an immunotherapy protocol. The Interferons of the present invention may be used clinically for immunotherapy or more particularly, for example, to prevent graft vs. host rejection, or to curtail the progression of autoimmune diseases, such as arthritis, multiple sclerosis, or diabetes is In another embodiment, the subject Interferons can be used as part of a program for treating allergies.

In still another embodiment, the subject Interferons can be used as vaccine adjuvants. The subject Interferons may be used as an adjuvant or coadjuvant to enhance or stimulate the immune response in cases of prophylactic or therapeutic vaccination.

In addition to the treatment of animals in general, the specific invention particularly contemplates the use of the subject Interferons for the treatment of primates as part of veterinary protocols. In one embodiment, the interferon is a Rhesus interferon.

In addition to the treatment of animals in general, the specific invention particularly contemplates the use of the subject Interferons for the treatment of cats as part of veterinarian protcols. In one embodiment, the Interferon is a feline Interferon.

In certain embodiments, the subject Interferons are used to treat cats for viral infections. For instance, cats with Feline Immunodeficiency Virus (FIV) require support therapies in order to maintain normal health. The subject interferons can be used as part of a treatment of cats infected with FIV.

Likewise, the subject Interferons can be used as part of a treatment of cats infected with Feline Leukemia Virus (FeLV). The feline leukemia virus (FeLV) is the causative agent of the most important fatal infectious disease complex of American domestic cats today.

Interferons can be used for treating feline panleukopenia Also called feline infectious enteritis, feline "distemper," and feline ataxia or incoordination, feline panleukopenia is a highly contagious viral disease of cats characterized by its sudden onset, fever, inappetence (loss of appetite), dehydration, depression, vomiting, decreased numbers of circulating white blood cells (leukopenia), and often a high mortality rate. Intrauterine (within the uterus) infection may result in abortions, stillbirths, early neonatal deaths, and cerebellar hypoplasia (underdevelopment of the cerebellum) manifested by incoordination (ataxia) in kittens beginning at two to three weeks of age. All members of the cat family (Felidae) are susceptible to infection with feline panleukopenia virus (FPV), as are raccoons, coatimundis, and ringtails, in the family Procyoniclae.

Interferons can be used for treating cats infected with feline infectious peritonitis.

Interferons can be used for treating cats infected with rabies.

In other embodiments directed to feline care, the subject Interferons can be used in treating inflammatory airway disease (LAD).

In still another embodiment, the subject Interferons can be used to treat dogs or other household pets.

In still another embodiment, the subject Interferons can be used to treat farm animals.

The subject invention also contemplates functional antagonists, e.g., wherein one or more amino acid residues are different from the wild-type Interferon, which inhibit one or more biological activities of the wild-type Interferon. Such antagonists can be used to treat disorders resulting from aberrant overexpression or other activation of an endogenous interferon. The functional antagonists may be formulated in a pharmaceutical preparation.

The present invention also provides a screening method for identifying compounds capable of enhancing or inhibiting a biological activity of an Interferon polypeptide, which involves contacting a receptor which is enhanced by an Interferon polypeptide with the candidate compound in the presence of an Interferon polypeptide, assaying, for example, anti-viral activity in the presence of the candidate compound and an Interferon polypeptide, and comparing the activity to a standard level of activity, the standard being assayed when contact is made between the receptor and Interferon in the absence of the candidate compound. In this assay, an increase in activity over the standard indicates that the candidate compound is an agonist of Interferon activity and a decrease in activity compared to the standard indicates that the compound is an antagonist of Interferon activity.

An additional aspect of the invention is related to a method for treating an animal in need of an increased level of interferon activity in the body comprising administering to such an animal a composition comprising a therapeutically effective amount of an isolated Interferon polypeptide of the invention or an agonist thereof.

A still further aspect of the invention is related to a method for treating an animal in need of a decreased level of interferon activity in the body comprising, administering to such an animal a composition comprising a therapeutically effective amount of an Interferon antagonist. Preferred antagonists for use in the present invention are Interferon-specific antibodies.

Administration of the described dosages may be every other day, but is preferably once or twice a week. Doses are usually administered over at least a 24 week period by injection.

Administration of the dose can be intravenous, subcutaneous, intramuscular, or any other acceptable systemic method. Based on the judgment of the attending clinician, the amount of drug administered and the treatment regimen used will, of course, be dependent on the age, sex and medical history of the patient being treated, the neutrophil count (e.g. the severity of the neutropenia), the severity of the specific disease condition and the tolerance of the patient to the treatment as evidenced by local toxicity and by systemic side-effects. Dosage amount and frequency may be determined during initial screenings of neutrophil count.

Conventional pharmaceutical formulations can be also prepared using the subject interferon compositions of the present invention. The formulations comprise a therapeutically effective amount of an Interferon polypeptide together with pharmaceutically acceptable carriers. For example, adjuvants, diluents, preservatives and/or solubilizers, if needed, may be used in the practice of the invention. Pharmaceutical compositions of interferon including those of the present invention may include diluents of various buffers (e.g., Tris-HCl, acetate, phosphate) having a range of pH and ionic strength, carriers (e.g., human serum albumin), solubilizers (e.g., Polyoxyethylene Sorbitin or TWEEN™ polysorbate), and preservatives (e.g., thimerosol, benzyl alcohol). See, for example, U.S. Pat. No. 4,496,537.

The amount of the Interferon composition administered to treat the conditions described above is based on the Interferon activity of the composition. It is an amount that is sufficient to significantly affect a positive clinical response. Although the clinical dose will cause some level of side effects in some patients, the maximal dose for mammals including humans is the highest dose that does not cause unmanageable clinically-important side effects. For purposes of the present invention, such clinically important side effects are those which would require cessation of therapy due to severe flu-lilce symptoms, central nervous system depression, severe gastrointestinal disorders, alopecia, severe pruritus or rash Substantial white and/or red blood cell and/or liver enzyme abnormalities or anemia-like conditions are also dose limiting.

Naturally, the dosages of Interferon may vary somewhat depending upon the formulation, selected. In general, however, the Interferon composition is administered in amounts ranging from about 100,000 to about several million IU/m² per day, based on the mammal's condition. The range set forth above is illustrative and those skilled in the art will determine the optimal dosing of Interferon selected based on clinical experience and the treatment indication.

The pharmaceutical compositions may be in the form of a solution, suspension, tablet, capsule, lyophilized powder or the like, prepared according to methods well known in the art It is also contemplated that administration of such compositions will be chiefly by the parenteral route although oral or inhalation routes may also be used depending upon the needs of the artisan.

The term "isolated" as used herein with respect to nucleic acids, such as DNA or RNA, refers to molecules separated from other DNAs or RNAs, respectively, that are present in the natural source of the macromolecule. The term isolated also refers to a nucleic acid or peptide that is substantially free of cellular material or culture medium when produced by recombinant DNA techniques, or chemical precursors or other chemicals when chemically synthesized. Moreover, an "isolated nucleic acid" is meant to include nucleic acid fragment which are not naturally occurring as fragments and would not be found in the natural state.

The practice of the present invention will employ, unless otherwise indicated, conventional techniques of cell biology, cell culture, moledular biology, transgenic biology, microbiology, recombinant DNA, and immunology, which are within the skill of the art. Such techniques are described in the literature. See, for example, *Molecular Cloning A Laboratory Manual,* 2nd Ed., ed. by Sambrook, Fritsch and Maniatis (Cold Spring Harbor Laboratory Press: 1989); *DNA Cloning,* Volumes I and II (D. N. Glover ed., 1985); *Oligonucleotide Synthesis* (M. J. Gait ed., 1984); Mullis et al. U.S. Pat. No. 4,683,195; Nucleic Acid Hybridization (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); Gene Transfer Vectors For Mammalian Cells (J. H. Miller and M. P. Calos eds., 1987, Cold Spring Harbor Laboratory); *Methods In Enzymology,* Vols. 154 and 155 (Wu et al. eds.), *Immunochemical Methods In Cell And Molecular Biology* (Mayer and Walker, eds., Academic Press, London, 1987); Handbook Of Experimental Immunology, Volumes I-IV (D. M. Weir and C. C. Blackwell, eds., 1986); *Manipulating the Mouse Embryo,* (Cold Spring Harbor Laboratory Press, Cold Spring Harbor, N.Y., 1986).

Other features and advantages of the invention will be apparent from the following detailed description, and from the claims.

BRIEF DESCRIPTION OF THE DRAWINGS

Table 1 shows the antiviral activity of the feline IFNα species.

Table 2 shows the antiviral activity of the Rhesus IFNα species.

Table 3 shows the sequence of the PCR primers used to amplify the human IFNα species. The sequences for these primers are set forth as follows: #1154 (SEQ ID NO 87); #1155 (SEQ ID NO 88); #1349 (SEQ ID NO 89); #1350 (SEQ ID NO 90); #1447 (SEQ ID NO 91); #1448 (SEQ ID NO 92); #1351 (SEQ ID NO 93); #1352 (SEQ ID NO 94); #1480 (SEQ ID NO 95); and #1481 (SEQ ID NO 96).

Table 4 shows the primer pairs (described in detail in Table 3) used to identify each of the human IFNα species.

DETAILED DESCRIPTION OF THE INVENTION

I. Exemplary Preparations

In another aspect, the present invention provides pharmaceutical preparations comprising Interferons, Interferon agonists or Interferon antagonists. The Interferons, Interferon agonists and/or Interferon antagonists for use in the subject method may be conveniently formulated for administration with a biologically acceptable medium, such as water, buffered saline, polyol (for example, glycerol, propylene glycol, liquid polyethylene glycol and the like) or suitable mixtures thereof. The optimum concentration of the active ingredient(s) in the chosen medium can be determined empirically, according to procedures well known to medicinal chemists. As used herein, "biologically acceptable medium" includes any and all solvents, dispersion media, and the like which may be appropriate for the desired route of administration of the pharmaceutical preparation. The use of such media for pharmaceutically active substances is known in the art. Except insofar as any conventional media or agent is incompatible with the activity of the compositions of the present invention, its use in the pharmaceutical preparation of the invention is contemplated. Suitable vehicles and their formulation inclusive of other proteins are described, for example, in the book Remington's Pharmaceutical Sciences (Remington's Pharmaceutical Sciences. Mack Publishing Company, Easton, Pa, USA 1985). These vehicles include injectable "deposit formulations".

Pharmaceutical formulations of the present invention can also include veterinary compositions, e.g., pharmaceutical preparations of the compositions of the present invention suitable for veterinary uses, e.g., for the treatment of livestock, non-human primate, or domestic animals, e.g., dogs and cats.

Rechargeable or biodegradable devices may also provide methods of introduction. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for sustained release at a particular target site.

The preparations of the present invention may be given orally, parenterally, topically, or rectally. They are of course given by forms suitable for each administration route. For example, they are administered in tablets or capsule form, by injection, inhalation, eye lotion, ointment, suppository, controlled release patch, etc., administration by injection, infusion or inhalation; topical by lotion or ointment; and rectal by suppositories. Oral and topical administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms such as described below or by other conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular composition employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above.

If desired, the effective daily dose of the active compound may be administered as two, three, four, five, six or more sub-doses administered separately at appropriate intervals throughout the day, optionally, in unit dosage forms.

The term "treatment" is intended to encompass also prophylaxis, therapy, and cure.

The patient receiving this treatment is any animal in need, including primates, in particular humans, and other mammals such as equines, cattle, swine and sheep; and poultry and pets in general.

The compound of the invention can be administered as such or in admixtures with pharmaceutically acceptable and/or sterile carriers and can also be administered in conjunction with other agents. Non-limiting examples of such agents include antimicrobial agents such as penicillins, cephalosporins, aminoglycosides, and glycopeptides. Conjunctive therapy, thus includes sequential, simultaneous and separate administration of the active compound in a way that the therapeutic effects of the first administered one is not entirely disappeared when the subsequent is administered.

II Pharmaceutical Compositions

While it is possible for a compound of the present invention to be administered alone, it is preferable to administer the compound as a pharmaceutical formulation (composition). The compositions of the present invention may be formulated for administration in any convenient way for use in human or veterinary medicine. In certain embodiments, the compound included in the pharmaceutical preparation may be active itself, or may be a prodrug, e.g., capable of being converted to an active compound in a physiological setting.

Thus, another aspect of the present invention provides pharmaceutically acceptable compositions comprising a therapeutically effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin; or (4) intravaginally or intrarectally, for example, as a pessary, cream or foam. However, in certain embodiments the subject compounds may be simply dissolved or suspended in sterile water. In certain embodiments, the pharmaceutical preparation is non-pyrogenic, i.e., does not elevate the body temperature of a patient.

The phrase "therapeutically effective amount" as used herein means that amount of a compound, material, or composition comprising a compound of the present invention which is effective for producing some desired therapeutic effect in at least a sub-population of cells in an animal and thereby blocking the biological consequences of that pathway in the treated cells, at a reasonable benefit/risk ratio applicable to any medical treatment The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject agonists from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid, (16) pyrogen-free water; (17) isotonic saline; (18) Ringer's solution; (19) ethyl alcohol; (20) phosphate buffer solutions; and (21) other non-toxic compatible substances employed in pharmaceutical formulations.

III. Variant Interferon Polypeptides

It is anticipated that certain mutant forms (or variants) of the Interferon polypeptides of the invention may act as agonist or antagonists. While not wishing to be bound to any particular theory, it is well lcnown that mutant forms of protein signaling factors are capable of binding to the appropriate receptor and yet not capable of activating the receptor. Such mutant proteins act as antagonists by displacing the wild-type proteins and blocking the normal receptor activation. Additionally, it is well known that one or more amino acid substitutions can be made to many proteins inorder to enhance their activity in comparison to wildtype forms of the protein. Such agonists may have, for example, increased half-life, binding affinity, or activity in comparison to the wildtype protein. There are many well known methods for obtaining mutants (or variants) with a desired activity.

Methods for generating large pools of mutant/variant proteins are well known in the art. In one embodiment, the invention contemplates using Interferon polypeptides generated by combinatorial mutagenesis. Such methods, as are known in the art, are convenient for generating both point and truncation mutants, and can be especially useful for identifying potential variant sequences (e.g., homologs) that are functional in a given assay. The purpose of screening such combinatorial libraries is to generate, for example, Interferon variants homologs that can act as either agonists or antagonists. Thus, combinatorially derived variants can be generated to have an increased potency relative to a naturally occurring form of the protein. Likewise, Interferon variants can be generated by the present combinatorial approach to act as antagonists, in that they are able to mimic, for example, binding to other extracellular matrix components (such as receptors), yet not induce any biological response, thereby inhibiting the action of Interferon polypeptides or Interferon agonists. Moreover, manipulation of certain domains of Interferon by the present method can provide domains more suitable for use in fusion proteins, for example, domains demonstrated to have specific useful properties.

To further illustrate the state of the art of combinatorial mutagenesis, it is noted that the review article of Gallop et al. (1994) J Med Chem 37:1233 describes, the general state of the art of combinatorial libraries as of the earlier 1990's. In particular, Gallop et al state at page 1239"[s]creening the analog libraries aids in determining the minimum size of the active sequence and in identifying those residues critical for binding and intolerant of substitution". In addition, the Ladner et al. PCT publication WO90/02809, the Goeddel et al. U.S. Pat. No. 5,223,408, and the Markland et al. PCT publication WO92/15679 illustrate specific techniques which one skilled in the art could utilize to generate libraries of variants which can be rapidly screened to identify variants/fragments which possess a particular activity. These techniques are exemplary of the art and demonstrate that large libraries of related variants/truncants can be generated and assayed to isolate particular variants without undue experimentation. Gustin et al. (1993) Virology 193:653, and Bass et al. (1990) Proteins: Structure, Function and Genetics 8:309-314 also describe other exemplary techniques from the art which can be adapted as a means for generating mutagenic variants of the Interferon polypeptides of the invention.

Indeed, it is plain from the combinatorial mutagenesis art that large scale mutagenesis of Interferon proteins, without any preconceived ideas of which residues were critical to the biological function, can generate wide arrays of variants having equivalent biological activity. Alternatively, such methods can be used to generate a wide array of variants having enhanced activity or antagonistic activity. Indeed, it is the ability of combinatorial techniques to screen billions of different variants by high throughout analysis that removes any requirement of a priori understanding or knowledge of critical residues.

IV Antibody Antagonists

It is anticipated that some antibodies can act as Interferon antagonists. Antibodies can have extraordinary affinity and specificity for particular epitopes. The binding of an antibody to its epitope on a protein may antagonize the function of that protein by competitively or non-competitively inhibiting the interaction of that protein with other proteins necessary for proper function.

Antibodies with Interferon antagonist activity can be identified in much the same way as other Interferon antagonists. For example, candidate antibodies can be administered to cells expressing a reporter gene, and antibodies that cause decreased reporter gene expression are antagonists.

In one variation, antibodies of the invention can be single chain antibodies (scFv), comprising variable antigen binding domains linked by a polypeptide linker. Single chain antibodies are expressed as a single polypeptide chain and can be expressed in bacteria and as part of a phage display library. In this way, phage that express the appropriate scFv will have Interferon antagonist activity. The nucleic acid encoding the single chain antibody can then be recovered from the phage and used to produce large quantities of the scFv. Construction and screening of scFv libraries is extensively described in various publications (U.S. Pat. Nos. 5,258,498; 5,482,858; 5,091,513; 4,946,778; 5,969,108; 5,871,907; 5,223,409; 5,225,539).

Exemplification

The invention now being generally described, it will be more readily understood by reference to the following examples which are included merely for purposes of illustration of certain aspects and embodiments of the present invention, and are not intended to limit the invention.

EXAMPLE 1

Isolation of Feline IFNα Clones

Feline IFNα clones were isolated by PCR amplification of genomic DNA from a cat lung cell line (AKD) using standard methods. Nine distinct sequences were isolated and designated Fe-IFN-αA (SEQ ID NO: 9), Fe-IFN-aB (SEQ ID NO: 11), Fe-IFN-αC (SEQ ID NO: 13), Fe-IFN-αD (SEQ ID NO: 15), Fe-IFN-αE (SEQ ID NO: 17), Fe-IFN-αF (SEQ ID NO: 19), Fe-IFN-αG (SEQ ID NO: 21), Fe-INF-AH (SEQ ID NO: 23), and Fe-IFN-αI (SEQ ID NO: 25). Amino acid sequences corresponding to each of these are also provided: Fe-IFN-αA (SEQ ID NO: 10), Fe-IFN-αB (SEQ ID NO: 12), Fe-IFN-aC (SEQ ID NO: 14), Fe-IFN-αD (SEQ ID NO: 16), Fe-IFN-αE (SEQ ID NO: 18), Fe-IFN-αF (SEQ ID NO: 20), Fe-IFN-αG (SEQ ID NO: 22), Fe-IFN-αH (SEQ ID NO: 24), and Fe-IFN-αI (SEQ ID NO: 26).

PCR was performed using standard procedure. Two rounds of amplification from genomic DNA were performed. Flanking primers used to amplify the feline sequences are:

```
                                     (SEQ ID NO: 97)
5' primer: 5'-CTCTTCCTTCTTGGTGGCCCTG-3'

(SEQ ID NO: 98)
3' primer: 5'-GTGATGAGTCAGTGAGAATCATTTC-3'
```

EXAMPLE 2

Antiviral Activity of the Feline IFNα Species

The antiviral activity of the subject Interferon species was measured using a cytopathic effect assay (CPE). Briefly, serial dilution of Interferon were incubated with test cells for 1 to 4 hours at 37 C. Virus was then added to the cells and incubated for 16 hours at 37 C. The surviving cells were visualized by uptake of crystal violet stain, and the dilution of Interferon at which approximately 50% of the cells survive viral infection was determined.

Table 1 summarizes the results of these experiments which demonstrate that feline IFN-αA, IFN-αB, IFN-αC, IFN-αD, IFN-αE, IFN-αF, IFN-αG, and IFN-αI each possess antiviral activity as measured by CPE. The activity of feline IFN-αH was not determined in this assay. In this particular experiment, the test cells were AKD feline lung cells and the virus was vesicular stromatitis virus (VSV).

EXAMPLE 3

Isolation of Rhesus IFNa Clones

Rhesus monkey IFNα clones were isolated by PCR amplification of genomic DNA from a Rhesus monkey kidney cell line (LLCMK-2) using standard methods. Two separate primer pairs were used to amplify sequences. Using the first primer pair, one sequence was isolated and designated Rh-IFN-α4b (SEQ ID NO: 29). The amino acid sequence corresponding to the Rh-IFN-α4b nucleic acid sequence is designated in SEQ ID NO: 30.

PCR was performed using standard procedure. Two rounds of amplification from genomic DNA were performed. Flanking primers used to amplify this Rhesus sequence are:

```
                                     (SEQ ID NO: 99)
5' primer: 5'-CTTCAGAGAACCTGGAGCC-3'
                                     (SEQ ID NO: 100)
3' primer: 5'-AATCATTTCCATGTTGAACCAG-3'
```

Three additional Rhesus IFNα clones were isolated by PCR amplification of genomic DNA from a Rhesus monkey kidney cell line (LLCMK-2) using standard methods and a second primer pair: Rh-IFN-αD1 (SEQ ID NO: 31), Rh-IFN-αD2 (SEQ ID NO: 33), and Rh-IFN-aD3 (SEQ ID NO: 35). Amino acid sequences corresponding to each of these are also provided: Rh-IFN-aD1 (SEQ ID NO: 32), Rh-IFN-aD2 (SEQ ID NO: 34), and Rh-IFN-αD3 (SEQ ID NO: 36).

PCR was performed using standard procedures. Two rounds of amplification from genomic DNA were performed. Flanking primers used to amplify these Rhesus sequences are:

```
                                     (SEQ ID NO: 101)
5' primer: 5'-AGAAGCATCTGCCTGCAATATC-3'

(SEQ ID NO: 102)
3' primer: 5'-GCTATGACCATGATTACGAATTC-3'
```

EXAMPLE 4

Antiviral Activity of the Rhesus IFNa Species

The antiviral activity of the subject Interferon species was measured using a cytopathic effect assay (CPE). Briefly, serial dilution of Interferon were incubated with test cells for 1 to 4 hours at 37° C. Virus was then added to the cells and incubated for 16 hours at 37° C. The surviving cells were visualized by uptake of crystal violet stain, and the dilution of Interferon at which approximately 50% of the cells survive viral infection was determined.

Table 2 summarizes the results of experiments which demonstrate that Rhesus IFN-α4b possesses antiviral activity as measured by an anti-viral activity assay (CPE). The activities of Rhesus IFN-αD1, IFN-αD2, and IFN-αD3 were not determined in this assay. This assay was performed using as test cells either Madin-Darby bovine kidney endothelial cells (MDBK) or African green monkey kidney cells (Vero) infected with VSV.

EXAMPLE 5

Isolation of human IFNα Clones

Eighteen human Interferon-a species were isolated in accordance with the procedures described in U.S. Pat. Nos. 5,789,551, 5,869,293, and 6,001,589. Briefly, human genomic DNA was analyzed by PCR using standard methods. The primers used in this analysis are described in Tables 3 and 4.

The eighteen human Interferon-α species identified using this approach are: hu-IFN-α001 (SEQ ID NO: 37), hu-IFN-α002 (SEQ ID NO: 39), hu-IFN-α003 (SEQ ID NO: 41), hu-IFN-α004 (SEQ ID NO: 43), hu-IFN-α005 (SEQ ID NO: 45), hu-IFN-α006 (SEQ ID NO: 47), hu-IFN-α007 (SEQ ID NO: 49), hu-IFN-α008 (SEQ ID NO: 51), hu-IFN-α009 (SEQ ID NO: 53), hu-IFN-α010 (SEQ ID NO: 55), hu-IFN-α011 (SEQ ID NO: 57), hu-IFN-α012 (SEQ ID NO: 59), hu-IFN-α013 (SEQ ID NO:61), hu-IFN-α014 (SEQ ID NO: 63), hu-IFN-α015 (SEQ ID NO: 65), hu-IFN-α016 (SEQ ID NO: 67), hu-IFN-α017 (SEQ ID NO: 69), hu-IFN-α018 (SEQ ID NO: 71). Amino acid sequences corresponding to each of these are also provided: IFN-α001 (SEQ ID NO: 38), hu-IFN-α002 (SEQ ID NO: 40), hu-IFN-α003 (SEQ ID NO: 42), hu-IFN-α004 (SEQ ID NO: 44), hu-IFN-α005 (SEQ ID NO: 46), hu-IFN-α006 (SEQ ID NO: 48), hu-IFN-α007 (SEQ ID NO: 50), hu-IFN-α008 (SEQ ID NO: 52), hu-IFN-α009 (SEQ ID NO: 54), hu-IFN-α010 (SEQ ID NO: 56), hu-IFN-α011 (SEQ ID NO: 58), hu-IFN-α012 (SEQ ID NO: 60), hu-IFN-α013 (SEQ ID NO: 62), hu-IFN-α014 (SEQ ID NO: 64), hu-IFN-α015 (SEQ ID NO: 66), hu-IFN-α016 (SEQ ID NO: 68), hu-IFN-α017 (SEQ ID NO: 70), hu-IFN-α018 (SEQ ID NO: 72).

Additionally, hu-IFN-α001 and hu-IFN-α012 were back translated using optimal *E. coli* codons and designated hu-IFN-α001-BT (SEQ ID NO: 73) and hu-IFN-α012-BT (SEQ ID NO: 75). Amino acid sequences corresponding to each of these are also provided: hu-IFN-α001-BT (SEQ ID NO: 74) and hu-IFN-α012-BT (SEQ ID NO: 76).

EXAMPLE 6

Isolation of Human IFNa Variants

During the construction of expression vectors containing the human IFNα species described in detail above, the following clones containing mutations were generated. These IFNa variants can be tested for activity. IFNα variants can contain silent substitutions, and thus have identical activity to the wild type IFNα species. Alternatively, a variant may contain a substitution that alters the activity of the polypeptide. The substitution may increase, enhance or augment the activity, and thus be an IFNa agonist. Additionally, the substitution may decrease or interfere with the activity, and thus be an IFNαantagonist.

Nucleic acid sequences for the variant species are provided: hu-IFN-α019 (SEQ ID NO: 77), hu-IFN-α020 (SEQ ID NO: 79), hu-IFN-α021 (SEQ ID NO: 81), hu-IFN-α022 (SEQ ID NO: 83), and hu-IFN-α023 (SEQ ID NO: 85). Amino acid sequences corresponding to each of these are also provided: hu-IFN-α019 (SEQ ID NO: 78), hu-IFN-α020 (SEQ ID NO: 80), hu-IFN-α021 (SEQ ID NO: 82), hu-IFN-α022 (SEQ ID NO: 84), and hu-IFN-α023 (SEQ ID NO: 86).

The variants provided herein are generated from the human IFNa species described in detail in Example 5. hu-IFN-α002, hu-IFN-α005, hu-IFN-α007, hu-IFN-α013, and hu-IFN-α015 gave rise to the variants hu-IFN-α19, hu-IFN-α020, hu-IFN-α021, hu-IFN-α022, and hu-IFN-α023, respectively.

EXAMPLE 7

Antiviral Activity of the Human IFNα Species

The antiviral activity of the human IFNα species was also determined using the CPE assay, as outlined in detail above. The assay was performed using the following test cell and virus combinations: MDBK test cells with VSV; human epithelial squamous (HEP-2) cells with VSV; mouse connective tissue fibroblasts (L929) with EMC; human lung squamous (H226) cells with VSV; and human lung fibroblasts with influenza virus.

EXAMPLE 8

Additional Activities of the Human IFNα Species

In addition to the anti-viral activity outlined in detail in Example 7, the activity of the subject Interferonα species was also tested in two additional assays.

a. MHC Class I induction assay: To examine the ability of human IFNs to induce MHC class I (HLA-B7) antigen expression in human amnion epitlielial cells (WISH), HeLa, or HEP-2 cells, $2.5 \times 10^5$ cells per well (6-well plate) are incubated with IFN for 72 hours. Subsequently, cell surface expression of the HLA-B7 antigen is detected by treatment of cells with mouse anti-HLA (W6/32) monoclonal antibodies followed by treatment with fluorescein isothiocyanate-conjugated goat anti-mouse IgG. The cells are then subjected to flow cytometry to quantitate the level of cell surface MHC class I antigen expression per 10,000 cells.

b. Antiproliferative assay: To examine the ability of human IFNs to reduce cell proliferation rate, 5 to $10 \times 10^4$ H226 human mesothelioma cells are seeded per well of a 96-well plate and are incubated with IFN test samples or standards at 37° C. for 3 to 7 days. Viable cells are visualized by uptake of crystal violet stain. After washing off excess stain, the intensity of remaining color is proportional to the number of viable cells in the well and is measured vs. that produced by IFN standards.

hu-IFNα-012 demonstrated robust antiproliferative activity in this assay.

All publications and patents cited herein are hereby incorporated by reference in their entirety.

Those skilled in the art will recognize, or be able to ascertain using no more than routine experimentation, many equivalents to the specific embodiments of the invention described herein. Such equivalents are intended to be encompassed by the following claims.

TABLE 1

Antiviral Activity of Fe-IFN-alpha Species

| Fe-IPN | Crude Lysate AVA (u/ml) | SA (u/mg) | Protein (mg/ml) |
|---|---|---|---|
| alphaA | $1.87 * 10^7$ | $2.23 * 10^8$ | $8.4 * 10^{-2}$ |
| alphaB | $1.87 * 10^7$ | $4.45 * 10^8$ | $4.2 * 10^{-2}$ |
| alphaC | $1.7 * 10^7$ | $1.06 * 10^9$ | $1.6 * 10^{-2}$ |
| alphaD | $1.87 * 10^7$ | $2.97 * 10^8$ | $6.3 * 10^{-2}$ |
| alphaE | $2.59 * 10^6$ | $2.47 * 10^8$ | $1.1 * 10^{-2}$ |
| alphaF | $1.87 * 10^7$ | $5.94 * 10^8$ | $3.2 * 10^{-2}$ |
| alphaG | $3.74 * 10^7$ | $5.94 * 10^8$ | $6.3 * 10^{-2}$ |
| alphaH | No Activity | Not determined | Not determined |
| alphaI | $6.55 * 10^6$ | $6.55 * 10^6$ | $1.0 * 10^{-2}$ |

TABLE 2

Antiviral Activity of Rhesus Monkey-IFN-alpha Species

| Rhesus Monkey-IFN | AVA (u/ml) | SA (u/mg) | Protein (mg/ml) |
|---|---|---|---|
| Alpha4b | $4.68 * 10^8$ | $2.9 * 10^8$ | 1.62 |
| AlphaD1 | Not determined | Not determined | Not determined |
| AlphaD2 | Not determined | Not determined | Not determined |
| AlphaD3 | Not determined | Not determined | Not determined |

TABLE 3

Primers used for PCR Amplification of Human Interferons

| Primer Sequence | Forward/Reverse | Designation |
|---|---|---|
| 5' GCGGGCCCCAATGGCCYTGYCCTTT 3' | Forward | #1154 |
| 5' GCTCTAGAAYTCATGAAAGYGTGA 3' | Reverse | #1155 |
| 5' GCTCAGCAGCATCCRCAACATC 3' | Forward | #1349 |
| 5' CATTTCCGTGTTGTACCAGGTC 3' | Reverse | #1350 |
| 5' TCAGAAAACCTAGAGGCCG 3' | Forward | #1447 |
| 5' TGGAAGAACTCATGAAAGTGTG 3' | Reverse | #1448 |
| 5' CTCAAGTAGCCTAGCAATATTGGC 3' | Forward | #1351 |
| 5' GTATTAGTCAATACAGATCATTTCC 3' | Reverse | #1352 |
| 5' GTTACCCCTCATCAACCAGC 3' | Forward | #1480 |
| 5' GAATCATTTCCATGATGAACCA 3' | Reverse | #1481 |

The sequence of the primers are given in the 5' to 3' direction. The "Y" represents a pyrimidine (T or C). The "R" represents a purine (A or G).

TABLE 4

Primer Pairs Used for Amplification of Human Interferons

| Interferon | Forward Primer (5') | Reverse Primer (3') |
|---|---|---|
| IFN-alpha001 | #1154 | #1155 |
| IFN-alpha002 | #1447 | #1448 |
| IFN-alpha003 | #1447 | #1448 |
| IPN-alpha004 | #1447 | #1448 |
| IFN-alpha005 | #1447 | #1448 |
| IFN-alpha006 | #1447 | #1448 |
| IFN-alpha007 | #1447 | #1448 |
| IFN-alpha008 | #1351 | #1352 |
| IFN-alpha009 | #1351 | #1352 |
| IFN-alpha010 | #1447 | #1448 |
| IFN-alpha011 | #1480 | #1481 |
| IFN-alpha012 | #1480 | #1481 |
| IFN-alpha013 | #1351 | #1352 |
| IPN-alpha014 | #1351 | #1352 |
| IFN-alpha015 | #1349 | #1350 |
| IFN-alpha016 | #1349 | #1350 |
| IFN-alpha017 | #1154 | #1155 |
| IFN-alpha018 | #1351 | #1352 |
| IFN-alpha019 | #1447 | #1448 |
| IFN-alpha020 | #1447 | #1448 |
| IFN-alpha021 | #1447 | #1448 |
| IFN-alpha022 | #1351 | #1352 |
| IFN-alpha023 | #1349 | #1350 |

I claim:

1. An isolated interferon polypeptide comprising the amino acid sequence of SEQ ID NO: 68 or an amino acid sequence comprising no more than one amino acid difference compared to and over the length of SEQ ID NO: 66 or 86, wherein the isolated polypeptide has at least one biological activity selected from the group consisting of antiviral activity, antiproliferative activity, and MHC class I antigen expression induction activity.

2. A composition comprising the isolated interferon polypeptide of claim 1 and a pharmaceutically acceptable excipient.

3. The isolated interferon polypeptide of claim 1, wherein the isolated polypeptide comprises the amino acid sequence of SEQ ID NO: 66.

4. The isolated interferon polypeptide of claim 1, wherein the isolated polypeptide comprises the amino acid sequence of SEQ ID NO: 86.

5. An isolated interferon polypeptide comprising an amino acid sequence greater than 99% identical to SEQ ID NO: 86, or 100% identical to SEQ ID NO: 66 or 68, wherein the isolated polypeptide has enhanced antiviral activity compared to that of a wild-type interferon-α polypeptide.

6. The isolated interferon polypeptide of claim 1, wherein the isolated polypeptide comprises the amino acid sequence of SEQ ID NO: 68.

* * * * *

SEQUENCE LISTING

<160> NUMBER OF SEQ ID NOS: 102

<210> SEQ ID NO 1
<211> LENGTH: 516
<212> TYPE: DNA
<213> ORGANISM: Felis catus
<220> FEATURE:
<221> NAME/KEY: CDS
<222> LOCATION: (1)..(513)

<400> SEQUENCE: 1

```
tgt gac ctg cct cag acc cac gtc ctg ctg aac agg agg gcc ttg acg      48
Cys Asp Leu Pro Gln Thr His Val Leu Leu Asn Arg Arg Ala Leu Thr
1               5                   10                  15 ctc ctg gga caa atg agg aga ctc cct gcc agc tcc tgt cag aag gac      96
Leu Leu Gly Gln Met Arg Arg Leu Pro Ala Ser Ser Cys Gln Lys Asp
            20                  25                  30 aga aat gac ttc gcc ttc ccc cag gac gtg ttc ggt gga gac cag tcc     144
Arg Asn Asp Phe Ala Phe Pro Gln Asp Val Phe Gly Gly Asp Gln Ser
        35                  40                  45 cac aag gcc caa gcc ctc tcg gtg gtg cac gtg acg aac cag aag atc     192
His Lys Ala Gln Ala Leu Ser Val Val His Val Thr Asn Gln Lys Ile
    50                  55                  60 ttc cac ttc ttc tgc aca gag gcg tcc tcg tct gct gct tgg aac acc     240
Phe His Phe Phe Cys Thr Glu Ala Ser Ser Ser Ala Ala Trp Asn Thr
65                  70                  75                  80 acc ctc ctg gag gaa ttt tgc acg gga ctt gat cgg cag ctg acc cgc     288
Thr Leu Leu Glu Glu Phe Cys Thr Gly Leu Asp Arg Gln Leu Thr Arg
                85                  90                  95 ctg gaa gcc tgt gtc ctg cag gag gtg gag gag gga gag gct ccc ctg     336
Leu Glu Ala Cys Val Leu Gln Glu Val Glu Glu Gly Glu Ala Pro Leu
            100                 105                 110 acg aac gag gac att cat ccc gag gac tcc atc ctg agg aac tac ttc     384
```

```
Thr Asn Glu Asp Ile His Pro Glu Asp Ser Ile Leu Arg Asn Tyr Phe
        115                 120                 125 caa aga ctc tcc ctc tac ctg caa gag aag aaa tac agc cct tgt gcc       432
Gln Arg Leu Ser Leu Tyr Leu Gln Glu Lys Lys Tyr Ser Pro Cys Ala
        130                 135                 140 tgg gag atc gtc aga gca gaa atc atg aga tcc ttg tat tat tca tca       480
Trp Glu Ile Val Arg Ala Glu Ile Met Arg Ser Leu Tyr Tyr Ser Ser
145                 150                 155                 160 aca gcc ttg cag aaa aga tta agg agc gag aaa tga                       516
Thr Ala Leu Gln Lys Arg Leu Arg Ser Glu Lys
                165                 170

<210> SEQ ID NO 2
<211> LENGTH: 171
<212> TYPE: PRT
<213> ORGANISM: Felis catus

<400> SEQUENCE: 2

Cys Asp Leu Pro Gln Thr His Val Leu Leu Asn Arg Arg Ala Leu Thr
1               5                   10                  15

Leu Leu Gly Gln Met Arg Arg Leu Pro Ala Ser Ser Cys Gln Lys Asp
            20                  25                  30

Arg Asn Asp Phe Ala Phe Pro Gln Asp Val Phe Gly Gly Asp Gln Ser
        35                  40                  45

His Lys Ala Gln Ala Leu Ser Val Val His Val Thr Asn Gln Lys Ile
    50                  55                  60

Phe His Phe Phe Cys Thr Glu Ala Ser Ser Ala Ala Trp Asn Thr
65                  70                  75                  80

Thr Leu Leu Glu Glu Phe Cys Thr Gly Leu Asp Arg Gln Leu Thr Arg
                85                  90                  95

Leu Glu Ala Cys Val Leu Gln Glu Val Glu Glu Gly Glu Ala Pro Leu
            100                 105                 110

Thr Asn Glu Asp Ile His Pro Glu Asp Ser Ile Leu Arg Asn Tyr Phe
        115                 120                 125

Gln Arg Leu Ser Leu Tyr Leu Gln Glu Lys Lys Tyr Ser Pro Cys Ala
        130                 135                 140

Trp Glu Ile Val Arg Ala Glu Ile Met Arg Ser Leu Tyr Tyr Ser Ser
145                 150                 155                 160

Thr Ala Leu Gln Lys Arg Leu Arg Ser Glu Lys
                165                 170

<210> SEQ ID NO 3
<211> LENGTH: 501
<212> TYPE: DNA
<213> ORGANISM: Felis catus
<220> FEATURE:
<221> NAME/KEY: CDS
<222> LOCATION: (1)..(498)

<400> SEQUENCE: 3 tgt gac ctg cct cag acc cac gtc ctg ctg aac agg agg gcc ttg acg        48
Cys Asp Leu Pro Gln Thr His Val Leu Leu Asn Arg Arg Ala Leu Thr
1               5                   10                  15 ctc ctg gga caa atg agg aga ctc cct gcc agc tcc tgt cag aag gac        96
Leu Leu Gly Gln Met Arg Arg Leu Pro Ala Ser Ser Cys Gln Lys Asp
            20                  25                  30 aga aat gac ttc gcc ttc ccc cag gac gtg ttc ggt gga gac cag tcc       144
Arg Asn Asp Phe Ala Phe Pro Gln Asp Val Phe Gly Gly Asp Gln Ser
        35                  40                  45
```

```
cac aag gcc caa gcc ctc tcg gtg gtg cac gtg acg aac cag aag atc        192
His Lys Ala Gln Ala Leu Ser Val Val His Val Thr Asn Gln Lys Ile
 50                  55                  60 ttc cac ttc ttc tgc aca gag gcg tcc tcg tct gct gct tgg aac acc        240
Phe His Phe Phe Cys Thr Glu Ala Ser Ser Ser Ala Ala Trp Asn Thr
 65                  70                  75                  80 acc ctc ctg gag gaa ttc tgc acg gga ctt gat cgg cag ctg acc cgc        288
Thr Leu Leu Glu Glu Phe Cys Thr Gly Leu Asp Arg Gln Leu Thr Arg
                 85                  90                  95 ctg gaa gcc tgt gtc gtg cag gag gtg ggg gag gga gag gct ccc ctc        336
Leu Glu Ala Cys Val Val Gln Glu Val Gly Glu Gly Glu Ala Pro Leu
                100                 105                 110 acg aac gag gac tcc atc ctg agg aac tac ttc caa aga ctc tcc ctc        384
Thr Asn Glu Asp Ser Ile Leu Arg Asn Tyr Phe Gln Arg Leu Ser Leu
            115                 120                 125 tac ctg caa gag aag aaa tac agc cct tgt gcc tgg gag atc gtc aga        432
Tyr Leu Gln Glu Lys Lys Tyr Ser Pro Cys Ala Trp Glu Ile Val Arg
130                 135                 140 gca gaa atc atg aga tcc ttg tat tat tca tca aca gcc ttg cag aaa        480
Ala Glu Ile Met Arg Ser Leu Tyr Tyr Ser Ser Thr Ala Leu Gln Lys
145                 150                 155                 160 aga tta agg agc gag aaa tga                                            501
Arg Leu Arg Ser Glu Lys
                165

<210> SEQ ID NO 4
<211> LENGTH: 166
<212> TYPE: PRT
<213> ORGANISM: Felis catus

<400> SEQUENCE: 4

Cys Asp Leu Pro Gln Thr His Val Leu Leu Asn Arg Arg Ala Leu Thr
  1               5                  10                  15

Leu Leu Gly Gln Met Arg Arg Leu Pro Ala Ser Ser Cys Gln Lys Asp
                 20                  25                  30

Arg Asn Asp Phe Ala Phe Pro Gln Asp Val Phe Gly Gly Asp Gln Ser
             35                  40                  45

His Lys Ala Gln Ala Leu Ser Val Val His Val Thr Asn Gln Lys Ile
 50                  55                  60

Phe His Phe Phe Cys Thr Glu Ala Ser Ser Ser Ala Ala Trp Asn Thr
 65                  70                  75                  80

Thr Leu Leu Glu Glu Phe Cys Thr Gly Leu Asp Arg Gln Leu Thr Arg
                 85                  90                  95

Leu Glu Ala Cys Val Val Gln Glu Val Gly Glu Gly Glu Ala Pro Leu
                100                 105                 110

Thr Asn Glu Asp Ser Ile Leu Arg Asn Tyr Phe Gln Arg Leu Ser Leu
            115                 120                 125

Tyr Leu Gln Glu Lys Lys Tyr Ser Pro Cys Ala Trp Glu Ile Val Arg
130                 135                 140

Ala Glu Ile Met Arg Ser Leu Tyr Tyr Ser Ser Thr Ala Leu Gln Lys
145                 150                 155                 160

Arg Leu Arg Ser Glu Lys
                165

<210> SEQ ID NO 5
<211> LENGTH: 516
<212> TYPE: DNA
<213> ORGANISM: Felis catus
<220> FEATURE:
```

```
<221> NAME/KEY: CDS
<222> LOCATION: (1)..(513)

<400> SEQUENCE: 5 tgt gac ctg cct cag acc cac ggc ctg ctg aac agg agg gcc ttg acg        48
Cys Asp Leu Pro Gln Thr His Gly Leu Leu Asn Arg Arg Ala Leu Thr
1               5                   10                  15 ctc ctg gga caa atg agg aga ctc cct gcc agc tcc tgt cag aag gac        96
Leu Leu Gly Gln Met Arg Arg Leu Pro Ala Ser Ser Cys Gln Lys Asp
            20                  25                  30 aga aat gac ttc gcc ttc ccc cag gac gtg ttc ggt gga ggc cag tcc       144
Arg Asn Asp Phe Ala Phe Pro Gln Asp Val Phe Gly Gly Gly Gln Ser
        35                  40                  45 cac aag gcc caa gcc ctc tcg gtg gtg cac gtg acg aac cag aag atc       192
His Lys Ala Gln Ala Leu Ser Val Val His Val Thr Asn Gln Lys Ile
50                  55                  60 ttc cac ttc ttc tgc aca gag gcg tcc tcc tct gct gct tgg aac acc       240
Phe His Phe Phe Cys Thr Glu Ala Ser Ser Ser Ala Ala Trp Asn Thr
65                  70                  75                  80 acc ctc ctg gag gaa ttt tgc acg gga ctt gat cgg cag ctg acc cgc       288
Thr Leu Leu Glu Glu Phe Cys Thr Gly Leu Asp Arg Gln Leu Thr Arg
                85                  90                  95 ctg gaa gcc tgt gtc ctg cag gag gtg gag gag gga gag gct ccc ctg       336
Leu Glu Ala Cys Val Leu Gln Glu Val Glu Glu Gly Glu Ala Pro Leu
            100                 105                 110 acg aac gag gac att cat ccc gag gac tcc atc ctg agg aac tac ttc       384
Thr Asn Glu Asp Ile His Pro Glu Asp Ser Ile Leu Arg Asn Tyr Phe
        115                 120                 125 caa aga ctc tcc ctc tac ctg caa gag aag aaa tac agc cct tgt gcc       432
Gln Arg Leu Ser Leu Tyr Leu Gln Glu Lys Lys Tyr Ser Pro Cys Ala
    130                 135                 140 tgg gag atc gtc aga gca gaa atc atg aga tcc ttg tat tat tca tca       480
Trp Glu Ile Val Arg Ala Glu Ile Met Arg Ser Leu Tyr Tyr Ser Ser
145                 150                 155                 160 aca gcc ttg cag aaa aga tta agg agc gag aaa tga                       516
Thr Ala Leu Gln Lys Arg Leu Arg Ser Glu Lys
                165                 170

<210> SEQ ID NO 6
<211> LENGTH: 171
<212> TYPE: PRT
<213> ORGANISM: Felis catus

<400> SEQUENCE: 6

Cys Asp Leu Pro Gln Thr His Gly Leu Leu Asn Arg Arg Ala Leu Thr
1               5                   10                  15

Leu Leu Gly Gln Met Arg Arg Leu Pro Ala Ser Ser Cys Gln Lys Asp
            20                  25                  30

Arg Asn Asp Phe Ala Phe Pro Gln Asp Val Phe Gly Gly Gly Gln Ser
        35                  40                  45

His Lys Ala Gln Ala Leu Ser Val Val His Val Thr Asn Gln Lys Ile
    50                  55                  60

Phe His Phe Phe Cys Thr Glu Ala Ser Ser Ser Ala Ala Trp Asn Thr
65                  70                  75                  80

Thr Leu Leu Glu Glu Phe Cys Thr Gly Leu Asp Arg Gln Leu Thr Arg
                85                  90                  95

Leu Glu Ala Cys Val Leu Gln Glu Val Glu Glu Gly Glu Ala Pro Leu
            100                 105                 110

Thr Asn Glu Asp Ile His Pro Glu Asp Ser Ile Leu Arg Asn Tyr Phe
```

```
                    115                 120                 125
Gln Arg Leu Ser Leu Tyr Leu Gln Glu Lys Lys Tyr Ser Pro Cys Ala
        130                 135                 140

Trp Glu Ile Val Arg Ala Glu Ile Met Arg Ser Leu Tyr Tyr Ser Ser
145                 150                 155                 160

Thr Ala Leu Gln Lys Arg Leu Arg Ser Glu Lys
            165                 170

<210> SEQ ID NO 7
<211> LENGTH: 516
<212> TYPE: DNA
<213> ORGANISM: Felis catus
<220> FEATURE:
<221> NAME/KEY: CDS
<222> LOCATION: (1)..(513)

<400> SEQUENCE: 7 tgt gac ctg cct cag acc cac gtc ctg ctg aac agg agg gcc ttg acg    48
Cys Asp Leu Pro Gln Thr His Val Leu Leu Asn Arg Arg Ala Leu Thr
1               5                   10                  15 ctc ctg gga caa atg agg aga ctc cct gcc agc tcc tgt cag aag gac    96
Leu Leu Gly Gln Met Arg Arg Leu Pro Ala Ser Ser Cys Gln Lys Asp
            20                  25                  30 aga aat gac ttc gcc ttc ccc cag gac gtg ttc ggt gga gac cag tcc    144
Arg Asn Asp Phe Ala Phe Pro Gln Asp Val Phe Gly Gly Asp Gln Ser
        35                  40                  45 cac aag gcc caa gcc ctc tcg gtg gtg cac gtg acg aac cag aag atc    192
His Lys Ala Gln Ala Leu Ser Val Val His Val Thr Asn Gln Lys Ile
    50                  55                  60 ttc cac ttc ttc tgc aca gag gcg tcc tcg tct gct gct tgg aac acc    240
Phe His Phe Phe Cys Thr Glu Ala Ser Ser Ser Ala Ala Trp Asn Thr
65                  70                  75                  80 acc ctc ctg gag gaa ttt tgc acg gga ctt gat cgg cag ctg acc cgc    288
Thr Leu Leu Glu Glu Phe Cys Thr Gly Leu Asp Arg Gln Leu Thr Arg
                85                  90                  95 ctg gaa gcc tgt gtc ccg cag gag gtg gag gag gga gag gct ccc ctg    336
Leu Glu Ala Cys Val Pro Gln Glu Val Glu Glu Gly Glu Ala Pro Leu
            100                 105                 110 acg aac gag gac att cat ccc gag gac tcc atc ctg agg aac tac ttc    384
Thr Asn Glu Asp Ile His Pro Glu Asp Ser Ile Leu Arg Asn Tyr Phe
        115                 120                 125 caa aga ctc tcc ctc tac ctg caa gag aag aaa tac agc cct tgt gcc    432
Gln Arg Leu Ser Leu Tyr Leu Gln Glu Lys Lys Tyr Ser Pro Cys Ala
    130                 135                 140 tgg gag atc gtc aga gca gaa atc atg aga tcc ttg tat tat tca tca    480
Trp Glu Ile Val Arg Ala Glu Ile Met Arg Ser Leu Tyr Tyr Ser Ser
145                 150                 155                 160 aca gcc ttg cag aaa aga tta agg agc gag aaa tga                    516
Thr Ala Leu Gln Lys Arg Leu Arg Ser Glu Lys
                165                 170

<210> SEQ ID NO 8
<211> LENGTH: 171
<212> TYPE: PRT
<213> ORGANISM: Felis catus

<400> SEQUENCE: 8

Cys Asp Leu Pro Gln Thr His Val Leu Leu Asn Arg Arg Ala Leu Thr
1               5                   10                  15

Leu Leu Gly Gln Met Arg Arg Leu Pro Ala Ser Ser Cys Gln Lys Asp
            20                  25                  30
```

```
Arg Asn Asp Phe Ala Phe Pro Gln Asp Val Phe Gly Gly Asp Gln Ser
         35                  40                  45

His Lys Ala Gln Ala Leu Ser Val Val His Val Thr Asn Gln Lys Ile
 50                  55                  60

Phe His Phe Phe Cys Thr Glu Ala Ser Ser Ala Ala Trp Asn Thr
65                  70                  75                  80

Thr Leu Leu Glu Glu Phe Cys Thr Gly Leu Asp Arg Gln Leu Thr Arg
                 85                  90                  95

Leu Glu Ala Cys Val Pro Gln Glu Val Glu Glu Gly Glu Ala Pro Leu
             100                 105                 110

Thr Asn Glu Asp Ile His Pro Glu Asp Ser Ile Leu Arg Asn Tyr Phe
         115                 120                 125

Gln Arg Leu Ser Leu Tyr Leu Gln Glu Lys Lys Tyr Ser Pro Cys Ala
130                 135                 140

Trp Glu Ile Val Arg Ala Glu Ile Met Arg Ser Leu Tyr Tyr Ser Ser
145                 150                 155                 160

Thr Ala Leu Gln Lys Arg Leu Arg Ser Glu Lys
                 165                 170

<210> SEQ ID NO 9
<211> LENGTH: 516
<212> TYPE: DNA
<213> ORGANISM: Felis catus
<220> FEATURE:
<221> NAME/KEY: CDS
<222> LOCATION: (1)..(513)

<400> SEQUENCE: 9 tgt gac ctg cct cag acc cac ggc ctg ctg aac agg agg gcc ttg acg      48
Cys Asp Leu Pro Gln Thr His Gly Leu Leu Asn Arg Arg Ala Leu Thr
 1               5                  10                  15 ctc ctg gga caa atg agg aga ctc cct gcc agc tcc tgt cag aag gac      96
Leu Leu Gly Gln Met Arg Arg Leu Pro Ala Ser Ser Cys Gln Lys Asp
             20                  25                  30 aga aat gac ttc gcc ttc ccc cag gac gtg ttc ggt gga gac cag tcc     144
Arg Asn Asp Phe Ala Phe Pro Gln Asp Val Phe Gly Gly Asp Gln Ser
         35                  40                  45 cac aag gcc caa gcc ctc tcg gtg gtc cac gtg acg aac cag aag atc     192
His Lys Ala Gln Ala Leu Ser Val Val His Val Thr Asn Gln Lys Ile
 50                  55                  60 ttc cac ttc ttc tgc aca gag gcg tcc tcg tct gct gct tgg aac acc     240
Phe His Phe Phe Cys Thr Glu Ala Ser Ser Ser Ala Ala Trp Asn Thr
65                  70                  75                  80 acc ctc ctg gag gaa ttt tgc acg gga ctt gat cgg cag ctg acc cgc     288
Thr Leu Leu Glu Glu Phe Cys Thr Gly Leu Asp Arg Gln Leu Thr Arg
                 85                  90                  95 ctg gaa gcc tgt gtc ctg cag gag gtg gag gag gga gag gct ccc ctg     336
Leu Glu Ala Cys Val Leu Gln Glu Val Glu Glu Gly Glu Ala Pro Leu
             100                 105                 110 acg aac gag gac att cat ccc gag gac tcc atc ctg agg aac tac ttc     384
Thr Asn Glu Asp Ile His Pro Glu Asp Ser Ile Leu Arg Asn Tyr Phe
         115                 120                 125 caa aga ctc tcc ctc tac ctg caa gag aag aaa tac agc cct tgt gcc     432
Gln Arg Leu Ser Leu Tyr Leu Gln Glu Lys Lys Tyr Ser Pro Cys Ala
130                 135                 140 tgg gag atc gtc aga gca gaa atc atg aga tcc ttg tat tat tca tca     480
Trp Glu Ile Val Arg Ala Glu Ile Met Arg Ser Leu Tyr Tyr Ser Ser
145                 150                 155                 160
```

```
aca gcc ttg cag aaa aga tta agg agc gag aaa tga                    516
Thr Ala Leu Gln Lys Arg Leu Arg Ser Glu Lys
            165                 170

<210> SEQ ID NO 10
<211> LENGTH: 171
<212> TYPE: PRT
<213> ORGANISM: Felis catus

<400> SEQUENCE: 10

Cys Asp Leu Pro Gln Thr His Gly Leu Leu Asn Arg Arg Ala Leu Thr
1               5                   10                  15

Leu Leu Gly Gln Met Arg Arg Leu Pro Ala Ser Ser Cys Gln Lys Asp
            20                  25                  30

Arg Asn Asp Phe Ala Phe Pro Gln Asp Val Phe Gly Gly Asp Gln Ser
        35                  40                  45

His Lys Ala Gln Ala Leu Ser Val Val His Val Thr Asn Gln Lys Ile
    50                  55                  60

Phe His Phe Phe Cys Thr Glu Ala Ser Ser Ala Ala Trp Asn Thr
65                  70                  75                  80

Thr Leu Leu Glu Glu Phe Cys Thr Gly Leu Asp Arg Gln Leu Thr Arg
                85                  90                  95

Leu Glu Ala Cys Val Leu Gln Glu Val Glu Glu Gly Glu Ala Pro Leu
            100                 105                 110

Thr Asn Glu Asp Ile His Pro Glu Asp Ser Ile Leu Arg Asn Tyr Phe
        115                 120                 125

Gln Arg Leu Ser Leu Tyr Leu Gln Glu Lys Lys Tyr Ser Pro Cys Ala
    130                 135                 140

Trp Glu Ile Val Arg Ala Glu Ile Met Arg Ser Leu Tyr Tyr Ser Ser
145                 150                 155                 160

Thr Ala Leu Gln Lys Arg Leu Arg Ser Glu Lys
            165                 170

<210> SEQ ID NO 11
<211> LENGTH: 516
<212> TYPE: DNA
<213> ORGANISM: Felis catus
<220> FEATURE:
<221> NAME/KEY: CDS
<222> LOCATION: (1)..(513)

<400> SEQUENCE: 11 tgt gac ctg cct cag acc cac ggc ctg ctg aac agg agg gcc ttg acg    48
Cys Asp Leu Pro Gln Thr His Gly Leu Leu Asn Arg Arg Ala Leu Thr
1               5                   10                  15 ctc ctg gga caa atg agg aga ctc cct gcc agc tcc tgt cag aag gac    96
Leu Leu Gly Gln Met Arg Arg Leu Pro Ala Ser Ser Cys Gln Lys Asp
            20                  25                  30 aga aat gac ttc gcc ttc ccc cag gac gtg ttc ggt gga gac cag tcc   144
Arg Asn Asp Phe Ala Phe Pro Gln Asp Val Phe Gly Gly Asp Gln Ser
        35                  40                  45 cac aag gcc caa gcc ctc tcg gtg gtg cac gtg acg aac cag aag atc   192
His Lys Ala Gln Ala Leu Ser Val Val His Val Thr Asn Gln Lys Ile
    50                  55                  60 ttc cac ttc ttc tgc aca gag gcg tcc tcg tct gct gct tgg aac acc   240
Phe His Phe Phe Cys Thr Glu Ala Ser Ser Ser Ala Ala Trp Asn Thr
65                  70                  75                  80 acc ctc ctg gag gaa ttc tgc acg gga ctt gat cgg cag ctg acc cgc   288
Thr Leu Leu Glu Glu Phe Cys Thr Gly Leu Asp Arg Gln Leu Thr Arg
                85                  90                  95
```

```
ctg gaa gcc tgt gtc ctg cag gag gtg gag gag gga gag gct ccc ctg    336
Leu Glu Ala Cys Val Leu Gln Glu Val Glu Glu Gly Glu Ala Pro Leu
        100                 105                 110 acg aac gag gac att cat ccc gag gac tcc atc ctg agg aac tac ttc    384
Thr Asn Glu Asp Ile His Pro Glu Asp Ser Ile Leu Arg Asn Tyr Phe
            115                 120                 125 caa aga ctc tcc ctc tac ctg caa gag aag aaa tac agc cct tgt gcc    432
Gln Arg Leu Ser Leu Tyr Leu Gln Glu Lys Lys Tyr Ser Pro Cys Ala
    130                 135                 140 tgg gag atc gtc aga gca gaa atc atg aga tcc ttg tat tat tca tca    480
Trp Glu Ile Val Arg Ala Glu Ile Met Arg Ser Leu Tyr Tyr Ser Ser
145                 150                 155                 160 aca gcc ttg cag aaa aga tta agg agc gag aaa tga                    516
Thr Ala Leu Gln Lys Arg Leu Arg Ser Glu Lys
                165                 170

<210> SEQ ID NO 12
<211> LENGTH: 171
<212> TYPE: PRT
<213> ORGANISM: Felis catus

<400> SEQUENCE: 12

Cys Asp Leu Pro Gln Thr His Gly Leu Leu Asn Arg Arg Ala Leu Thr
1               5                   10                  15

Leu Leu Gly Gln Met Arg Arg Leu Pro Ala Ser Ser Cys Gln Lys Asp
            20                  25                  30

Arg Asn Asp Phe Ala Phe Pro Gln Asp Val Phe Gly Gly Asp Gln Ser
        35                  40                  45

His Lys Ala Gln Ala Leu Ser Val Val His Val Thr Asn Gln Lys Ile
    50                  55                  60

Phe His Phe Phe Cys Thr Glu Ala Ser Ser Ala Ala Trp Asn Thr
65                  70                  75                  80

Thr Leu Leu Glu Glu Phe Cys Thr Gly Leu Asp Arg Gln Leu Thr Arg
                85                  90                  95

Leu Glu Ala Cys Val Leu Gln Glu Val Glu Glu Gly Glu Ala Pro Leu
            100                 105                 110

Thr Asn Glu Asp Ile His Pro Glu Asp Ser Ile Leu Arg Asn Tyr Phe
        115                 120                 125

Gln Arg Leu Ser Leu Tyr Leu Gln Glu Lys Lys Tyr Ser Pro Cys Ala
    130                 135                 140

Trp Glu Ile Val Arg Ala Glu Ile Met Arg Ser Leu Tyr Tyr Ser Ser
145                 150                 155                 160

Thr Ala Leu Gln Lys Arg Leu Arg Ser Glu Lys
                165                 170

<210> SEQ ID NO 13
<211> LENGTH: 516
<212> TYPE: DNA
<213> ORGANISM: Felis catus
<220> FEATURE:
<221> NAME/KEY: CDS
<222> LOCATION: (1)..(513)

<400> SEQUENCE: 13 tgt gac ctg cct cag acc cac ggc ctg ctg aac agg agg gcc ttg acg    48
Cys Asp Leu Pro Gln Thr His Gly Leu Leu Asn Arg Arg Ala Leu Thr
1               5                   10                  15 ctc ctg gga caa atg agg aga ctc cct gcc agc tcc tgt cag aag gac    96
Leu Leu Gly Gln Met Arg Arg Leu Pro Ala Ser Ser Cys Gln Lys Asp
```

```
                    20                  25                  30
aga aat gac ttc gcc ttc ccc cag gac gtg ttc ggt gga gac cag tcc      144
Arg Asn Asp Phe Ala Phe Pro Gln Asp Val Phe Gly Gly Asp Gln Ser
        35                  40                  45 cac aag gcc caa gcc ctc tcg gtg gtg cac gtg acg aac cag aag atc      192
His Lys Ala Gln Ala Leu Ser Val Val His Val Thr Asn Gln Lys Ile
 50                  55                  60 ttc cac ttc ttc tgc aca gag gcg tcc tcg tct gct gct tgg aat acc      240
Phe His Phe Phe Cys Thr Glu Ala Ser Ser Ser Ala Ala Trp Asn Thr
 65                  70                  75                  80 acc ctc ctg gag gaa ttt tgc acg gga ctt gat cgg cag ctg acc cgc      288
Thr Leu Leu Glu Glu Phe Cys Thr Gly Leu Asp Arg Gln Leu Thr Arg
                 85                  90                  95 ctg gaa gcc tgt gtc ctg cag gag gtg gag gag gga gag gct ccc ctg      336
Leu Glu Ala Cys Val Leu Gln Glu Val Glu Glu Gly Glu Ala Pro Leu
            100                 105                 110 acg aac gag gac att cat ccc gag gac tcc atc ctg agg aac tac ttc      384
Thr Asn Glu Asp Ile His Pro Glu Asp Ser Ile Leu Arg Asn Tyr Phe
        115                 120                 125 caa aga ctc tcc ctc tac ctg caa gag aag aaa tac agc cct tgt gcc      432
Gln Arg Leu Ser Leu Tyr Leu Gln Glu Lys Lys Tyr Ser Pro Cys Ala
    130                 135                 140 tgg gag atc gtc aga gca gaa atc atg aga tcc ttg tat tat tca tca      480
Trp Glu Ile Val Arg Ala Glu Ile Met Arg Ser Leu Tyr Tyr Ser Ser
145                 150                 155                 160 aca gcc ttg cag aaa aga tta agg agc gag aaa tga                       516
Thr Ala Leu Gln Lys Arg Leu Arg Ser Glu Lys
                165                 170

<210> SEQ ID NO 14
<211> LENGTH: 171
<212> TYPE: PRT
<213> ORGANISM: Felis catus

<400> SEQUENCE: 14

Cys Asp Leu Pro Gln Thr His Gly Leu Leu Asn Arg Arg Ala Leu Thr
1               5                   10                  15

Leu Leu Gly Gln Met Arg Arg Leu Pro Ala Ser Ser Cys Gln Lys Asp
            20                  25                  30

Arg Asn Asp Phe Ala Phe Pro Gln Asp Val Phe Gly Gly Asp Gln Ser
        35                  40                  45

His Lys Ala Gln Ala Leu Ser Val Val His Val Thr Asn Gln Lys Ile
 50                  55                  60

Phe His Phe Phe Cys Thr Glu Ala Ser Ser Ser Ala Ala Trp Asn Thr
 65                  70                  75                  80

Thr Leu Leu Glu Glu Phe Cys Thr Gly Leu Asp Arg Gln Leu Thr Arg
                 85                  90                  95

Leu Glu Ala Cys Val Leu Gln Glu Val Glu Glu Gly Glu Ala Pro Leu
            100                 105                 110

Thr Asn Glu Asp Ile His Pro Glu Asp Ser Ile Leu Arg Asn Tyr Phe
        115                 120                 125

Gln Arg Leu Ser Leu Tyr Leu Gln Glu Lys Lys Tyr Ser Pro Cys Ala
    130                 135                 140

Trp Glu Ile Val Arg Ala Glu Ile Met Arg Ser Leu Tyr Tyr Ser Ser
145                 150                 155                 160

Thr Ala Leu Gln Lys Arg Leu Arg Ser Glu Lys
                165                 170
```

<210> SEQ ID NO 15
<211> LENGTH: 516
<212> TYPE: DNA
<213> ORGANISM: Felis catus
<220> FEATURE:
<221> NAME/KEY: CDS
<222> LOCATION: (1)..(513)

<400> SEQUENCE: 15

```
tgt gac ctg cct cag acc cac gtc ctg ctg aac agg agg gcc ttg acg        48
Cys Asp Leu Pro Gln Thr His Val Leu Leu Asn Arg Arg Ala Leu Thr
1               5                   10                  15 ctc ctg gga caa atg agg aga ctc cct gcc agc tcc tgt cag aag gac        96
Leu Leu Gly Gln Met Arg Arg Leu Pro Ala Ser Ser Cys Gln Lys Asp
            20                  25                  30 aga aat gac ttc gcc ttc ccc cag gac gtg ttc ggt gga gac cag tcc       144
Arg Asn Asp Phe Ala Phe Pro Gln Asp Val Phe Gly Gly Asp Gln Ser
        35                  40                  45 cac aag gcc caa gcc ctc tcg gtg gtg cac gtg acg aac cag aag atc       192
His Lys Ala Gln Ala Leu Ser Val Val His Val Thr Asn Gln Lys Ile
    50                  55                  60 ttc cac ttc ttc tgc aca gag gcg tcc tcg tct gct gct tgg aac acc       240
Phe His Phe Phe Cys Thr Glu Ala Ser Ser Ser Ala Ala Trp Asn Thr
65                  70                  75                  80 acc ctc ctg gag gaa ttt tgc acg gga ctt gat cgg cag ctg acc cgc       288
Thr Leu Leu Glu Glu Phe Cys Thr Gly Leu Asp Arg Gln Leu Thr Arg
                85                  90                  95 ctg gaa gcc tgt gtc ctg cag gag gtg gag gag gga gag gct ccc ctg       336
Leu Glu Ala Cys Val Leu Gln Glu Val Glu Glu Gly Glu Ala Pro Leu
            100                 105                 110 acg aac gag gac att cat ccc gag gac tcc atc ctg agg aac tac ttc       384
Thr Asn Glu Asp Ile His Pro Glu Asp Ser Ile Leu Arg Asn Tyr Phe
        115                 120                 125 caa aga ctc tcc ctc tac ctg caa gag aag aaa tac agc cct tgt gcc       432
Gln Arg Leu Ser Leu Tyr Leu Gln Glu Lys Lys Tyr Ser Pro Cys Ala
    130                 135                 140 tgg gag atc gtc aga gca gaa atc atg aga tcc ttg tat tat tca tca       480
Trp Glu Ile Val Arg Ala Glu Ile Met Arg Ser Leu Tyr Tyr Ser Ser
145                 150                 155                 160 aca gcc ttg cag aaa aga tta agg agc gag aaa tga                       516
Thr Ala Leu Gln Lys Arg Leu Arg Ser Glu Lys
                165                 170
```

<210> SEQ ID NO 16
<211> LENGTH: 171
<212> TYPE: PRT
<213> ORGANISM: Felis catus

<400> SEQUENCE: 16

```
Cys Asp Leu Pro Gln Thr His Val Leu Leu Asn Arg Arg Ala Leu Thr
1               5                   10                  15

Leu Leu Gly Gln Met Arg Arg Leu Pro Ala Ser Ser Cys Gln Lys Asp
            20                  25                  30

Arg Asn Asp Phe Ala Phe Pro Gln Asp Val Phe Gly Gly Asp Gln Ser
        35                  40                  45

His Lys Ala Gln Ala Leu Ser Val Val His Val Thr Asn Gln Lys Ile
    50                  55                  60

Phe His Phe Phe Cys Thr Glu Ala Ser Ser Ser Ala Ala Trp Asn Thr
65                  70                  75                  80

Thr Leu Leu Glu Glu Phe Cys Thr Gly Leu Asp Arg Gln Leu Thr Arg
```

```
                     85                  90                  95
Leu Glu Ala Cys Val Leu Gln Glu Val Glu Gly Glu Ala Pro Leu
            100                 105                 110

Thr Asn Glu Asp Ile His Pro Glu Asp Ser Ile Leu Arg Asn Tyr Phe
            115                 120                 125

Gln Arg Leu Ser Leu Tyr Leu Gln Glu Lys Lys Tyr Ser Pro Cys Ala
        130                 135                 140

Trp Glu Ile Val Arg Ala Glu Ile Met Arg Ser Leu Tyr Tyr Ser Ser
145                 150                 155                 160

Thr Ala Leu Gln Lys Arg Leu Arg Ser Glu Lys
            165                 170

<210> SEQ ID NO 17
<211> LENGTH: 501
<212> TYPE: DNA
<213> ORGANISM: Felis catus
<220> FEATURE:
<221> NAME/KEY: CDS
<222> LOCATION: (1)..(498)

<400> SEQUENCE: 17 tgt gac ctg cct cag acc cac gtc ctg ctg aac agg agg gcc ttg acg     48
Cys Asp Leu Pro Gln Thr His Val Leu Leu Asn Arg Arg Ala Leu Thr
1               5                   10                  15 ctc ctg gga caa atg agg aga ctc cct gcc agc tcc tgt cag aag gac     96
Leu Leu Gly Gln Met Arg Arg Leu Pro Ala Ser Ser Cys Gln Lys Asp
            20                  25                  30 aga aat gac ttc gcc ttc ccc cag gac gtg ttc ggt gga gac cag tcc    144
Arg Asn Asp Phe Ala Phe Pro Gln Asp Val Phe Gly Gly Asp Gln Ser
        35                  40                  45 cac aag gcc caa gcc ctc tcg gtg gtg cac gtg acg aac cag aag atc    192
His Lys Ala Gln Ala Leu Ser Val Val His Val Thr Asn Gln Lys Ile
    50                  55                  60 ttc cac ttc ttc tgc aca gag gcg tcc tcg tct gct gct tgg aac acc    240
Phe His Phe Phe Cys Thr Glu Ala Ser Ser Ser Ala Ala Trp Asn Thr
65                  70                  75                  80 acc ctc ctg gag gaa ttc tgc acg gga ctt gat cgg cag ctg acc cgc    288
Thr Leu Leu Glu Glu Phe Cys Thr Gly Leu Asp Arg Gln Leu Thr Arg
                85                  90                  95 ctg gaa gcc tgt gtc gtg cag gag gtg ggg gag gga gag gct ccc ctc    336
Leu Glu Ala Cys Val Val Gln Glu Val Gly Glu Gly Glu Ala Pro Leu
            100                 105                 110 acg aac gag gac tcc atc ctg agg aac tac ttc caa aga ctc tcc ctc    384
Thr Asn Glu Asp Ser Ile Leu Arg Asn Tyr Phe Gln Arg Leu Ser Leu
        115                 120                 125 tac ctg caa gag aag aaa tac agc cct tgt gcc tgg gag atc gtc aga    432
Tyr Leu Gln Glu Lys Lys Tyr Ser Pro Cys Ala Trp Glu Ile Val Arg
    130                 135                 140 gca gaa atc atg aga tcc ttg tat tat tca tca aca gcc ttg cag aaa    480
Ala Glu Ile Met Arg Ser Leu Tyr Tyr Ser Ser Thr Ala Leu Gln Lys
145                 150                 155                 160 aga tta agg agc gag aaa tga                                        501
Arg Leu Arg Ser Glu Lys
                165

<210> SEQ ID NO 18
<211> LENGTH: 166
<212> TYPE: PRT
<213> ORGANISM: Felis catus

<400> SEQUENCE: 18
```

```
Cys Asp Leu Pro Gln Thr His Val Leu Leu Asn Arg Arg Ala Leu Thr
1               5                   10                  15

Leu Leu Gly Gln Met Arg Arg Leu Pro Ala Ser Ser Cys Gln Lys Asp
            20                  25                  30

Arg Asn Asp Phe Ala Phe Pro Gln Asp Val Phe Gly Gly Asp Gln Ser
        35                  40                  45

His Lys Ala Gln Ala Leu Ser Val Val His Val Thr Asn Gln Lys Ile
    50                  55                  60

Phe His Phe Phe Cys Thr Glu Ala Ser Ser Ala Ala Trp Asn Thr
65                  70                  75                  80

Thr Leu Leu Glu Glu Phe Cys Thr Gly Leu Asp Arg Gln Leu Thr Arg
                85                  90                  95

Leu Glu Ala Cys Val Val Gln Glu Val Gly Gly Glu Ala Pro Leu
                100                 105                 110

Thr Asn Glu Asp Ser Ile Leu Arg Asn Tyr Phe Gln Arg Leu Ser Leu
            115                 120                 125

Tyr Leu Gln Glu Lys Lys Tyr Ser Pro Cys Ala Trp Glu Ile Val Arg
    130                 135                 140

Ala Glu Ile Met Arg Ser Leu Tyr Tyr Ser Ser Thr Ala Leu Gln Lys
145                 150                 155                 160

Arg Leu Arg Ser Glu Lys
                165

<210> SEQ ID NO 19
<211> LENGTH: 516
<212> TYPE: DNA
<213> ORGANISM: Felis catus
<220> FEATURE:
<221> NAME/KEY: CDS
<222> LOCATION: (1)..(513)

<400> SEQUENCE: 19 tgt gac ctg cct cag acc cac ggc ctg ctg aac agg agg gcc ttg acg      48
Cys Asp Leu Pro Gln Thr His Gly Leu Leu Asn Arg Arg Ala Leu Thr
1               5                   10                  15 ctc ctg gga caa atg agg aga ctc cct gcc agc tcc tgt cag aag gac      96
Leu Leu Gly Gln Met Arg Arg Leu Pro Ala Ser Ser Cys Gln Lys Asp
            20                  25                  30 aga aat gac ttc gcc ttc ccc cag gac gtg ttc ggt gga ggc cag tcc     144
Arg Asn Asp Phe Ala Phe Pro Gln Asp Val Phe Gly Gly Gly Gln Ser
        35                  40                  45 cac aag gcc caa gcc ctc tcg gtg gtg cac gtg acg aac cag aag atc     192
His Lys Ala Gln Ala Leu Ser Val Val His Val Thr Asn Gln Lys Ile
    50                  55                  60 ttc cac ttc ttc tgc aca gag gcg tcc tcc tct gct gct tgg aac acc     240
Phe His Phe Phe Cys Thr Glu Ala Ser Ser Ser Ala Ala Trp Asn Thr
65                  70                  75                  80 acc ctc ctg gag gaa ttt tgc acg gga ctt gat cgg cag ctg acc cgc     288
Thr Leu Leu Glu Glu Phe Cys Thr Gly Leu Asp Arg Gln Leu Thr Arg
                85                  90                  95 ctg gaa gcc tgt gtc ctg cag gag gtg gag gag gga gag gct ccc ctg     336
Leu Glu Ala Cys Val Leu Gln Glu Val Glu Glu Gly Glu Ala Pro Leu
                100                 105                 110 acg aac gag gac att cat ccc gag gac tcc atc ctg agg aac tac ttc     384
Thr Asn Glu Asp Ile His Pro Glu Asp Ser Ile Leu Arg Asn Tyr Phe
            115                 120                 125 caa aga ctc tcc ctc tac ctg caa gag aag aaa tac agc cct tgt gcc     432
Gln Arg Leu Ser Leu Tyr Leu Gln Glu Lys Lys Tyr Ser Pro Cys Ala
```

```
     130                 135                 140
tgg gag atc gtc aga gca gaa atc atg aga tcc ttg tat tat tca tca    480
Trp Glu Ile Val Arg Ala Glu Ile Met Arg Ser Leu Tyr Tyr Ser Ser
145                 150                 155                 160 aca gcc ttg cag aaa aga tta agg agc gag aaa tga                    516
Thr Ala Leu Gln Lys Arg Leu Arg Ser Glu Lys
                165                 170

<210> SEQ ID NO 21
<211> LENGTH: 171
<212> TYPE: PRT
<213> ORGANISM: Felis catus

<400> SEQUENCE: 20

Cys Asp Leu Pro Gln Thr His Gly Leu Leu Asn Arg Arg Ala Leu Thr
1               5                   10                  15

Leu Leu Gly Gln Met Arg Arg Leu Pro Ala Ser Ser Cys Gln Lys Asp
            20                  25                  30

Arg Asn Asp Phe Ala Phe Pro Gln Asp Val Phe Gly Gly Gly Gln Ser
        35                  40                  45

His Lys Ala Gln Ala Leu Ser Val Val His Val Thr Asn Gln Lys Ile
    50                  55                  60

Phe His Phe Phe Cys Thr Glu Ala Ser Ser Ala Ala Trp Asn Thr
65                  70                  75                  80

Thr Leu Leu Glu Glu Phe Cys Thr Gly Leu Asp Arg Gln Leu Thr Arg
                85                  90                  95

Leu Glu Ala Cys Val Leu Gln Glu Val Glu Gly Glu Ala Pro Leu
            100                 105                 110

Thr Asn Glu Asp Ile His Pro Glu Asp Ser Ile Leu Arg Asn Tyr Phe
        115                 120                 125

Gln Arg Leu Ser Leu Tyr Leu Gln Glu Lys Lys Tyr Ser Pro Cys Ala
    130                 135                 140

Trp Glu Ile Val Arg Ala Glu Ile Met Arg Ser Leu Tyr Tyr Ser Ser
145                 150                 155                 160

Thr Ala Leu Gln Lys Arg Leu Arg Ser Glu Lys
                165                 170

<210> SEQ ID NO 21
<211> LENGTH: 516
<212> TYPE: DNA
<213> ORGANISM: Felis catus
<220> FEATURE:
<221> NAME/KEY: CDS
<222> LOCATION: (1)..(513)

<400> SEQUENCE: 21 tgt gac ctg cct cag acc cac gtc ctg ctg aac agg agg gcc ttg acg    48
Cys Asp Leu Pro Gln Thr His Val Leu Leu Asn Arg Arg Ala Leu Thr
1               5                   10                  15 ctc ctg gga caa atg agg aga ctc cct gcc agc tcc tgt cag aag gac    96
Leu Leu Gly Gln Met Arg Arg Leu Pro Ala Ser Ser Cys Gln Lys Asp
            20                  25                  30 aga aat gac ttc gcc ttc ccc cag gac gtg ttc ggt gga gac cag tcc    144
Arg Asn Asp Phe Ala Phe Pro Gln Asp Val Phe Gly Gly Asp Gln Ser
        35                  40                  45 cac aag gcc caa gcc ctc tcg gtg gtg cac gtg acg aac cag aag atc    192
His Lys Ala Gln Ala Leu Ser Val Val His Val Thr Asn Gln Lys Ile
    50                  55                  60 ttc cac ttc ttc tgc aca gag gcg tcc tcg tct gct gct tgg aac acc    240
```

```
Phe His Phe Phe Cys Thr Glu Ala Ser Ser Ala Ala Trp Asn Thr
 65                  70                  75                  80 acc ctc ctg gag gaa ttc tgc acg gga ctt gat cgg cag ctg acc cgc    288
Thr Leu Leu Glu Glu Phe Cys Thr Gly Leu Asp Arg Gln Leu Thr Arg
                 85                  90                  95 ctg gaa gcc tgt gtc ctg cag gag gtg gag gag gga gag gct ccc ctg    336
Leu Glu Ala Cys Val Leu Gln Glu Val Glu Glu Gly Glu Ala Pro Leu
            100                 105                 110 acg aac gag gac att cat ccc gag gac tcc atc ctg agg aac tac ttc    384
Thr Asn Glu Asp Ile His Pro Glu Asp Ser Ile Leu Arg Asn Tyr Phe
        115                 120                 125 caa aga ctc tcc ctc tac ctg caa gag aag aaa tac agc cct tgt gcc    432
Gln Arg Leu Ser Leu Tyr Leu Gln Glu Lys Lys Tyr Ser Pro Cys Ala
    130                 135                 140 tgg gag atc gtc aga gca gaa atc atg aga tcc ttg tat tat tca tca    480
Trp Glu Ile Val Arg Ala Glu Ile Met Arg Ser Leu Tyr Tyr Ser Ser
145                 150                 155                 160 aca gcc ttg cag aaa aga tta agg agc gag aaa tga                    516
Thr Ala Leu Gln Lys Arg Leu Arg Ser Glu Lys
                165                 170
```

<210> SEQ ID NO 22
<211> LENGTH: 171
<212> TYPE: PRT
<213> ORGANISM: Felis catus

<400> SEQUENCE: 22

```
Cys Asp Leu Pro Gln Thr His Val Leu Leu Asn Arg Arg Ala Leu Thr
  1               5                  10                  15

Leu Leu Gly Gln Met Arg Arg Leu Pro Ala Ser Ser Cys Gln Lys Asp
             20                  25                  30

Arg Asn Asp Phe Ala Phe Pro Gln Asp Val Phe Gly Gly Asp Gln Ser
         35                  40                  45

His Lys Ala Gln Ala Leu Ser Val Val His Val Thr Asn Gln Lys Ile
     50                  55                  60

Phe His Phe Phe Cys Thr Glu Ala Ser Ser Ala Ala Trp Asn Thr
 65                  70                  75                  80

Thr Leu Leu Glu Glu Phe Cys Thr Gly Leu Asp Arg Gln Leu Thr Arg
                 85                  90                  95

Leu Glu Ala Cys Val Leu Gln Glu Val Glu Glu Gly Glu Ala Pro Leu
            100                 105                 110

Thr Asn Glu Asp Ile His Pro Glu Asp Ser Ile Leu Arg Asn Tyr Phe
        115                 120                 125

Gln Arg Leu Ser Leu Tyr Leu Gln Glu Lys Lys Tyr Ser Pro Cys Ala
    130                 135                 140

Trp Glu Ile Val Arg Ala Glu Ile Met Arg Ser Leu Tyr Tyr Ser Ser
145                 150                 155                 160

Thr Ala Leu Gln Lys Arg Leu Arg Ser Glu Lys
                165                 170
```

<210> SEQ ID NO 23
<211> LENGTH: 501
<212> TYPE: DNA
<213> ORGANISM: Felis catus
<220> FEATURE:
<221> NAME/KEY: CDS
<222> LOCATION: (1)..(498)

<400> SEQUENCE: 23

```
tgt gac ctg cct cag acc cac gtc ctg ctg aac agg agg gcc ttg acg    48
Cys Asp Leu Pro Gln Thr His Val Leu Leu Asn Arg Arg Ala Leu Thr
 1               5                  10                  15 ctc ctg gga caa atg agg aga ctc cct gcc agc tcc tgt cag aag gac    96
Leu Leu Gly Gln Met Arg Arg Leu Pro Ala Ser Ser Cys Gln Lys Asp
             20                  25                  30 aga aat gac tcc gcc ttc ccc cag gac gtg ttc ggt gga gac cag tcc   144
Arg Asn Asp Ser Ala Phe Pro Gln Asp Val Phe Gly Gly Asp Gln Ser
         35                  40                  45 cac aag gcc caa gcc ctc tcg gtg gtg cac gtg acg aac cag aag atc   192
His Lys Ala Gln Ala Leu Ser Val Val His Val Thr Asn Gln Lys Ile
     50                  55                  60 ttc cac ttc ttc tgc aca gag gcg tcc tcg tct gct gct tgg aac acc   240
Phe His Phe Phe Cys Thr Glu Ala Ser Ser Ser Ala Ala Trp Asn Thr
65                  70                  75                  80 acc ctc ctg gag gaa ttc tgc acg gga ctt gat cgg cag ctg acc cgc   288
Thr Leu Leu Glu Glu Phe Cys Thr Gly Leu Asp Arg Gln Leu Thr Arg
                 85                  90                  95 ctg gaa gcc tgt gtc ctg cag gag gtg ggg gag gga gag gct ccc ctc   336
Leu Glu Ala Cys Val Leu Gln Glu Val Gly Glu Gly Glu Ala Pro Leu
            100                 105                 110 acg aac gag gac tcc atc ctg agg aac tac ttc caa aga ctc tcc ctc   384
Thr Asn Glu Asp Ser Ile Leu Arg Asn Tyr Phe Gln Arg Leu Ser Leu
        115                 120                 125 tac ctg caa gag aag aaa tcc agc cct tgt gcc tgg gag atc gtc aga   432
Tyr Leu Gln Glu Lys Lys Ser Ser Pro Cys Ala Trp Glu Ile Val Arg
    130                 135                 140 gca gaa atc atg aga tcc ttg tat tat tca tca aca gcc ttg cag aaa   480
Ala Glu Ile Met Arg Ser Leu Tyr Tyr Ser Ser Thr Ala Leu Gln Lys
145                 150                 155                 160 aga tta agg agc gag aaa tga                                        501
Arg Leu Arg Ser Glu Lys
                165

<210> SEQ ID NO 24
<211> LENGTH: 166
<212> TYPE: PRT
<213> ORGANISM: Felis catus

<400> SEQUENCE: 24

Cys Asp Leu Pro Gln Thr His Val Leu Leu Asn Arg Arg Ala Leu Thr
 1               5                  10                  15

Leu Leu Gly Gln Met Arg Arg Leu Pro Ala Ser Ser Cys Gln Lys Asp
             20                  25                  30

Arg Asn Asp Ser Ala Phe Pro Gln Asp Val Phe Gly Gly Asp Gln Ser
         35                  40                  45

His Lys Ala Gln Ala Leu Ser Val Val His Val Thr Asn Gln Lys Ile
     50                  55                  60

Phe His Phe Phe Cys Thr Glu Ala Ser Ser Ser Ala Ala Trp Asn Thr
65                  70                  75                  80

Thr Leu Leu Glu Glu Phe Cys Thr Gly Leu Asp Arg Gln Leu Thr Arg
                 85                  90                  95

Leu Glu Ala Cys Val Leu Gln Glu Val Gly Glu Gly Glu Ala Pro Leu
            100                 105                 110

Thr Asn Glu Asp Ser Ile Leu Arg Asn Tyr Phe Gln Arg Leu Ser Leu
        115                 120                 125

Tyr Leu Gln Glu Lys Lys Ser Ser Pro Cys Ala Trp Glu Ile Val Arg
    130                 135                 140
```

```
Ala Glu Ile Met Arg Ser Leu Tyr Tyr Ser Ser Thr Ala Leu Gln Lys
145                 150                 155                 160

Arg Leu Arg Ser Glu Lys
                165

<210> SEQ ID NO 25
<211> LENGTH: 516
<212> TYPE: DNA
<213> ORGANISM: Felis catus
<220> FEATURE:
<221> NAME/KEY: CDS
<222> LOCATION: (1)..(513)

<400> SEQUENCE: 25 tgt gac ctg cct cag acc cac gtc ctg ctg aac agg agg gcc ttg acg      48
Cys Asp Leu Pro Gln Thr His Val Leu Leu Asn Arg Arg Ala Leu Thr
1               5                  10                  15 ctc ctg gga caa atg agg aga ctc cct gcc agc tcc tgt cag aag gac      96
Leu Leu Gly Gln Met Arg Arg Leu Pro Ala Ser Ser Cys Gln Lys Asp
            20                  25                  30 aga aat gac ttc gcc ttc ccc cag gac gtg ttc ggt gga gac cag tcc     144
Arg Asn Asp Phe Ala Phe Pro Gln Asp Val Phe Gly Gly Asp Gln Ser
        35                  40                  45 cac aag gcc caa gcc ctc tcg gtg gtg cac gtg acg aac cag aag atc     192
His Lys Ala Gln Ala Leu Ser Val Val His Val Thr Asn Gln Lys Ile
    50                  55                  60 ttc cac ttc ttc tgc aca gag gcg tcc tcg tct gct gct tgg aac acc     240
Phe His Phe Phe Cys Thr Glu Ala Ser Ser Ser Ala Ala Trp Asn Thr
65                  70                  75                  80 acc ctc ctg gag gaa ttt tgc acg gga ctt gat cgg cag ctg acc cgc     288
Thr Leu Leu Glu Glu Phe Cys Thr Gly Leu Asp Arg Gln Leu Thr Arg
                85                  90                  95 ctg gaa gcc tgt gtc ccg cag gag gtg gag gag gga gag gct ccc ctg     336
Leu Glu Ala Cys Val Pro Gln Glu Val Glu Glu Gly Glu Ala Pro Leu
            100                 105                 110 acg aac gag gac att cat ccc gag gac tcc atc ctg agg aac tac ttc     384
Thr Asn Glu Asp Ile His Pro Glu Asp Ser Ile Leu Arg Asn Tyr Phe
        115                 120                 125 caa aga ctc tcc ctc tac ctg caa gag aag aaa tac agc cct tgt gcc     432
Gln Arg Leu Ser Leu Tyr Leu Gln Glu Lys Lys Tyr Ser Pro Cys Ala
    130                 135                 140 tgg gag atc gtc aga gca gaa atc atg aga tcc ttg tat tat tca tca     480
Trp Glu Ile Val Arg Ala Glu Ile Met Arg Ser Leu Tyr Tyr Ser Ser
145                 150                 155                 160 aca gcc ttg cag aaa aga tta agg agc gag aaa tga                     516
Thr Ala Leu Gln Lys Arg Leu Arg Ser Glu Lys
                165                 170

<210> SEQ ID NO 26
<211> LENGTH: 171
<212> TYPE: PRT
<213> ORGANISM: Felis catus

<400> SEQUENCE: 26

Cys Asp Leu Pro Gln Thr His Val Leu Leu Asn Arg Arg Ala Leu Thr
1               5                  10                  15

Leu Leu Gly Gln Met Arg Arg Leu Pro Ala Ser Ser Cys Gln Lys Asp
            20                  25                  30

Arg Asn Asp Phe Ala Phe Pro Gln Asp Val Phe Gly Gly Asp Gln Ser
        35                  40                  45

His Lys Ala Gln Ala Leu Ser Val Val His Val Thr Asn Gln Lys Ile
```

```
                 50                  55                  60
Phe His Phe Phe Cys Thr Glu Ala Ser Ser Ala Ala Trp Asn Thr
 65                  70                  75                  80

Thr Leu Leu Glu Glu Phe Cys Thr Gly Leu Asp Arg Gln Leu Thr Arg
                     85                  90                  95

Leu Glu Ala Cys Val Pro Gln Glu Val Glu Gly Glu Ala Pro Leu
                100                 105                 110

Thr Asn Glu Asp Ile His Pro Glu Asp Ser Ile Leu Arg Asn Tyr Phe
                115                 120                 125

Gln Arg Leu Ser Leu Tyr Leu Gln Glu Lys Lys Tyr Ser Pro Cys Ala
        130                 135                 140

Trp Glu Ile Val Arg Ala Glu Ile Met Arg Ser Leu Tyr Tyr Ser Ser
145                 150                 155                 160

Thr Ala Leu Gln Lys Arg Leu Arg Ser Glu Lys
                165                 170

<210> SEQ ID NO 27
<211> LENGTH: 501
<212> TYPE: DNA
<213> ORGANISM: Macaca mulatta
<220> FEATURE:
<221> NAME/KEY: CDS
<222> LOCATION: (1)..(498)

<400> SEQUENCE: 27 tgt gat ctg cct gag acc cac agc ctg gat aac agg aag acc atg atg     48
Cys Asp Leu Pro Glu Thr His Ser Leu Asp Asn Arg Lys Thr Met Met
 1               5                  10                  15 ctc ctg gca cag atg agc aga atc tct cct tcc tcc tgt ctg atg gac     96
Leu Leu Ala Gln Met Ser Arg Ile Ser Pro Ser Ser Cys Leu Met Asp
                20                  25                  30 aga cat gac ttt gga ttt ccc cag cag gag ttt gat ggc aac cag ttc    144
Arg His Asp Phe Gly Phe Pro Gln Gln Glu Phe Asp Gly Asn Gln Phe
            35                  40                  45 cag aag gct cca gcc atc tct gtc ctc cat gag ctg atc cag cag acc    192
Gln Lys Ala Pro Ala Ile Ser Val Leu His Glu Leu Ile Gln Gln Thr
        50                  55                  60 ttc aac ctc ttt acc aca aaa gac tca tct gct gct tgg gat gag gac    240
Phe Asn Leu Phe Thr Thr Lys Asp Ser Ser Ala Ala Trp Asp Glu Asp
 65                  70                  75                  80 ctc cta gac aaa ttc tgc act gaa ctc tac cag cag ctg aat gac ttg    288
Leu Leu Asp Lys Phe Cys Thr Glu Leu Tyr Gln Gln Leu Asn Asp Leu
                 85                  90                  95 gaa gcc tgt gtc atg cag cag gag agg gtg gga gaa act ccc ctg atg    336
Glu Ala Cys Val Met Gln Gln Glu Arg Val Gly Glu Thr Pro Leu Met
                100                 105                 110 aat gcg gac tcc acc ttg gct gtg aag aaa tac ttc cga aga atc act    384
Asn Ala Asp Ser Thr Leu Ala Val Lys Lys Tyr Phe Arg Arg Ile Thr
            115                 120                 125 ctc tat ctg aca gag aag aaa tac agc cct tgt gcc tgg gag gtt gtc    432
Leu Tyr Leu Thr Glu Lys Lys Tyr Ser Pro Cys Ala Trp Glu Val Val
        130                 135                 140 aga gca gaa atc atg aga tct ttc tct tta tca aca aac ttg caa gaa    480
Arg Ala Glu Ile Met Arg Ser Phe Ser Leu Ser Thr Asn Leu Gln Glu
145                 150                 155                 160 aga tta agg agg aag gaa taa                                        501
Arg Leu Arg Arg Lys Glu
                165
```

<210> SEQ ID NO 28
<211> LENGTH: 166
<212> TYPE: PRT
<213> ORGANISM: Macaca mulatta

<400> SEQUENCE: 28

```
Cys Asp Leu Pro Glu Thr His Ser Leu Asp Asn Arg Lys Thr Met Met
1               5                   10                  15

Leu Leu Ala Gln Met Ser Arg Ile Ser Pro Ser Ser Cys Leu Met Asp
            20                  25                  30

Arg His Asp Phe Gly Phe Pro Gln Gln Glu Phe Asp Gly Asn Gln Phe
        35                  40                  45

Gln Lys Ala Pro Ala Ile Ser Val Leu His Glu Leu Ile Gln Gln Thr
    50                  55                  60

Phe Asn Leu Phe Thr Thr Lys Asp Ser Ser Ala Ala Trp Asp Glu Asp
65                  70                  75                  80

Leu Leu Asp Lys Phe Cys Thr Glu Leu Tyr Gln Gln Leu Asn Asp Leu
                85                  90                  95

Glu Ala Cys Val Met Gln Gln Glu Arg Val Gly Glu Thr Pro Leu Met
            100                 105                 110

Asn Ala Asp Ser Thr Leu Ala Val Lys Lys Tyr Phe Arg Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Leu Ser Thr Asn Leu Gln Glu
145                 150                 155                 160

Arg Leu Arg Arg Lys Glu
                165
```

<210> SEQ ID NO 29
<211> LENGTH: 501
<212> TYPE: DNA
<213> ORGANISM: Macaca mulatta
<220> FEATURE:
<221> NAME/KEY: CDS
<222> LOCATION: (1)..(498)

<400> SEQUENCE: 29

```
tgt gat ctg cct gag acc cac agc ctg ggt aat agg agg gcc ttg ata       48
Cys Asp Leu Pro Glu Thr His Ser Leu Gly Asn Arg Arg Ala Leu Ile
1               5                   10                  15 ctc ctg gca caa atg gga aga atc tct cat ttc tcc tgc ctg aag gac       96
Leu Leu Ala Gln Met Gly Arg Ile Ser His Phe Ser Cys Leu Lys Asp
            20                  25                  30 aga cat gat ttc gga ttc ccc gag gag gag ttt gat ggc cac cag ttc      144
Arg His Asp Phe Gly Phe Pro Glu Glu Glu Phe Asp Gly His Gln Phe
        35                  40                  45 cag aag act caa gcc atc tct gtc ctc cat gag atg atc cag cag acc      192
Gln Lys Thr Gln Ala Ile Ser Val Leu His Glu Met Ile Gln Gln Thr
    50                  55                  60 ttc aat ctc ttc agc aca gag gac tca tct gct gct tgg gaa cag agc      240
Phe Asn Leu Phe Ser Thr Glu Asp Ser Ser Ala Ala Trp Glu Gln Ser
65                  70                  75                  80 ctc cta gaa aaa ttt tcc act gaa ctt tac cag caa ctg aat gac ctg      288
Leu Leu Glu Lys Phe Ser Thr Glu Leu Tyr Gln Gln Leu Asn Asp Leu
                85                  90                  95 gaa gca tgt gtg ata cag gag gtt ggg gtg gaa gag act ccc ctg atg      336
Glu Ala Cys Val Ile Gln Glu Val Gly Val Glu Glu Thr Pro Leu Met
            100                 105                 110
```

| | | | | | | | | | | | | | | | | |
|---|---|---|---|---|---|---|---|---|---|---|---|---|---|---|---|---|
| aat | gtg | gac | tcc | atc | ctg | gct | gtg | agg | aaa | tac | ttc | caa | aga | atc | act | 384 |
| Asn | Val | Asp | Ser | Ile | Leu | Ala | Val | Arg | Lys | Tyr | Phe | Gln | Arg | Ile | Thr | |
| | | 115 | | | | | 120 | | | | | 125 | | | | |
| ctt | tat | cta | aca | gag | aag | aaa | tac | agc | cct | tgt | gcc | tgg | gag | gtt | gtc | 432 |
| Leu | Tyr | Leu | Thr | Glu | Lys | Lys | Tyr | Ser | Pro | Cys | Ala | Trp | Glu | Val | Val | |
| | 130 | | | | | 135 | | | | | 140 | | | | | |
| aga | gca | gaa | atc | atg | aga | tcc | ctc | tcg | ttt | tca | aca | aac | ttg | caa | aaa | 480 |
| Arg | Ala | Glu | Ile | Met | Arg | Ser | Leu | Ser | Phe | Ser | Thr | Asn | Leu | Gln | Lys | |
| 145 | | | | | 150 | | | | | 155 | | | | | 160 | |
| aga | tta | agg | agg | aag | gaa | taa | | | | | | | | | | 501 |
| Arg | Leu | Arg | Arg | Lys | Glu | | | | | | | | | | | |
| | | | | 165 | | | | | | | | | | | | |

<210> SEQ ID NO 30
<211> LENGTH: 166
<212> TYPE: PRT
<213> ORGANISM: Macaca mulatta

<400> SEQUENCE: 30

Cys Asp Leu Pro Glu Thr His Ser Leu Gly Asn Arg Arg Ala Leu Ile
1               5                   10                  15

Leu Leu Ala Gln Met Gly Arg Ile Ser His Phe Ser Cys Leu Lys Asp
            20                  25                  30

Arg His Asp Phe Gly Phe Pro Glu Glu Glu Phe Asp Gly His Gln Phe
        35                  40                  45

Gln Lys Thr Gln Ala Ile Ser Val Leu His Glu Met Ile Gln Gln Thr
    50                  55                  60

Phe Asn Leu Phe Ser Thr Glu Asp Ser Ser Ala Ala Trp Glu Gln Ser
65                  70                  75                  80

Leu Leu Glu Lys Phe Ser Thr Glu Leu Tyr Gln Gln Leu Asn Asp Leu
                85                  90                  95

Glu Ala Cys Val Ile Gln Glu Val Gly Val Glu Glu Thr Pro Leu Met
            100                 105                 110

Asn Val Asp Ser Ile Leu Ala Val Arg Lys Tyr Phe Gln Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Leu Ser Phe Ser Thr Asn Leu Gln Lys
145                 150                 155                 160

Arg Leu Arg Arg Lys Glu
                165

<210> SEQ ID NO 31
<211> LENGTH: 501
<212> TYPE: DNA
<213> ORGANISM: Macaca mulatta
<220> FEATURE:
<221> NAME/KEY: CDS
<222> LOCATION: (1)..(498)

<400> SEQUENCE: 31

| | | | | | | | | | | | | | | | | |
|---|---|---|---|---|---|---|---|---|---|---|---|---|---|---|---|---|
| tgt | gat | ctg | cct | gag | acc | cac | agc | ctg | gat | aac | agg | aag | acc | atg | atg | 48 |
| Cys | Asp | Leu | Pro | Glu | Thr | His | Ser | Leu | Asp | Asn | Arg | Lys | Thr | Met | Met | |
| 1 | | | | 5 | | | | | 10 | | | | | 15 | | |
| ctc | ctg | gca | cag | atg | agc | aga | atc | tct | cct | tcc | tcc | tgt | ctg | atg | gac | 96 |
| Leu | Leu | Ala | Gln | Met | Ser | Arg | Ile | Ser | Pro | Ser | Ser | Cys | Leu | Met | Asp | |
| | | | 20 | | | | | 25 | | | | | 30 | | | |
| aga | cat | gac | ttt | gga | ttt | ccc | cag | cag | gag | ttt | gat | ggc | aac | cag | ttc | 144 |
| Arg | His | Asp | Phe | Gly | Phe | Pro | Gln | Gln | Glu | Phe | Asp | Gly | Asn | Gln | Phe | |
| | | 35 | | | | | 40 | | | | | 45 | | | | |

```
cag aag gct cca gcc atc tct gtc ctc cat gag ctg atc cag cag acc     192
Gln Lys Ala Pro Ala Ile Ser Val Leu His Glu Leu Ile Gln Gln Thr
 50                  55                  60 ttc aac ctc ttt acc aca aaa gac tca tct gct gct tgg gat gag gac     240
Phe Asn Leu Phe Thr Thr Lys Asp Ser Ser Ala Ala Trp Asp Glu Asp
 65                  70                  75                  80 ctc cta gac aaa ttc tgc act gaa ctc tac cag cag ctg aat gac ttg     288
Leu Leu Asp Lys Phe Cys Thr Glu Leu Tyr Gln Gln Leu Asn Asp Leu
                 85                  90                  95 gaa gcc tgt gtc atg cag cag gag agg gtg gga gaa act ccc ctg atg     336
Glu Ala Cys Val Met Gln Gln Glu Arg Val Gly Glu Thr Pro Leu Met
            100                 105                 110 aat gcg gac tcc acc ttg gct gtg aag aaa tac ttc cga aga atc act     384
Asn Ala Asp Ser Thr Leu Ala Val Lys Lys Tyr Phe Arg Arg Ile Thr
        115                 120                 125 ctc tat ctg aca gag aag aaa tac agc cct tgt gcc tgg gag gtt gtc     432
Leu Tyr Leu Thr Glu Lys Lys Tyr Ser Pro Cys Ala Trp Glu Val Val
    130                 135                 140 aga gca gaa atc atg aga tcc ttc tct tta tca aca aac ttg caa gaa     480
Arg Ala Glu Ile Met Arg Ser Phe Ser Leu Ser Thr Asn Leu Gln Glu
145                 150                 155                 160 aga tta agg agg aag gaa taa                                         501
Arg Leu Arg Arg Lys Glu
                165

<210> SEQ ID NO 32
<211> LENGTH: 166
<212> TYPE: PRT
<213> ORGANISM: Macaca mulatta

<400> SEQUENCE: 32

Cys Asp Leu Pro Glu Thr His Ser Leu Asp Asn Arg Lys Thr Met Met
 1               5                  10                  15

Leu Leu Ala Gln Met Ser Arg Ile Ser Pro Ser Ser Cys Leu Met Asp
                20                  25                  30

Arg His Asp Phe Gly Phe Pro Gln Gln Glu Phe Asp Gly Asn Gln Phe
            35                  40                  45

Gln Lys Ala Pro Ala Ile Ser Val Leu His Glu Leu Ile Gln Gln Thr
 50                  55                  60

Phe Asn Leu Phe Thr Thr Lys Asp Ser Ser Ala Ala Trp Asp Glu Asp
 65                  70                  75                  80

Leu Leu Asp Lys Phe Cys Thr Glu Leu Tyr Gln Gln Leu Asn Asp Leu
                 85                  90                  95

Glu Ala Cys Val Met Gln Gln Glu Arg Val Gly Glu Thr Pro Leu Met
            100                 105                 110

Asn Ala Asp Ser Thr Leu Ala Val Lys Lys Tyr Phe Arg Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Leu Ser Thr Asn Leu Gln Glu
145                 150                 155                 160

Arg Leu Arg Arg Lys Glu
                165

<210> SEQ ID NO 33
<211> LENGTH: 501
<212> TYPE: DNA
<213> ORGANISM: Macaca mulatta
```

```
<220> FEATURE:
<221> NAME/KEY: CDS
<222> LOCATION: (1)..(498)

<400> SEQUENCE: 33 tgt gat ctg cct gag acc cac agc ctg gat aac agg aag acc atg atg        48
Cys Asp Leu Pro Glu Thr His Ser Leu Asp Asn Arg Lys Thr Met Met
1               5                   10                  15 ctc ctg gca cag atg agc aga atc tct cct tcc tcc tgt ctg atg gac        96
Leu Leu Ala Gln Met Ser Arg Ile Ser Pro Ser Ser Cys Leu Met Asp
            20                  25                  30 aga cat gac ttt gga ttt ccc cag cag gag ttt gat ggc aac cag ttc       144
Arg His Asp Phe Gly Phe Pro Gln Gln Glu Phe Asp Gly Asn Gln Phe
        35                  40                  45 cag aag gct cca gcc atc tct gtc ctc cat gag ctg atc cag cag acc       192
Gln Lys Ala Pro Ala Ile Ser Val Leu His Glu Leu Ile Gln Gln Thr
    50                  55                  60 ttc aac ctc ttt acc aca aaa gac tca tct gct gct tgg gat gag gac       240
Phe Asn Leu Phe Thr Thr Lys Asp Ser Ser Ala Ala Trp Asp Glu Asp
65                  70                  75                  80 ctc cta gac aaa ttc tgc act gaa ctc tac cag cag ctg aat gac ttg       288
Leu Leu Asp Lys Phe Cys Thr Glu Leu Tyr Gln Gln Leu Asn Asp Leu
                85                  90                  95 gaa gcc tgt gtc atg cag cag gag agg gtg gga gaa act ccc ctg atg       336
Glu Ala Cys Val Met Gln Gln Glu Arg Val Gly Glu Thr Pro Leu Met
            100                 105                 110 aat gcg gac tcc acc ttg gct gtg aag aaa tac ttc cga aga atc act       384
Asn Ala Asp Ser Thr Leu Ala Val Lys Lys Tyr Phe Arg Arg Ile Thr
        115                 120                 125 ctc tat ctg aca gag aag aaa tac agc cct tgt gcc tgg gag gtt gtc       432
Leu Tyr Leu Thr Glu Lys Lys Tyr Ser Pro Cys Ala Trp Glu Val Val
    130                 135                 140 aga gca gaa atc atg aga tct ttc tct tta tca aca aac ttg caa gaa       480
Arg Ala Glu Ile Met Arg Ser Phe Ser Leu Ser Thr Asn Leu Gln Glu
145                 150                 155                 160 aga tta agg agg aag gaa taa                                           501
Arg Leu Arg Arg Lys Glu
                165

<210> SEQ ID NO 34
<211> LENGTH: 166
<212> TYPE: PRT
<213> ORGANISM: Macaca mulatta

<400> SEQUENCE: 34

Cys Asp Leu Pro Glu Thr His Ser Leu Asp Asn Arg Lys Thr Met Met
1               5                   10                  15

Leu Leu Ala Gln Met Ser Arg Ile Ser Pro Ser Ser Cys Leu Met Asp
            20                  25                  30

Arg His Asp Phe Gly Phe Pro Gln Gln Glu Phe Asp Gly Asn Gln Phe
        35                  40                  45

Gln Lys Ala Pro Ala Ile Ser Val Leu His Glu Leu Ile Gln Gln Thr
    50                  55                  60

Phe Asn Leu Phe Thr Thr Lys Asp Ser Ser Ala Ala Trp Asp Glu Asp
65                  70                  75                  80

Leu Leu Asp Lys Phe Cys Thr Glu Leu Tyr Gln Gln Leu Asn Asp Leu
                85                  90                  95

Glu Ala Cys Val Met Gln Gln Glu Arg Val Gly Glu Thr Pro Leu Met
            100                 105                 110
```

Asn Ala Asp Ser Thr Leu Ala Val Lys Lys Tyr Phe Arg Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Leu Ser Thr Asn Leu Gln Glu
145                 150                 155                 160

Arg Leu Arg Arg Lys Glu
                165

<210> SEQ ID NO 35
<211> LENGTH: 501
<212> TYPE: DNA
<213> ORGANISM: Macaca mulatta
<220> FEATURE:
<221> NAME/KEY: CDS
<222> LOCATION: (1)..(498)

<400> SEQUENCE: 35

```
tgt gat ctg cct gag acc cac agc ctg gat aac aga agg acc atg atg      48
Cys Asp Leu Pro Glu Thr His Ser Leu Asp Asn Arg Arg Thr Met Met
1               5                   10                  15 ctc ctg aaa caa atg agc aga atc tct cct tcc tcc tgt ctg atg gac      96
Leu Leu Lys Gln Met Ser Arg Ile Ser Pro Ser Ser Cys Leu Met Asp
            20                  25                  30 aga cat gac ttt gga ttt ccc cag cag gag ttt gat ggc aac cag ttc     144
Arg His Asp Phe Gly Phe Pro Gln Gln Glu Phe Asp Gly Asn Gln Phe
        35                  40                  45 cag aag gct cca gcc atc tct gtc ctc cat gag ctg atc cag cag acc     192
Gln Lys Ala Pro Ala Ile Ser Val Leu His Glu Leu Ile Gln Gln Thr
    50                  55                  60 ttc aac ctc ttt acc aca aaa gac tca tct gct gct tgg gat gag gac     240
Phe Asn Leu Phe Thr Thr Lys Asp Ser Ser Ala Ala Trp Asp Glu Asp
65                  70                  75                  80 ctc cta gac aaa ttc tgc act gaa ctc tac cag cag ctg aat gac ttg     288
Leu Leu Asp Lys Phe Cys Thr Glu Leu Tyr Gln Gln Leu Asn Asp Leu
                85                  90                  95 gaa gcc tgt gtc atg cag cag gag agg gtg gga gaa act ctc ctg atg     336
Glu Ala Cys Val Met Gln Gln Glu Arg Val Gly Glu Thr Leu Leu Met
            100                 105                 110 aat gcg gac tcc acc ttg gct gtg aag aaa tac ttc cga aga atc act     384
Asn Ala Asp Ser Thr Leu Ala Val Lys Lys Tyr Phe Arg Arg Ile Thr
        115                 120                 125 ctc tat ctg aca gag aag aaa tac agc cct tgt gcc tgg gag gtt gtc     432
Leu Tyr Leu Thr Glu Lys Lys Tyr Ser Pro Cys Ala Trp Glu Val Val
    130                 135                 140 aga gca gaa atc atg aga tcc ttc tct tta tca aca aac ttg caa gaa     480
Arg Ala Glu Ile Met Arg Ser Phe Ser Leu Ser Thr Asn Leu Gln Glu
145                 150                 155                 160 aga tta agg agg aag gaa taa                                          501
Arg Leu Arg Arg Lys Glu
                165
```

<210> SEQ ID NO 36
<211> LENGTH: 166
<212> TYPE: PRT
<213> ORGANISM: Macaca mulatta

<400> SEQUENCE: 36

Cys Asp Leu Pro Glu Thr His Ser Leu Asp Asn Arg Arg Thr Met Met
1               5                   10                  15

Leu Leu Lys Gln Met Ser Arg Ile Ser Pro Ser Ser Cys Leu Met Asp

```
                   20                  25                  30
Arg His Asp Phe Gly Phe Pro Gln Gln Glu Phe Asp Gly Asn Gln Phe
            35                  40                  45

Gln Lys Ala Pro Ala Ile Ser Val Leu His Glu Leu Ile Gln Gln Thr
 50                  55                  60

Phe Asn Leu Phe Thr Thr Lys Asp Ser Ser Ala Ala Trp Asp Glu Asp
 65                  70                  75                  80

Leu Leu Asp Lys Phe Cys Thr Glu Leu Tyr Gln Gln Leu Asn Asp Leu
                 85                  90                  95

Glu Ala Cys Val Met Gln Gln Glu Arg Val Gly Glu Thr Leu Leu Met
            100                 105                 110

Asn Ala Asp Ser Thr Leu Ala Val Lys Lys Tyr Phe Arg Arg Ile Thr
            115                 120                 125

Leu Tyr Leu Thr Glu Lys Lys Tyr Ser Pro Cys Ala Trp Glu Val Val
            130                 135                 140

Arg Ala Glu Ile Met Arg Ser Phe Ser Leu Ser Thr Asn Leu Gln Glu
145                 150                 155                 160

Arg Leu Arg Arg Lys Glu
                165

<210> SEQ ID NO 37
<211> LENGTH: 570
<212> TYPE: DNA
<213> ORGANISM: Homo sapiens
<220> FEATURE:
<221> NAME/KEY: CDS
<222> LOCATION: (1)..(567)

<400> SEQUENCE: 37 atg gcc ttg tcc ttt tct tta ctg atg gtc gtg ctg gta ctc agc tac       48
Met Ala Leu Ser Phe Ser Leu Leu Met Val Val Leu Val Leu Ser Tyr
 1               5                  10                  15 aaa tcc atc tgc tct ctg ggc tgt gat ctg cct cag acc cac agc ctg       96
Lys Ser Ile Cys Ser Leu Gly Cys Asp Leu Pro Gln Thr His Ser Leu
                20                  25                  30 cgt aat agg agg gcc ttg ata ctc ctg gca caa atg gga aga atc tct      144
Arg Asn Arg Arg Ala Leu Ile Leu Leu Ala Gln Met Gly Arg Ile Ser
            35                  40                  45 cct ttc tcc tgc ttg aag gac aga cat gaa ttc aga ttc cca gag gag      192
Pro Phe Ser Cys Leu Lys Asp Arg His Glu Phe Arg Phe Pro Glu Glu
 50                  55                  60 gag ttt gat ggc cac cag ttc cag aag act caa gcc atc tct gtc ctc      240
Glu Phe Asp Gly His Gln Phe Gln Lys Thr Gln Ala Ile Ser Val Leu
 65                  70                  75                  80 cat gag atg atc cag cag acc ttc aat ctc ttc agc aca gag gac tca      288
His Glu Met Ile Gln Gln Thr Phe Asn Leu Phe Ser Thr Glu Asp Ser
                 85                  90                  95 tct gct gct tgg gaa cag agc ctc cta gaa aaa ttt tcc act gaa ctt      336
Ser Ala Ala Trp Glu Gln Ser Leu Leu Glu Lys Phe Ser Thr Glu Leu
            100                 105                 110 tac cag caa ctg aat gac ctg gaa gca tgt gtg ata cag gag gtt ggg      384
Tyr Gln Gln Leu Asn Asp Leu Glu Ala Cys Val Ile Gln Glu Val Gly
            115                 120                 125 gtg gaa gag act ccc ctg atg aat gag gac tcc atc ctg gct gtg agg      432
Val Glu Glu Thr Pro Leu Met Asn Glu Asp Ser Ile Leu Ala Val Arg
            130                 135                 140 aaa tac ttc caa aga atc act ctt tat cta aca gag aag aaa tac agc      480
Lys Tyr Phe Gln Arg Ile Thr Leu Tyr Leu Thr Glu Lys Lys Tyr Ser
145                 150                 155                 160
```

```
cct tgt gcc tgg gag gtt gtc aga gca gaa atc atg aga tcc ctc tcg      528
Pro Cys Ala Trp Glu Val Val Arg Ala Glu Ile Met Arg Ser Leu Ser
            165                 170                 175 ttt tca aca aac ttg caa aaa aga tta agg agg aag gat tga              570
Phe Ser Thr Asn Leu Gln Lys Arg Leu Arg Arg Lys Asp
        180                 185

<210> SEQ ID NO 38
<211> LENGTH: 189
<212> TYPE: PRT
<213> ORGANISM: Homo sapiens

<400> SEQUENCE: 38

Met Ala Leu Ser Phe Ser Leu Leu Met Val Val Leu Val Leu Ser Tyr
1               5                   10                  15

Lys Ser Ile Cys Ser Leu Gly Cys Asp Leu Pro Gln Thr His Ser Leu
            20                  25                  30

Arg Asn Arg Arg Ala Leu Ile Leu Leu Ala Gln Met Gly Arg Ile Ser
        35                  40                  45

Pro Phe Ser Cys Leu Lys Asp Arg His Glu Phe Arg Phe Pro Glu Glu
    50                  55                  60

Glu Phe Asp Gly His Gln Phe Gln Lys Thr Gln Ala Ile Ser Val Leu
65                  70                  75                  80

His Glu Met Ile Gln Gln Thr Phe Asn Leu Phe Ser Thr Glu Asp Ser
                85                  90                  95

Ser Ala Ala Trp Glu Gln Ser Leu Leu Glu Lys Phe Ser Thr Glu Leu
            100                 105                 110

Tyr Gln Gln Leu Asn Asp Leu Glu Ala Cys Val Ile Gln Glu Val Gly
        115                 120                 125

Val Glu Glu Thr Pro Leu Met Asn Glu Asp Ser Ile Leu Ala Val Arg
    130                 135                 140

Lys Tyr Phe Gln Arg Ile Thr Leu Tyr Leu Thr Glu Lys Lys Tyr Ser
145                 150                 155                 160

Pro Cys Ala Trp Glu Val Val Arg Ala Glu Ile Met Arg Ser Leu Ser
                165                 170                 175

Phe Ser Thr Asn Leu Gln Lys Arg Leu Arg Arg Lys Asp
            180                 185

<210> SEQ ID NO 39
<211> LENGTH: 753
<212> TYPE: DNA
<213> ORGANISM: Homo sapiens
<220> FEATURE:
<221> NAME/KEY: CDS
<222> LOCATION: (102)..(572)

<400> SEQUENCE: 39
atagctagca tgcgcaaatt taaagcgctg attcagaaaa cctagaggcc gcggttcaag    60
ttacccacct caggtagcct agtgatattt gcaaaatccc a atg gcc cgg tcc ttt  116
                                             Met Ala Arg Ser Phe
                                             1               5 tct tta ctg atg gtc gtg ctg gta ctc agc tac aaa tcc atc tgc tct    164
Ser Leu Leu Met Val Val Leu Val Leu Ser Tyr Lys Ser Ile Cys Ser
            10                  15                  20 ctg ggc tgt gat ctg cct cag acc cac agc ctg cgt aat agg agg gcc    212
Leu Gly Cys Asp Leu Pro Gln Thr His Ser Leu Arg Asn Arg Arg Ala
        25                  30                  35 ttg ata ctc ctg gca caa atg gga aga atc tct cct ttc tcc tgc ttg    260
```

```
Leu Ile Leu Leu Ala Gln Met Gly Arg Ile Ser Pro Phe Ser Cys Leu
         40                  45                  50 aag gac aga cat gaa ttc aga ttc cca gag gag gag ttt gat ggc aac      308
Lys Asp Arg His Glu Phe Arg Phe Pro Glu Glu Glu Phe Asp Gly Asn
 55                  60                  65 cag ttc cag aag act caa gcc atc tct gtc ctc cat gag atg atc cag      356
Gln Phe Gln Lys Thr Gln Ala Ile Ser Val Leu His Glu Met Ile Gln
 70                  75                  80                  85 cag acc ttc aat ctc ttc agc aca gag gac tca tct gct gct tgg gaa      404
Gln Thr Phe Asn Leu Phe Ser Thr Glu Asp Ser Ser Ala Ala Trp Glu
                 90                  95                 100 cag agc ttc cta gaa aaa ttt tcc act gaa ctt tac cag caa ctg aat      452
Gln Ser Phe Leu Glu Lys Phe Ser Thr Glu Leu Tyr Gln Gln Leu Asn
             105                 110                 115 aac ttg gaa gca tgt gtg ata cag gag gtt ggg gtg gaa gag act ccc      500
Asn Leu Glu Ala Cys Val Ile Gln Glu Val Gly Val Glu Glu Thr Pro
         120                 125                 130 ctg atg aat gag gac tcc atc ctg gct gtg agg aaa tac ttc caa aga      548
Leu Met Asn Glu Asp Ser Ile Leu Ala Val Arg Lys Tyr Phe Gln Arg
     135                 140                 145 atc act ctt tat cta aca gag aag aaatacagcc cttgtgcctg ggaggttgtc     602
Ile Thr Leu Tyr Leu Thr Glu Lys
150                 155 agagcagaaa tcatgagatc cctctcgttt tcaacaaact tgcaaaaaag attaaggagg    662
aaggattgaa acctggttca acatggaaat gatcctgatt gactaataca ttatctcaca   722
ctttcatgat tcttccaatc gatcgcgcgc a                                   753

<210> SEQ ID NO 40
<211> LENGTH: 157
<212> TYPE: PRT
<213> ORGANISM: Homo sapiens

<400> SEQUENCE: 40

Met Ala Arg Ser Phe Ser Leu Leu Met Val Val Leu Val Leu Ser Tyr
 1               5                  10                  15

Lys Ser Ile Cys Ser Leu Gly Cys Asp Leu Pro Gln Thr His Ser Leu
             20                  25                  30

Arg Asn Arg Arg Ala Leu Ile Leu Leu Ala Gln Met Gly Arg Ile Ser
         35                  40                  45

Pro Phe Ser Cys Leu Lys Asp Arg His Glu Phe Arg Phe Pro Glu Glu
 50                  55                  60

Glu Phe Asp Gly Asn Gln Phe Gln Lys Thr Gln Ala Ile Ser Val Leu
 65                  70                  75                  80

His Glu Met Ile Gln Gln Thr Phe Asn Leu Phe Ser Thr Glu Asp Ser
                 85                  90                  95

Ser Ala Ala Trp Glu Gln Ser Phe Leu Glu Lys Phe Ser Thr Glu Leu
            100                 105                 110

Tyr Gln Gln Leu Asn Asn Leu Glu Ala Cys Val Ile Gln Glu Val Gly
        115                 120                 125

Val Glu Glu Thr Pro Leu Met Asn Glu Asp Ser Ile Leu Ala Val Arg
    130                 135                 140

Lys Tyr Phe Gln Arg Ile Thr Leu Tyr Leu Thr Glu Lys
145                 150                 155

<210> SEQ ID NO 41
<211> LENGTH: 755
<212> TYPE: DNA
```

<213> ORGANISM: Homo sapiens
<220> FEATURE:
<221> NAME/KEY: CDS
<222> LOCATION: (103)..(672)
<220> FEATURE:
<221> NAME/KEY: modified_base
<222> LOCATION: (733)..(733)
<223> OTHER INFORMATION: a, t, c, g, unknown or other

<400> SEQUENCE: 41

```
tatagctagc atgcgcaaat ttaaagcgct gatcagaaaa cctagaggcc gaagttcaag      60
gttatccatc tcaagtagcc tagcaatatt tgcaacatcc ca atg gcc ctg tcc       114
                                              Met Ala Leu Ser
                                                1 ttt tct tta ctg atg gtc gtg ctg gtc ctc agc tac aaa tcc atc tgt      162
Phe Ser Leu Leu Met Val Val Leu Val Leu Ser Tyr Lys Ser Ile Cys
  5              10                  15                  20 tct ctg ggc tgt gat ctg cct cag acc cac agc ctg ggt aat agg agg      210
Ser Leu Gly Cys Asp Leu Pro Gln Thr His Ser Leu Gly Asn Arg Arg
             25                  30                  35 gcc ttg ata ctc ctg gga caa atg gga aga atc tct cct ttt tcc tgc      258
Ala Leu Ile Leu Leu Gly Gln Met Gly Arg Ile Ser Pro Phe Ser Cys
         40                  45                  50 ctg aag gac aga cat gat ttc cga atc ccc cag gag gag ttt gat ggc      306
Leu Lys Asp Arg His Asp Phe Arg Ile Pro Gln Glu Glu Phe Asp Gly
     55                  60                  65 aac cag ttc cag aag gct caa gcc atc tct gtc ctc cat gag atg ttc      354
Asn Gln Phe Gln Lys Ala Gln Ala Ile Ser Val Leu His Glu Met Phe
 70                  75                  80 cag cag acc ttc aat ctc ttc agc aca gag gac tca tct gct gct tgg      402
Gln Gln Thr Phe Asn Leu Phe Ser Thr Glu Asp Ser Ser Ala Ala Trp
 85                  90                  95                 100 gaa cag agc ctc cta gaa aaa ttt tcc act gaa ctt tac cag caa ctg      450
Glu Gln Ser Leu Leu Glu Lys Phe Ser Thr Glu Leu Tyr Gln Gln Leu
                105                 110                 115 aat gac ctg gaa gca tgt gtg ata cag gag gtt ggg atg gaa gag act      498
Asn Asp Leu Glu Ala Cys Val Ile Gln Glu Val Gly Met Glu Glu Thr
            120                 125                 130 ccc ctg atg aat gag gac tcc atc ctg gct gtg agg aaa tac ttc caa      546
Pro Leu Met Asn Glu Asp Ser Ile Leu Ala Val Arg Lys Tyr Phe Gln
        135                 140                 145 aga atc act ctt tat cta aca gag aag aaa tac agc cct tgt gcc tgg      594
Arg Ile Thr Leu Tyr Leu Thr Glu Lys Lys Tyr Ser Pro Cys Ala Trp
    150                 155                 160 gag gtt gtc aga gca gaa atc atg aga tct ctc tct ttt tca aca aac      642
Glu Val Val Arg Ala Glu Ile Met Arg Ser Leu Ser Phe Ser Thr Asn
165                 170                 175                 180 ttg caa aaa ata tta agg agg aag gat tga aaactggttc aacatggcaa        692
Leu Gln Lys Ile Leu Arg Arg Lys Asp
                185 tgatcctgat tgactaatac attatctcac actttcatga ntcttccaat cgatcgcgcg    752 cac                                                                  755
```

<210> SEQ ID NO 42
<211> LENGTH: 189
<212> TYPE: PRT
<213> ORGANISM: Homo sapiens

<400> SEQUENCE: 42

```
Met Ala Leu Ser Phe Ser Leu Leu Met Val Val Leu Val Leu Ser Tyr
  1               5                  10                  15
```

```
Lys Ser Ile Cys Ser Leu Gly Cys Asp Leu Pro Gln Thr His Ser Leu
            20                  25                  30

Gly Asn Arg Arg Ala Leu Ile Leu Leu Gly Gln Met Gly Arg Ile Ser
        35                  40                  45

Pro Phe Ser Cys Leu Lys Asp Arg His Asp Phe Arg Ile Pro Gln Glu
    50                  55                  60

Glu Phe Asp Gly Asn Gln Phe Gln Lys Ala Gln Ala Ile Ser Val Leu
65                  70                  75                  80

His Glu Met Phe Gln Gln Thr Phe Asn Leu Phe Ser Thr Glu Asp Ser
                85                  90                  95

Ser Ala Ala Trp Glu Gln Ser Leu Leu Glu Lys Phe Ser Thr Glu Leu
            100                 105                 110

Tyr Gln Gln Leu Asn Asp Leu Glu Ala Cys Val Ile Gln Glu Val Gly
        115                 120                 125

Met Glu Glu Thr Pro Leu Met Asn Glu Asp Ser Ile Leu Ala Val Arg
    130                 135                 140

Lys Tyr Phe Gln Arg Ile Thr Leu Tyr Leu Thr Glu Lys Lys Tyr Ser
145                 150                 155                 160

Pro Cys Ala Trp Glu Val Val Arg Ala Glu Ile Met Arg Ser Leu Ser
                165                 170                 175

Phe Ser Thr Asn Leu Gln Lys Ile Leu Arg Arg Lys Asp
            180                 185

<210> SEQ ID NO 43
<211> LENGTH: 759
<212> TYPE: DNA
<213> ORGANISM: Homo sapiens
<220> FEATURE:
<221> NAME/KEY: CDS
<222> LOCATION: (86)..(655)
<220> FEATURE:
<221> NAME/KEY: modified_base
<222> LOCATION: (758)..(758)
<223> OTHER INFORMATION: a, t, c, g, unknown or other

<400> SEQUENCE: 43
gtgcgcgcga tcgattcaga aaacctagag gccgaagttc aaggttatcc atctcaagta      60
gcctagcaat atttgcaaca tccca atg gcc ctg tcc ttt tct tta ctt atg      112
                            Met Ala Leu Ser Phe Ser Leu Leu Met
                             1               5 gcc gtg ctg gtg ctc agc tac aaa tcc atc tgt tct cta ggc tgt gat      160
Ala Val Leu Val Leu Ser Tyr Lys Ser Ile Cys Ser Leu Gly Cys Asp
 10                  15                  20                  25 ctg cct cag acc cac agc ctg ggt aat agg agg gcc ttg ata ctc ctg      208
Leu Pro Gln Thr His Ser Leu Gly Asn Arg Arg Ala Leu Ile Leu Leu
                 30                  35                  40 gca caa atg gga aga atc tct cct ttc tcc tgc ctg aag gac aga cat      256
Ala Gln Met Gly Arg Ile Ser Pro Phe Ser Cys Leu Lys Asp Arg His
         45                  50                  55 gat ttc cga atc ccc cag gag gag ttt gat ggc aac cag ttc cag aag      304
Asp Phe Arg Ile Pro Gln Glu Glu Phe Asp Gly Asn Gln Phe Gln Lys
     60                  65                  70 gct caa gcc atc tct gtc ctc cat gag atg atc cag cag acc ttc aat      352
Ala Gln Ala Ile Ser Val Leu His Glu Met Ile Gln Gln Thr Phe Asn
 75                  80                  85 ctc ttc agc aca gag gac tca tct gct gct tgg gaa cag agc ctc cta      400
Leu Phe Ser Thr Glu Asp Ser Ser Ala Ala Trp Glu Gln Ser Leu Leu
 90                  95                 100                 105
```

| | | | | | | | | | | | | | | | | |
|---|---|---|---|---|---|---|---|---|---|---|---|---|---|---|---|---|
| gaa | aaa | ttt | tcc | act | gaa | ctt | tac | cag | caa | ctg | aat | gac | ctg | gaa | gca | 448 |
| Glu | Lys | Phe | Ser | Thr | Glu | Leu | Tyr | Gln | Gln | Leu | Asn | Asp | Leu | Glu | Ala | |
| | | | 110 | | | | | 115 | | | | | 120 | | | |
| tgt | gtg | ata | cag | gag | gtt | ggg | gtg | gaa | gag | act | ccc | ctg | atg | aat | gag | 496 |
| Cys | Val | Ile | Gln | Glu | Val | Gly | Val | Glu | Glu | Thr | Pro | Leu | Met | Asn | Glu | |
| | | 125 | | | | | 130 | | | | | 135 | | | | |
| gac | tcc | atc | ctg | gct | gtg | agg | aaa | tac | ttc | caa | aga | atc | act | ctt | tat | 544 |
| Asp | Ser | Ile | Leu | Ala | Val | Arg | Lys | Tyr | Phe | Gln | Arg | Ile | Thr | Leu | Tyr | |
| 140 | | | | | 145 | | | | | 150 | | | | | | |
| cta | ata | gag | agg | aaa | tac | agc | cct | tgt | gcc | tgg | gag | gtt | gtc | aga | gca | 592 |
| Leu | Ile | Glu | Arg | Lys | Tyr | Ser | Pro | Cys | Ala | Trp | Glu | Val | Val | Arg | Ala | |
| | 155 | | | | | 160 | | | | | 165 | | | | | |
| gaa | atc | atg | aga | tcc | ctc | tcg | ttt | tca | aca | aac | ttg | caa | aaa | aga | tta | 640 |
| Glu | Ile | Met | Arg | Ser | Leu | Ser | Phe | Ser | Thr | Asn | Leu | Gln | Lys | Arg | Leu | |
| 170 | | | | | 175 | | | | | 180 | | | | | 185 | |

| | | | | |
|---|---|---|---|---|
| agg | agg | aag | gat | tga aaactggttc aacatggcaa tgatcctgat tgactaatac | 695 |
| Arg | Arg | Lys | Asp | | | attatctcac actttcatga gttcttccaa tcagcgcttt aaatttgcgc atgctagcta 755 tant 759

<210> SEQ ID NO 44
<211> LENGTH: 189
<212> TYPE: PRT
<213> ORGANISM: Homo sapiens

<400> SEQUENCE: 44

Met Ala Leu Ser Phe Ser Leu Leu Met Ala Val Leu Val Leu Ser Tyr
1               5                   10                  15

Lys Ser Ile Cys Ser Leu Gly Cys Asp Leu Pro Gln Thr His Ser Leu
            20                  25                  30

Gly Asn Arg Arg Ala Leu Ile Leu Leu Ala Gln Met Gly Arg Ile Ser
        35                  40                  45

Pro Phe Ser Cys Leu Lys Asp Arg His Asp Phe Arg Ile Pro Gln Glu
    50                  55                  60

Glu Phe Asp Gly Asn Gln Phe Gln Lys Ala Gln Ala Ile Ser Val Leu
65                  70                  75                  80

His Glu Met Ile Gln Gln Thr Phe Asn Leu Phe Ser Thr Glu Asp Ser
                85                  90                  95

Ser Ala Ala Trp Glu Gln Ser Leu Leu Glu Lys Phe Ser Thr Glu Leu
            100                 105                 110

Tyr Gln Gln Leu Asn Asp Leu Glu Ala Cys Val Ile Gln Glu Val Gly
        115                 120                 125

Val Glu Glu Thr Pro Leu Met Asn Glu Asp Ser Ile Leu Ala Val Arg
    130                 135                 140

Lys Tyr Phe Gln Arg Ile Thr Leu Tyr Leu Ile Glu Arg Lys Tyr Ser
145                 150                 155                 160

Pro Cys Ala Trp Glu Val Val Arg Ala Glu Ile Met Arg Ser Leu Ser
                165                 170                 175

Phe Ser Thr Asn Leu Gln Lys Arg Leu Arg Arg Lys Asp
            180                 185

<210> SEQ ID NO 45
<211> LENGTH: 756
<212> TYPE: DNA
<213> ORGANISM: Homo sapiens
<220> FEATURE:
<221> NAME/KEY: CDS
<222> LOCATION: (105)..(674)

<400> SEQUENCE: 45

```
atatagctag catgcgcaaa tttaaagcgc tgattcagaa aacctagagg ccgaagttca      60
aggttaccca tctcaagtag cctagcaaca tttgcaacat ccca atg gcc ctg tcc     116
                                                Met Ala Leu Ser
                                                 1 ttt tct tta ctg atg gcc gtg ctg gtg ctc agc tac aaa tcc atc tgt      164
Phe Ser Leu Leu Met Ala Val Leu Val Leu Ser Tyr Lys Ser Ile Cys
 5                  10                  15                  20 tct cta ggc tgt gat ctg cct cag acc cac agc ctg ggt aat agg agg      212
Ser Leu Gly Cys Asp Leu Pro Gln Thr His Ser Leu Gly Asn Arg Arg
                 25                  30                  35 gcc ttg ata ctc ctg gca caa atg gga aga atc tct cct ttc tcc tgc      260
Ala Leu Ile Leu Leu Ala Gln Met Gly Arg Ile Ser Pro Phe Ser Cys
             40                  45                  50 ctg aag gac aga cat gac ttt gga ctt ccc cag gag gag ttt gat ggc      308
Leu Lys Asp Arg His Asp Phe Gly Leu Pro Gln Glu Glu Phe Asp Gly
         55                  60                  65 aac cag ttc cag aag act caa gcc atc tct gtc ctc cat gag atg atc      356
Asn Gln Phe Gln Lys Thr Gln Ala Ile Ser Val Leu His Glu Met Ile
 70                  75                  80 cag cag acc ttc aat ctc ttc agc aca aag gat tca tct gct gct tgg      404
Gln Gln Thr Phe Asn Leu Phe Ser Thr Lys Asp Ser Ser Ala Ala Trp
85                  90                  95                 100 gat gag agc ctc cta gac aaa ttc tac att gaa ctt ttc cag caa ctg      452
Asp Glu Ser Leu Leu Asp Lys Phe Tyr Ile Glu Leu Phe Gln Gln Leu
                105                 110                 115 aat gtc cta gaa gcc tgt gtg aca cag gag gtt ggg gtg gaa gag att      500
Asn Val Leu Glu Ala Cys Val Thr Gln Glu Val Gly Val Glu Glu Ile
            120                 125                 130 gcc ctg atg aat gag gac tcc atc ctg gct gtg agg aaa tac ttt caa      548
Ala Leu Met Asn Glu Asp Ser Ile Leu Ala Val Arg Lys Tyr Phe Gln
        135                 140                 145 aga atc act ctt tat ctg atg ggg aag aaa tac agc cct tgt gcc tgg      596
Arg Ile Thr Leu Tyr Leu Met Gly Lys Lys Tyr Ser Pro Cys Ala Trp
    150                 155                 160 gag gtt gtc aga gca gaa atc atg aga tcc ttc tct ttt tca aca aac      644
Glu Val Val Arg Ala Glu Ile Met Arg Ser Phe Ser Phe Ser Thr Asn
165                 170                 175                 180 ttg caa aaa gga tta aga agg aag gat tga aaactcattc aacatggaaa        694
Leu Gln Lys Gly Leu Arg Arg Lys Asp
                185 tgatcctcat tgattaatac atcatctcac actttcatga ttcttccaat cgatcgcgcg    754 ca                                                                   756
```

<210> SEQ ID NO 46
<211> LENGTH: 189
<212> TYPE: PRT
<213> ORGANISM: Homo sapiens

<400> SEQUENCE: 46

```
Met Ala Leu Ser Phe Ser Leu Leu Met Ala Val Leu Val Leu Ser Tyr
 1               5                  10                  15

Lys Ser Ile Cys Ser Leu Gly Cys Asp Leu Pro Gln Thr His Ser Leu
             20                  25                  30

Gly Asn Arg Arg Ala Leu Ile Leu Leu Ala Gln Met Gly Arg Ile Ser
         35                  40                  45

Pro Phe Ser Cys Leu Lys Asp Arg His Asp Phe Gly Leu Pro Gln Glu
```

```
                50                    55                    60
Glu Phe Asp Gly Asn Gln Phe Gln Lys Thr Gln Ala Ile Ser Val Leu
 65                  70                  75                  80

His Glu Met Ile Gln Gln Thr Phe Asn Leu Phe Ser Thr Lys Asp Ser
                 85                  90                  95

Ser Ala Ala Trp Asp Glu Ser Leu Leu Asp Lys Phe Tyr Ile Glu Leu
                100                 105                 110

Phe Gln Gln Leu Asn Val Leu Glu Ala Cys Val Thr Gln Glu Val Gly
                115                 120                 125

Val Glu Glu Ile Ala Leu Met Asn Glu Asp Ser Ile Leu Ala Val Arg
130                 135                 140

Lys Tyr Phe Gln Arg Ile Thr Leu Tyr Leu Met Gly Lys Lys Tyr Ser
145                 150                 155                 160

Pro Cys Ala Trp Glu Val Val Arg Ala Glu Ile Met Arg Ser Phe Ser
                165                 170                 175

Phe Ser Thr Asn Leu Gln Lys Gly Leu Arg Arg Lys Asp
                180                 185

<210> SEQ ID NO 47
<211> LENGTH: 756
<212> TYPE: DNA
<213> ORGANISM: Homo sapiens
<220> FEATURE:
<221> NAME/KEY: CDS
<222> LOCATION: (86)..(655)
<220> FEATURE:
<221> NAME/KEY: modified_base
<222> LOCATION: (755)..(755)
<223> OTHER INFORMATION: a, t, c, g, unknown or other

<400> SEQUENCE: 47
tggcgcgcga tcgattcaga aaacctagag gccgaagttc aaggttatcc atctcaagta      60
gcctagcaat atttgcaaca tccca atg gcc ctg tcc ttt tct tta ctt atg      112
                            Met Ala Leu Ser Phe Ser Leu Leu Met
                             1               5 gcc gtg ctg gtg ctc agc tac aaa tcc atc tgt tct cta ggc tgt gat      160
Ala Val Leu Val Leu Ser Tyr Lys Ser Ile Cys Ser Leu Gly Cys Asp
 10                  15                  20                  25 ctg cct cag acc cac agc ctg ggt aat agg agg gcc tcg ata ctc ctg      208
Leu Pro Gln Thr His Ser Leu Gly Asn Arg Arg Ala Ser Ile Leu Leu
                 30                  35                  40 gga caa atg gga aga atc tct cct ttc tcc tgc ctg aag gac aga cat      256
Gly Gln Met Gly Arg Ile Ser Pro Phe Ser Cys Leu Lys Asp Arg His
             45                  50                  55 gat ttc cga atc ccc cag gag gag ttt gat ggc aac cag ttc cag aag      304
Asp Phe Arg Ile Pro Gln Glu Glu Phe Asp Gly Asn Gln Phe Gln Lys
         60                  65                  70 gct caa gcc atc tct gcc ttc cat gag atg atc cag cag acc ttc aat      352
Ala Gln Ala Ile Ser Ala Phe His Glu Met Ile Gln Gln Thr Phe Asn
 75                  80                  85 ctc ttc agc aca aag gat tca tct gct gct tgg gat gag acc ctc cta      400
Leu Phe Ser Thr Lys Asp Ser Ser Ala Ala Trp Asp Glu Thr Leu Leu
 90                  95                 100                 105 gac aaa ttc tac att gaa ctt ttc cag caa ctg aat gac cta gaa gcc      448
Asp Lys Phe Tyr Ile Glu Leu Phe Gln Gln Leu Asn Asp Leu Glu Ala
                110                 115                 120 tgt gtg aca cag gag gtt ggg gtg gaa gag att gcc ctg atg aat gag      496
Cys Val Thr Gln Glu Val Gly Val Glu Glu Ile Ala Leu Met Asn Glu
                125                 130                 135
```

```
gac tcc atc ctg gct gtg agg aaa tac ttt caa aga atc act ctt tat    544
Asp Ser Ile Leu Ala Val Arg Lys Tyr Phe Gln Arg Ile Thr Leu Tyr
        140                 145                 150 ctg atg ggg aag aaa tac agc cct tgt gcc tgg gag gtt gtc aga gca    592
Leu Met Gly Lys Lys Tyr Ser Pro Cys Ala Trp Glu Val Val Arg Ala
155                 160                 165 gaa atc atg aga tcc ttc tct ttt tca aca aac ttg caa aaa gga tta    640
Glu Ile Met Arg Ser Phe Ser Phe Ser Thr Asn Leu Gln Lys Gly Leu
170                 175                 180                 185 aga agg aag gat tga aaactcattc aacatggaaa tgatcctcat tgattaatac    695
Arg Arg Lys Asp atcatctcac actttcatga gttcttccaa tcagcgcttt aaatttgcgc atgctaggtn   755
t                                                                   756

<210> SEQ ID NO 48
<211> LENGTH: 189
<212> TYPE: PRT
<213> ORGANISM: Homo sapiens

<400> SEQUENCE: 48

Met Ala Leu Ser Phe Ser Leu Leu Met Ala Val Leu Val Leu Ser Tyr
1               5                   10                  15

Lys Ser Ile Cys Ser Leu Gly Cys Asp Leu Pro Gln Thr His Ser Leu
            20                  25                  30

Gly Asn Arg Arg Ala Ser Ile Leu Leu Gly Gln Met Gly Arg Ile Ser
        35                  40                  45

Pro Phe Ser Cys Leu Lys Asp Arg His Asp Phe Arg Ile Pro Gln Glu
    50                  55                  60

Glu Phe Asp Gly Asn Gln Phe Gln Lys Ala Gln Ala Ile Ser Ala Phe
65                  70                  75                  80

His Glu Met Ile Gln Gln Thr Phe Asn Leu Phe Ser Thr Lys Asp Ser
                85                  90                  95

Ser Ala Ala Trp Asp Glu Thr Leu Leu Asp Lys Phe Tyr Ile Glu Leu
            100                 105                 110

Phe Gln Gln Leu Asn Asp Leu Glu Ala Cys Val Thr Gln Glu Val Gly
        115                 120                 125

Val Glu Glu Ile Ala Leu Met Asn Glu Asp Ser Ile Leu Ala Val Arg
    130                 135                 140

Lys Tyr Phe Gln Arg Ile Thr Leu Tyr Leu Met Gly Lys Lys Tyr Ser
145                 150                 155                 160

Pro Cys Ala Trp Glu Val Val Arg Ala Glu Ile Met Arg Ser Phe Ser
                165                 170                 175

Phe Ser Thr Asn Leu Gln Lys Gly Leu Arg Arg Lys Asp
            180                 185

<210> SEQ ID NO 49
<211> LENGTH: 758
<212> TYPE: DNA
<213> ORGANISM: Homo sapiens
<220> FEATURE:
<221> NAME/KEY: CDS
<222> LOCATION: (85)..(654)
<220> FEATURE:
<221> NAME/KEY: modified_base
<222> LOCATION: (757)..(757)
<223> OTHER INFORMATION: a, t, c, g, unknown or other

<400> SEQUENCE: 49
tgcgcgcgat cgattcagaa aacctagagg ccgaagttca aggttatcca tctcaagtag    60
```

```
cctagcaata tttgcaacat ccca atg gcc ctg tcc ttt tct tta ctg atg        111
                           Met Ala Leu Ser Phe Ser Leu Leu Met
                            1               5 gcc gtg ctg gtg ctc agc tac aaa tcc atc tgt tct ctg ggc tgt gat      159
Ala Val Leu Val Leu Ser Tyr Lys Ser Ile Cys Ser Leu Gly Cys Asp
 10              15                  20                  25 ctg cct cag acc cac agc ctg ggt aat agg agg gcc ttg ata ctc ctg      207
Leu Pro Gln Thr His Ser Leu Gly Asn Arg Arg Ala Leu Ile Leu Leu
                 30                  35                  40 gca caa atg gga aga atc tct cat ttc tcc tgc ctg aag gac aga cat      255
Ala Gln Met Gly Arg Ile Ser His Phe Ser Cys Leu Lys Asp Arg His
             45                  50                  55 gat ttc gga ttc ccc gag gag gag ttt gat ggc cac cag ttc cag aag      303
Asp Phe Gly Phe Pro Glu Glu Glu Phe Asp Gly His Gln Phe Gln Lys
         60                  65                  70 gct caa gcc atc tct gtc ctc cat gag atg atc cag cag acc ttc aat      351
Ala Gln Ala Ile Ser Val Leu His Glu Met Ile Gln Gln Thr Phe Asn
     75                  80                  85 ctc ttc agc aca gag gac tca tct gct gct tgg gaa cag agc ctc cta      399
Leu Phe Ser Thr Glu Asp Ser Ser Ala Ala Trp Glu Gln Ser Leu Leu
 90                  95                 100                 105 gaa aaa ttt tcc act gaa ctt tac cag caa ctg aat gac ctg gaa gca      447
Glu Lys Phe Ser Thr Glu Leu Tyr Gln Gln Leu Asn Asp Leu Glu Ala
                110                 115                 120 tgt gtg ata cag gag gtt ggg gtg gaa gag act ccc ctg atg aat gag      495
Cys Val Ile Gln Glu Val Gly Val Glu Glu Thr Pro Leu Met Asn Glu
            125                 130                 135 gac tcc atc ctg gct gtg agg aaa tac ttc caa aga atc act ctt tat      543
Asp Ser Ile Leu Ala Val Arg Lys Tyr Phe Gln Arg Ile Thr Leu Tyr
        140                 145                 150 cta aca gag aag aaa tac agc cct tgt gcc tgg gag gtt gtc aga gca      591
Leu Thr Glu Lys Lys Tyr Ser Pro Cys Ala Trp Glu Val Val Arg Ala
    155                 160                 165 gaa atc atg aga tcc ctc tcg ttt tca aca aac ttg caa aaa aga tta      639
Glu Ile Met Arg Ser Leu Ser Phe Ser Thr Asn Leu Gln Lys Arg Leu
170                 175                 180                 185 agg agg aag gat tga aacctggttc aacatggaaa tgatcctgat tgactaatac     694
Arg Arg Lys Asp attatctcac actttcatga gttcttccaa tcagcgcttt aaatttgcgc atgctagcta   754 ccnc                                                                758

<210> SEQ ID NO 50
<211> LENGTH: 189
<212> TYPE: PRT
<213> ORGANISM: Homo sapiens

<400> SEQUENCE: 50

Met Ala Leu Ser Phe Ser Leu Leu Met Ala Val Leu Val Leu Ser Tyr
 1               5                  10                  15

Lys Ser Ile Cys Ser Leu Gly Cys Asp Leu Pro Gln Thr His Ser Leu
            20                  25                  30

Gly Asn Arg Arg Ala Leu Ile Leu Leu Ala Gln Met Gly Arg Ile Ser
        35                  40                  45

His Phe Ser Cys Leu Lys Asp Arg His Asp Phe Gly Phe Pro Glu Glu
    50                  55                  60

Glu Phe Asp Gly His Gln Phe Gln Lys Ala Gln Ala Ile Ser Val Leu
65                  70                  75                  80
```

-continued

His Glu Met Ile Gln Gln Thr Phe Asn Leu Phe Ser Thr Glu Asp Ser
                85                  90                  95

Ser Ala Ala Trp Glu Gln Ser Leu Leu Glu Lys Phe Ser Thr Glu Leu
            100                 105                 110

Tyr Gln Gln Leu Asn Asp Leu Glu Ala Cys Val Ile Gln Glu Val Gly
        115                 120                 125

Val Glu Glu Thr Pro Leu Met Asn Glu Asp Ser Ile Leu Ala Val Arg
    130                 135                 140

Lys Tyr Phe Gln Arg Ile Thr Leu Tyr Leu Thr Glu Lys Lys Tyr Ser
145                 150                 155                 160

Pro Cys Ala Trp Glu Val Val Arg Ala Glu Ile Met Arg Ser Leu Ser
                165                 170                 175

Phe Ser Thr Asn Leu Gln Lys Arg Leu Arg Arg Lys Asp
                180                 185

```
<210> SEQ ID NO 51
<211> LENGTH: 896
<212> TYPE: DNA
<213> ORGANISM: Homo sapiens
<220> FEATURE:
<221> NAME/KEY: CDS
<222> LOCATION: (63)..(632)
<220> FEATURE:
<221> NAME/KEY: modified_base
<222> LOCATION: (692)..(692)
<223> OTHER INFORMATION: a, t, c, g, unknown or other
<220> FEATURE:
<221> NAME/KEY: modified_base
<222> LOCATION: (706)..(706)
<223> OTHER INFORMATION: a, t, c, g, unknown or other
<220> FEATURE:
<221> NAME/KEY: modified_base
<222> LOCATION: (728)..(728)
<223> OTHER INFORMATION: a, t, c, g, unknown or other
<220> FEATURE:
<221> NAME/KEY: modified_base
<222> LOCATION: (775)..(775)
<223> OTHER INFORMATION: a, t, c, g, unknown or other
<220> FEATURE:
<221> NAME/KEY: modified_base
<222> LOCATION: (785)..(785)
<223> OTHER INFORMATION: a, t, c, g, unknown or other
<220> FEATURE:
<221> NAME/KEY: modified_base
<222> LOCATION: (806)..(806)
<223> OTHER INFORMATION: a, t, c, g, unknown or other
<220> FEATURE:
<221> NAME/KEY: modified_base
<222> LOCATION: (808)..(808)
<223> OTHER INFORMATION: a, t, c, g, unknown or other
<220> FEATURE:
<221> NAME/KEY: modified_base
<222> LOCATION: (829)..(829)
<223> OTHER INFORMATION: a, t, c, g, unknown or other
<220> FEATURE:
<221> NAME/KEY: modified_base
<222> LOCATION: (843)..(843)
<223> OTHER INFORMATION: a, t, c, g, unknown or other
<220> FEATURE:
<221> NAME/KEY: modified_base
<222> LOCATION: (888)..(888)
<223> OTHER INFORMATION: a, t, c, g, unknown or other
<220> FEATURE:
<221> NAME/KEY: modified_base
<222> LOCATION: (892)..(892)
<223> OTHER INFORMATION: a, t, c, g, unknown or other

<400> SEQUENCE: 51
atgctcgctg cgcaaattaa agcgctgatc tcaagtagcc tagcaatatt ggcaacatcc    60 ca atg gcc ctg tcc ttt tct tta ctg atg gcc gtg ctg gtg ctc agc    107
```

```
    Met Ala Leu Ser Phe Ser Leu Leu Met Ala Val Leu Val Leu Ser
    1               5                   10                  15 tac aaa tcc atc tgt tct ctg ggc tgt gat ctg cct cag acc cac agc    155
Tyr Lys Ser Ile Cys Ser Leu Gly Cys Asp Leu Pro Gln Thr His Ser
                20                  25                  30 ctg ggt aat agg agg gcc ttg ata ctc ctg gca caa gtg gga aga atc    203
Leu Gly Asn Arg Arg Ala Leu Ile Leu Leu Ala Gln Val Gly Arg Ile
            35                  40                  45 tct cat ttc tcc tgc ctg aag gac aga cat gat ttc gga ttc ccc gag    251
Ser His Phe Ser Cys Leu Lys Asp Arg His Asp Phe Gly Phe Pro Glu
        50                  55                  60 gag gag ttt gat ggc cac cag ttc cag aag gct caa gcc atc tct gtc    299
Glu Glu Phe Asp Gly His Gln Phe Gln Lys Ala Gln Ala Ile Ser Val
65                  70                  75 ctc cat gag atg atc cag cag acc ttc aat ctc ttc agc aca gag gac    347
Leu His Glu Met Ile Gln Gln Thr Phe Asn Leu Phe Ser Thr Glu Asp
80                  85                  90                  95 tca tct gct gct tgg gaa cag agc ctc cta gaa aaa ttt tcc act gaa    395
Ser Ser Ala Ala Trp Glu Gln Ser Leu Leu Glu Lys Phe Ser Thr Glu
                100                 105                 110 ctt tac cag caa ctg aat gac ctg gaa gca tgt gtg ata cag gag gtt    443
Leu Tyr Gln Gln Leu Asn Asp Leu Glu Ala Cys Val Ile Gln Glu Val
            115                 120                 125 ggg gtg gaa gag act ccc ctg atg aat gag gac tcc atc ctg gct gtg    491
Gly Val Glu Glu Thr Pro Leu Met Asn Glu Asp Ser Ile Leu Ala Val
        130                 135                 140 agg aaa tac ttc caa aga atc act ctt tat cta aca gag aag aaa tac    539
Arg Lys Tyr Phe Gln Arg Ile Thr Leu Tyr Leu Thr Glu Lys Lys Tyr
145                 150                 155 agc cct tgt gcc tgg gag gtt gtc aga gca gaa atc atg aga tcc ctc    587
Ser Pro Cys Ala Trp Glu Val Val Arg Ala Glu Ile Met Arg Ser Leu
160                 165                 170                 175 tcg ttt tca aca aac ttg caa aaa aga tta agg agg aag gat tga        632
Ser Phe Ser Thr Asn Leu Gln Lys Arg Leu Arg Arg Lys Asp
                180                 185 aacctggttc aacatggaaa tgatctgtat tgactaatac atcgatcgcg cgcagatctn    692
ctgttcgaat tccngatgag ctgcataatc ttttanggta atgcgttggt ccatacaacc    752
ttcttagtac atgcaaccat ttaccggca gangtaaaat agtcaacacg cacngngtta    812
gatattatcc ttgcggngat agattaacgt ntgagcccaa aaagaaacc cttacccaag    872 aaccacttga ggaccncgtn gcct                                          896

<210> SEQ ID NO 52
<211> LENGTH: 189
<212> TYPE: PRT
<213> ORGANISM: Homo sapiens

<400> SEQUENCE: 52

Met Ala Leu Ser Phe Ser Leu Leu Met Ala Val Leu Val Leu Ser Tyr
1               5                   10                  15

Lys Ser Ile Cys Ser Leu Gly Cys Asp Leu Pro Gln Thr His Ser Leu
            20                  25                  30

Gly Asn Arg Arg Ala Leu Ile Leu Leu Ala Gln Val Gly Arg Ile Ser
        35                  40                  45

His Phe Ser Cys Leu Lys Asp Arg His Asp Phe Gly Phe Pro Glu Glu
    50                  55                  60

Glu Phe Asp Gly His Gln Phe Gln Lys Ala Gln Ala Ile Ser Val Leu
65                  70                  75                  80
```

His Glu Met Ile Gln Gln Thr Phe Asn Leu Phe Ser Thr Glu Asp Ser
                85                  90                  95

Ser Ala Ala Trp Glu Gln Ser Leu Leu Glu Lys Phe Ser Thr Glu Leu
            100                 105                 110

Tyr Gln Gln Leu Asn Asp Leu Glu Ala Cys Val Ile Gln Glu Val Gly
        115                 120                 125

Val Glu Glu Thr Pro Leu Met Asn Glu Asp Ser Ile Leu Ala Val Arg
    130                 135                 140

Lys Tyr Phe Gln Arg Ile Thr Leu Tyr Leu Thr Glu Lys Lys Tyr Ser
145                 150                 155                 160

Pro Cys Ala Trp Glu Val Val Arg Ala Glu Ile Met Arg Ser Leu Ser
            165                 170                 175

Phe Ser Thr Asn Leu Gln Lys Arg Leu Arg Arg Lys Asp
        180                 185

```
<210> SEQ ID NO 53
<211> LENGTH: 741
<212> TYPE: DNA
<213> ORGANISM: Homo sapiens
<220> FEATURE:
<221> NAME/KEY: modified_base
<222> LOCATION: (2)..(9)
<223> OTHER INFORMATION: a, t, c, g, unknown or other
<220> FEATURE:
<221> NAME/KEY: modified_base
<222> LOCATION: (12)..(12)
<223> OTHER INFORMATION: a, t, c, g, unknown or other
<220> FEATURE:
<221> NAME/KEY: modified_base
<222> LOCATION: (20)..(21)
<223> OTHER INFORMATION: a, t, c, g, unknown or other
<220> FEATURE:
<221> NAME/KEY: modified_base
<222> LOCATION: (24)..(27)
<223> OTHER INFORMATION: a, t, c, g, unknown or other
<220> FEATURE:
<221> NAME/KEY: modified_base
<222> LOCATION: (33)..(33)
<223> OTHER INFORMATION: a, t, c, g, unknown or other
<220> FEATURE:
<221> NAME/KEY: CDS
<222> LOCATION: (66)..(635)
<220> FEATURE:
<221> NAME/KEY: modified_base
<222> LOCATION: (686)..(686)
<223> OTHER INFORMATION: a, t, c, g, unknown or other
<220> FEATURE:
<221> NAME/KEY: modified_base
<222> LOCATION: (700)..(700)
<223> OTHER INFORMATION: a, t, c, g, unknown or other
<220> FEATURE:
<221> NAME/KEY: modified_base
<222> LOCATION: (708)..(708)
<223> OTHER INFORMATION: a, t, c, g, unknown or other
<220> FEATURE:
<221> NAME/KEY: modified_base
<222> LOCATION: (714)..(717)
<223> OTHER INFORMATION: a, t, c, g, unknown or other
<220> FEATURE:
<221> NAME/KEY: modified_base
<222> LOCATION: (721)..(721)
<223> OTHER INFORMATION: a, t, c, g, unknown or other
<220> FEATURE:
<221> NAME/KEY: modified_base
<222> LOCATION: (724)..(729)
<223> OTHER INFORMATION: a, t, c, g, unknown or other
<220> FEATURE:
<221> NAME/KEY: modified_base
<222> LOCATION: (731)..(740)
<223> OTHER INFORMATION: a, t, c, g, unknown or other
```

-continued

<400> SEQUENCE: 53

```
gnnnnnnnna gngtgtgttn nttnnnngat ctntttgaaa tcccagcaat attggcaaca        60
```

```
tccca atg gcc ctg tcc ttt tct tta ctg atg gcc gtg ctg gtg ctc agc      110
      Met Ala Leu Ser Phe Ser Leu Leu Met Ala Val Leu Val Leu Ser
      1               5                   10                  15 tac aaa tcc atc tgt tct ctg ggc tgt gat ctg cct cag acc cac agc        158
Tyr Lys Ser Ile Cys Ser Leu Gly Cys Asp Leu Pro Gln Thr His Ser
                20                  25                  30 ctg ggt aat agg agg gcc ttg ata ctc ctg gca caa atg gga aga atc        206
Leu Gly Asn Arg Arg Ala Leu Ile Leu Leu Ala Gln Met Gly Arg Ile
            35                  40                  45 tct cat ttc tcc tgc ctg aag gac aga cat gat ttc gga ttc ccc gag        254
Ser His Phe Ser Cys Leu Lys Asp Arg His Asp Phe Gly Phe Pro Glu
        50                  55                  60 gag gag ttt gat ggc cac cag ttc cag aag gct caa gcc atc tct gtc        302
Glu Glu Phe Asp Gly His Gln Phe Gln Lys Ala Gln Ala Ile Ser Val
65                  70                  75 ctc cat gag atg atc cag cag acc ttc aat ctc ttc agc aca gag gac        350
Leu His Glu Met Ile Gln Gln Thr Phe Asn Leu Phe Ser Thr Glu Asp
80                  85                  90                  95 tca tct gct gct tgg gaa cag agc ctc cta gaa aaa ttt tcc act gaa        398
Ser Ser Ala Ala Trp Glu Gln Ser Leu Leu Glu Lys Phe Ser Thr Glu
                100                 105                 110 ctt tac cag caa ctg aat gac ctg gaa gca tgt gtg ata cag gag gtt        446
Leu Tyr Gln Gln Leu Asn Asp Leu Glu Ala Cys Val Ile Gln Glu Val
            115                 120                 125 ggg gtg gaa gag act ccc ctg atg aat gag gac tcc atc ctg gct gtg        494
Gly Val Glu Glu Thr Pro Leu Met Asn Glu Asp Ser Ile Leu Ala Val
        130                 135                 140 agg aaa tac ttc caa aga atc act ctt tat cta ata gag agg aaa tac        542
Arg Lys Tyr Phe Gln Arg Ile Thr Leu Tyr Leu Ile Glu Arg Lys Tyr
145                 150                 155 agc cct tgt gcc tgg gag gtt gtc aga gca gaa atc atg aga tcc ctc        590
Ser Pro Cys Ala Trp Glu Val Val Arg Ala Glu Ile Met Arg Ser Leu
160                 165                 170                 175 tcg ttt tca aca aac ttg caa aaa aga tta agg agg aag gat tga            635
Ser Phe Ser Thr Asn Leu Gln Lys Arg Leu Arg Arg Lys Asp
                180                 185
```

```
aaactggttc aacatggaaa tgatctgtat tgactaatat cagcgctttg natttgcgca      695
```

```
acggncatca aanttcaann nnaacncann nnnncnnnnn nnnnnc                      741
```

<210> SEQ ID NO 54
<211> LENGTH: 189
<212> TYPE: PRT
<213> ORGANISM: Homo sapiens

<400> SEQUENCE: 54

```
Met Ala Leu Ser Phe Ser Leu Leu Met Ala Val Leu Val Leu Ser Tyr
1               5                   10                  15

Lys Ser Ile Cys Ser Leu Gly Cys Asp Leu Pro Gln Thr His Ser Leu
            20                  25                  30

Gly Asn Arg Arg Ala Leu Ile Leu Leu Ala Gln Met Gly Arg Ile Ser
        35                  40                  45

His Phe Ser Cys Leu Lys Asp Arg His Asp Phe Gly Phe Pro Glu Glu
    50                  55                  60

Glu Phe Asp Gly His Gln Phe Gln Lys Ala Gln Ala Ile Ser Val Leu
65                  70                  75                  80
```

```
His Glu Met Ile Gln Gln Thr Phe Asn Leu Phe Ser Thr Glu Asp Ser
                85                  90                  95

Ser Ala Ala Trp Glu Gln Ser Leu Leu Glu Lys Phe Ser Thr Glu Leu
            100                 105                 110

Tyr Gln Gln Leu Asn Asp Leu Glu Ala Cys Val Ile Gln Glu Val Gly
        115                 120                 125

Val Glu Glu Thr Pro Leu Met Asn Glu Asp Ser Ile Leu Ala Val Arg
    130                 135                 140

Lys Tyr Phe Gln Arg Ile Thr Leu Tyr Leu Ile Glu Arg Lys Tyr Ser
145                 150                 155                 160

Pro Cys Ala Trp Glu Val Val Arg Ala Glu Ile Met Arg Ser Leu Ser
                165                 170                 175

Phe Ser Thr Asn Leu Gln Lys Arg Leu Arg Arg Lys Asp
                180                 185

<210> SEQ ID NO 55
<211> LENGTH: 756
<212> TYPE: DNA
<213> ORGANISM: Homo sapiens
<220> FEATURE:
<221> NAME/KEY: CDS
<222> LOCATION: (104)..(673)

<400> SEQUENCE: 55
tatagctagc atgcgcaaat ttaaagcgct gattcagaaa acctagaggc cgaagttcaa      60
ggttatccat ctcaagtagc ctagcaatat ttgcaacatc cca atg gcc ctg tcc     115
                                              Met Ala Leu Ser
                                                1 ttt tct tta ctg acg gcc gtg ctg gtg ctc agc tac aaa tcc atc tgt     163
Phe Ser Leu Leu Thr Ala Val Leu Val Leu Ser Tyr Lys Ser Ile Cys
 5                  10                  15                  20 tct ctg ggc tgt gat ctg cct cag acc cac agc ctg ggt aat agg agg     211
Ser Leu Gly Cys Asp Leu Pro Gln Thr His Ser Leu Gly Asn Arg Arg
                25                  30                  35 gcc ttg ata ctc ctg gca caa atg gga aga atc tct cat ttc tcc tgc     259
Ala Leu Ile Leu Leu Ala Gln Met Gly Arg Ile Ser His Phe Ser Cys
            40                  45                  50 ctg aag gac aga cat gat ttc gga ttc ccc gag gag gag ttt gat ggc     307
Leu Lys Asp Arg His Asp Phe Gly Phe Pro Glu Glu Glu Phe Asp Gly
        55                  60                  65 cac cag ttc cag aag gct caa gcc atc tct gtc ctc cat gag atg atc     355
His Gln Phe Gln Lys Ala Gln Ala Ile Ser Val Leu His Glu Met Ile
    70                  75                  80 cag cag acc ttc aat ctc ttc agc aca gag gac tca tct gct gct tgg     403
Gln Gln Thr Phe Asn Leu Phe Ser Thr Glu Asp Ser Ser Ala Ala Trp
 85                  90                  95                 100 gaa cag agc ctc cta gaa aaa ttt tcc act gaa ctt tac cag caa ctg     451
Glu Gln Ser Leu Leu Glu Lys Phe Ser Thr Glu Leu Tyr Gln Gln Leu
                105                 110                 115 aat gac ctg gaa gca tgt gtg ata cag gag gtt ggg gtg gaa gag act     499
Asn Asp Leu Glu Ala Cys Val Ile Gln Glu Val Gly Val Glu Glu Thr
            120                 125                 130 ccc ctg atg aat gag gac tcc atc ctg gct gtg agg aaa tac ttc caa     547
Pro Leu Met Asn Glu Asp Ser Ile Leu Ala Val Arg Lys Tyr Phe Gln
        135                 140                 145 aga atc act ctt tat cta aca gag aag aaa tac agc cct tgt gcc tgg     595
Arg Ile Thr Leu Tyr Leu Thr Glu Lys Lys Tyr Ser Pro Cys Ala Trp
    150                 155                 160 gag gtt gtc aga gca gaa atc atg aga tcc ctc tcg ttt tca aca aac     643
Glu Val Val Arg Ala Glu Ile Met Arg Ser Leu Ser Phe Ser Thr Asn
```

|     |     |     |     |     |     |     |     |     |     |     |     |     |     |     |     |     |
|---|---|---|---|---|---|---|---|---|---|---|---|---|---|---|---|---|
| Glu | Val | Val | Arg | Ala | Glu | Ile | Met | Arg | Ser | Leu | Ser | Phe | Ser | Thr | Asn |     |
| 165 |     |     |     | 170 |     |     |     | 175 |     |     |     | 180 |     |     |     |     |

```
ttg caa aaa aga tta agg agg aag gat tga aacctggttc aacatggaaa          693
Leu Gln Lys Arg Leu Arg Arg Lys Asp
                185 tgatcctgat tgactaatac attatctcac actttcatga ttcttccaat cgatcgcgcg      753 cac                                                                    756
```

<210> SEQ ID NO 56
<211> LENGTH: 189
<212> TYPE: PRT
<213> ORGANISM: Homo sapiens

<400> SEQUENCE: 56

Met Ala Leu Ser Phe Ser Leu Leu Thr Ala Val Leu Val Leu Ser Tyr
1               5                   10                  15

Lys Ser Ile Cys Ser Leu Gly Cys Asp Leu Pro Gln Thr His Ser Leu
            20                  25                  30

Gly Asn Arg Arg Ala Leu Ile Leu Leu Ala Gln Met Gly Arg Ile Ser
        35                  40                  45

His Phe Ser Cys Leu Lys Asp Arg His Asp Phe Gly Phe Pro Glu Glu
    50                  55                  60

Glu Phe Asp Gly His Gln Phe Gln Lys Ala Gln Ala Ile Ser Val Leu
65                  70                  75                  80

His Glu Met Ile Gln Gln Thr Phe Asn Leu Phe Ser Thr Glu Asp Ser
                85                  90                  95

Ser Ala Ala Trp Glu Gln Ser Leu Leu Glu Lys Phe Ser Thr Glu Leu
            100                 105                 110

Tyr Gln Gln Leu Asn Asp Leu Glu Ala Cys Val Ile Gln Glu Val Gly
        115                 120                 125

Val Glu Glu Thr Pro Leu Met Asn Glu Asp Ser Ile Leu Ala Val Arg
    130                 135                 140

Lys Tyr Phe Gln Arg Ile Thr Leu Tyr Leu Thr Glu Lys Lys Tyr Ser
145                 150                 155                 160

Pro Cys Ala Trp Glu Val Val Arg Ala Glu Ile Met Arg Ser Leu Ser
                165                 170                 175

Phe Ser Thr Asn Leu Gln Lys Arg Leu Arg Arg Lys Asp
            180                 185

<210> SEQ ID NO 57
<211> LENGTH: 878
<212> TYPE: DNA
<213> ORGANISM: Homo sapiens
<220> FEATURE:
<221> NAME/KEY: CDS
<222> LOCATION: (58)..(627)
<220> FEATURE:
<221> NAME/KEY: modified_base
<222> LOCATION: (726)..(726)
<223> OTHER INFORMATION: a, t, c, g, unknown or other
<220> FEATURE:
<221> NAME/KEY: modified_base
<222> LOCATION: (734)..(734)
<223> OTHER INFORMATION: a, t, c, g, unknown or other
<220> FEATURE:
<221> NAME/KEY: modified_base
<222> LOCATION: (740)..(740)
<223> OTHER INFORMATION: a, t, c, g, unknown or other
<220> FEATURE:
<221> NAME/KEY: modified_base
<222> LOCATION: (749)..(749)
<223> OTHER INFORMATION: a, t, c, g, unknown or other

```
<220> FEATURE:
<221> NAME/KEY: modified_base
<222> LOCATION: (793)..(793)
<223> OTHER INFORMATION: a, t, c, g, unknown or other
<220> FEATURE:
<221> NAME/KEY: modified_base
<222> LOCATION: (816)..(816)
<223> OTHER INFORMATION: a, t, c, g, unknown or other
<220> FEATURE:
<221> NAME/KEY: modified_base
<222> LOCATION: (839)..(839)
<223> OTHER INFORMATION: a, t, c, g, unknown or other
<220> FEATURE:
<221> NAME/KEY: modified_base
<222> LOCATION: (842)..(842)
<223> OTHER INFORMATION: a, t, c, g, unknown or other
<220> FEATURE:
<221> NAME/KEY: modified_base
<222> LOCATION: (857)..(857)
<223> OTHER INFORMATION: a, t, c, g, unknown or other

<400> SEQUENCE: 57
ttgacgcccc cttgttaccc ctcatcaacc agcccagcag catcttcggg attccca          57 atg gca ttg ccc ttt gct tta atg atg gcc ctg gtg gtg ctc agc tgc        105
Met Ala Leu Pro Phe Ala Leu Met Met Ala Leu Val Val Leu Ser Cys
1               5                   10                  15 aag tca agc tgc tct ctg ggc tgt aat ctg tct caa acc cac agc ctg        153
Lys Ser Ser Cys Ser Leu Gly Cys Asn Leu Ser Gln Thr His Ser Leu
            20                  25                  30 aat aac agg agg act ttg atg ctc atg gca caa atg agg aga atc tct        201
Asn Asn Arg Arg Thr Leu Met Leu Met Ala Gln Met Arg Arg Ile Ser
        35                  40                  45 cct ttc tcc tgc ctg aag gac aga cat gac ttt gaa ttt ccc cag gag        249
Pro Phe Ser Cys Leu Lys Asp Arg His Asp Phe Glu Phe Pro Gln Glu
    50                  55                  60 gaa ttt gat ggc aac cag ttc cag aaa gct caa gcc atc tct gtc ctc        297
Glu Phe Asp Gly Asn Gln Phe Gln Lys Ala Gln Ala Ile Ser Val Leu
65                  70                  75                  80 cat gag atg atg cag cag acc ttc aat ctc ttc agc aca aag aac tca        345
His Glu Met Met Gln Gln Thr Phe Asn Leu Phe Ser Thr Lys Asn Ser
                85                  90                  95 tct gct gct tgg gat gag gcc ctc cta gaa aaa ttc tac att gaa ctt        393
Ser Ala Ala Trp Asp Glu Ala Leu Leu Glu Lys Phe Tyr Ile Glu Leu
            100                 105                 110 ttc cag caa atg aat gac ctg gaa gcc tgt gtg ata cag gag gtt ggg        441
Phe Gln Gln Met Asn Asp Leu Glu Ala Cys Val Ile Gln Glu Val Gly
        115                 120                 125 gtg gaa gag act ccc ctg atg aat gag gac tcc atc ctg gct gtg aag        489
Val Glu Glu Thr Pro Leu Met Asn Glu Asp Ser Ile Leu Ala Val Lys
    130                 135                 140 aaa tac ttc caa aga atc act ctt tat ctg atg gag aag aaa tac agc        537
Lys Tyr Phe Gln Arg Ile Thr Leu Tyr Leu Met Glu Lys Lys Tyr Ser
145                 150                 155                 160 cct tgt gcc tgg gag gtt gtc aga gca gaa atc atg aga tcc ctc tct        585
Pro Cys Ala Trp Glu Val Val Arg Ala Glu Ile Met Arg Ser Leu Ser
                165                 170                 175 ttt tca aca aac ttg caa aaa aga tta agg agg aag gat tga              627
Phe Ser Thr Asn Leu Gln Lys Arg Leu Arg Arg Lys Asp
            180                 185 aaactggttc atcatggaaa tgattcatca gcgctttaaa tttgcgcatg ctagctatag     687
ttctagaggt cgaaattcac ctcgaaaagc aagctgatna accgatncaa ttnaaggctc     747
cnttttggag cctttttttt ttggagattt tcaaccgtga aaaaantatt attcgcaatt     807
```

-continued

```
ccagctaant cacctcgaaa gcaagcttga tnaanccgtt ccaattaaan gcttcctttg    867 gaggccttt  t                                                         878
```

<210> SEQ ID NO 58
<211> LENGTH: 189
<212> TYPE: PRT
<213> ORGANISM: Homo sapiens

<400> SEQUENCE: 58

```
Met Ala Leu Pro Phe Ala Leu Met Met Ala Leu Val Val Leu Ser Cys
1               5                   10                  15

Lys Ser Ser Cys Ser Leu Gly Cys Asn Leu Ser Gln Thr His Ser Leu
            20                  25                  30

Asn Asn Arg Arg Thr Leu Met Leu Met Ala Gln Met Arg Arg Ile Ser
        35                  40                  45

Pro Phe Ser Cys Leu Lys Asp Arg His Asp Phe Glu Phe Pro Gln Glu
    50                  55                  60

Glu Phe Asp Gly Asn Gln Phe Gln Lys Ala Gln Ala Ile Ser Val Leu
65                  70                  75                  80

His Glu Met Met Gln Gln Thr Phe Asn Leu Phe Ser Thr Lys Asn Ser
                85                  90                  95

Ser Ala Ala Trp Asp Glu Ala Leu Leu Glu Lys Phe Tyr Ile Glu Leu
            100                 105                 110

Phe Gln Gln Met Asn Asp Leu Glu Ala Cys Val Ile Gln Glu Val Gly
        115                 120                 125

Val Glu Glu Thr Pro Leu Met Asn Glu Asp Ser Ile Leu Ala Val Lys
    130                 135                 140

Lys Tyr Phe Gln Arg Ile Thr Leu Tyr Leu Met Glu Lys Lys Tyr Ser
145                 150                 155                 160

Pro Cys Ala Trp Glu Val Val Arg Ala Glu Ile Met Arg Ser Leu Ser
                165                 170                 175

Phe Ser Thr Asn Leu Gln Lys Arg Leu Arg Arg Lys Asp
            180                 185
```

<210> SEQ ID NO 59
<211> LENGTH: 869
<212> TYPE: DNA
<213> ORGANISM: Homo sapiens
<220> FEATURE:
<221> NAME/KEY: modified_base
<222> LOCATION: (19)..(19)
<223> OTHER INFORMATION: a, t, c, g, unknown or other
<220> FEATURE:
<221> NAME/KEY: CDS
<222> LOCATION: (77)..(646)
<220> FEATURE:
<221> NAME/KEY: modified_base
<222> LOCATION: (728)..(728)
<223> OTHER INFORMATION: a, t, c, g, unknown or other
<220> FEATURE:
<221> NAME/KEY: modified_base
<222> LOCATION: (743)..(743)
<223> OTHER INFORMATION: a, t, c, g, unknown or other
<220> FEATURE:
<221> NAME/KEY: modified_base
<222> LOCATION: (780)..(780)
<223> OTHER INFORMATION: a, t, c, g, unknown or other
<220> FEATURE:
<221> NAME/KEY: modified_base
<222> LOCATION: (806)..(806)
<223> OTHER INFORMATION: a, t, c, g, unknown or other
<220> FEATURE:
<221> NAME/KEY: modified_base
<222> LOCATION: (808)..(808)

<223> OTHER INFORMATION: a, t, c, g, unknown or other
<220> FEATURE:
<221> NAME/KEY: modified_base
<222> LOCATION: (844)..(844)
<223> OTHER INFORMATION: a, t, c, g, unknown or other
<220> FEATURE:
<221> NAME/KEY: modified_base
<222> LOCATION: (849)..(849)
<223> OTHER INFORMATION: a, t, c, g, unknown or other
<220> FEATURE:
<221> NAME/KEY: modified_base
<222> LOCATION: (866)..(866)
<223> OTHER INFORMATION: a, t, c, g, unknown or other
<220> FEATURE:
<221> NAME/KEY: modified_base
<222> LOCATION: (869)..(869)
<223> OTHER INFORMATION: a, t, c, g, unknown or other

<400> SEQUENCE: 59

```
tttgaagtcc gttgcgcana ttcaaagcgc tgattacccc tcatcaacca gcccagcagc      60
atcttcggga ttccca atg gca ttg ccc ttt gct tta atg atg gcc ctg gtg     112
                   Met Ala Leu Pro Phe Ala Leu Met Met Ala Leu Val
                   1               5                  10 gtg ctc agc tgc aag tca agc tgc tct ctg ggc tgt aat ctg tct caa       160
Val Leu Ser Cys Lys Ser Ser Cys Ser Leu Gly Cys Asn Leu Ser Gln
        15                  20                  25 acc tac agc ctg aat aac agg agg act ttg atg ctc atg gca caa atg       208
Thr Tyr Ser Leu Asn Asn Arg Arg Thr Leu Met Leu Met Ala Gln Met
 30                  35                  40 agg aga atc tct cct ttc tcc tgc ctg aag gac aga cat gac ttt gaa       256
Arg Arg Ile Ser Pro Phe Ser Cys Leu Lys Asp Arg His Asp Phe Glu
45                  50                  55                  60 ttt ccc cag gag gaa ttt gat ggc aac cag ttc cag aaa gct caa gcc       304
Phe Pro Gln Glu Glu Phe Asp Gly Asn Gln Phe Gln Lys Ala Gln Ala
                 65                  70                  75 atc tct gtc ctc cat gag atg atg cag cag acc ttc aat ctc ttc agc       352
Ile Ser Val Leu His Glu Met Met Gln Gln Thr Phe Asn Leu Phe Ser
     80                  85                  90 aca aag aac tca tct gct gct tgg gat gag acc ctc cta gaa aaa ttc       400
Thr Lys Asn Ser Ser Ala Ala Trp Asp Glu Thr Leu Leu Glu Lys Phe
 95                 100                 105 tac att gaa ctt ttc cag caa atg aat gac ctg gaa gcc tgt gtg ata       448
Tyr Ile Glu Leu Phe Gln Gln Met Asn Asp Leu Glu Ala Cys Val Ile
110                 115                 120 cag gag gtt ggg gtg gaa gag act ccc ctg atg aat gag gac tcc atc       496
Gln Glu Val Gly Val Glu Glu Thr Pro Leu Met Asn Glu Asp Ser Ile
125                 130                 135                 140 ctg gct gtg aag aaa tac ttc caa aga atc act ctt tat ctg atg gag       544
Leu Ala Val Lys Lys Tyr Phe Gln Arg Ile Thr Leu Tyr Leu Met Glu
                145                 150                 155 aag aaa tac agc cct tgt gcc tgg gag gtt gtc aga gca gaa atc atg       592
Lys Lys Tyr Ser Pro Cys Ala Trp Glu Val Val Arg Ala Glu Ile Met
            160                 165                 170 aga tcc ctc tct ttt tca aca aac ttg caa aaa aga tta agg agg aag       640
Arg Ser Leu Ser Phe Ser Thr Asn Leu Gln Lys Arg Leu Arg Arg Lys
            175                 180                 185 gat tga aaactggttc atcatggaaa tgattcatcg atcgcgcgca gatctcctgt        696
Asp tcgaattccg gatgagctgc ataatctttc anggtaatgc gttggtncat acaaccttct     756
tagtacatgc aaccattata ccgncagagg taaatagtc aacacgcacn gnggtagata      816
ttatcccttg cggggataga ttaacgtntg acncaaaaag aaccattacn can            869
```

<210> SEQ ID NO 60
<211> LENGTH: 189
<212> TYPE: PRT
<213> ORGANISM: Homo sapiens

<400> SEQUENCE: 60

```
Met Ala Leu Pro Phe Ala Leu Met Met Ala Leu Val Val Leu Ser Cys
1               5                   10                  15

Lys Ser Ser Cys Ser Leu Gly Cys Asn Leu Ser Gln Thr Tyr Ser Leu
            20                  25                  30

Asn Asn Arg Arg Thr Leu Met Leu Met Ala Gln Met Arg Arg Ile Ser
        35                  40                  45

Pro Phe Ser Cys Leu Lys Asp Arg His Asp Phe Glu Phe Pro Gln Glu
    50                  55                  60

Glu Phe Asp Gly Asn Gln Phe Gln Lys Ala Gln Ala Ile Ser Val Leu
65                  70                  75                  80

His Glu Met Met Gln Gln Thr Phe Asn Leu Phe Ser Thr Lys Asn Ser
                85                  90                  95

Ser Ala Ala Trp Asp Glu Thr Leu Leu Glu Lys Phe Tyr Ile Glu Leu
            100                 105                 110

Phe Gln Gln Met Asn Asp Leu Glu Ala Cys Val Ile Gln Glu Val Gly
        115                 120                 125

Val Glu Glu Thr Pro Leu Met Asn Glu Asp Ser Ile Leu Ala Val Lys
130                 135                 140

Lys Tyr Phe Gln Arg Ile Thr Leu Tyr Leu Met Glu Lys Lys Tyr Ser
145                 150                 155                 160

Pro Cys Ala Trp Glu Val Val Arg Ala Glu Ile Met Arg Ser Leu Ser
                165                 170                 175

Phe Ser Thr Asn Leu Gln Lys Arg Leu Arg Arg Lys Asp
            180                 185
```

<210> SEQ ID NO 61
<211> LENGTH: 679
<212> TYPE: DNA
<213> ORGANISM: Homo sapiens
<220> FEATURE:
<221> NAME/KEY: modified_base
<222> LOCATION: (1)..(1)
<223> OTHER INFORMATION: a, t, c, g, unknown or other
<220> FEATURE:
<221> NAME/KEY: modified_base
<222> LOCATION: (9)..(9)
<223> OTHER INFORMATION: a, t, c, g, unknown or other
<220> FEATURE:
<221> NAME/KEY: modified_base
<222> LOCATION: (11)..(14)
<223> OTHER INFORMATION: a, t, c, g, unknown or other
<220> FEATURE:
<221> NAME/KEY: modified_base
<222> LOCATION: (17)..(17)
<223> OTHER INFORMATION: a, t, c, g, unknown or other
<220> FEATURE:
<221> NAME/KEY: modified_base
<222> LOCATION: (21)..(21)
<223> OTHER INFORMATION: a, t, c, g, unknown or other
<220> FEATURE:
<221> NAME/KEY: modified_base
<222> LOCATION: (30)..(30)
<223> OTHER INFORMATION: a, t, c, g, unknown or other
<220> FEATURE:
<221> NAME/KEY: CDS
<222> LOCATION: (81)..(650)

<400> SEQUENCE: 61

```
nttgttttnt nnnnagngaa ncttttttgcn caaatccaag cgctgatctc aagtagccta      60
gcaatattgg caacatccca atg gcc ctg tcc ttt tct tta ctg atg gcc gtg     113
                      Met Ala Leu Ser Phe Ser Leu Leu Met Ala Val
                       1               5                  10 ctg gtg ctc agc tac aaa tcc atc tgt tct ctg ggc tgt gat ctg cct       161
Leu Val Leu Ser Tyr Lys Ser Ile Cys Ser Leu Gly Cys Asp Leu Pro
             15                  20                  25 cag acc cac agc ctg ggt aat agg agg gcc ttg ata ctc ctg gca caa       209
Gln Thr His Ser Leu Gly Asn Arg Arg Ala Leu Ile Leu Leu Ala Gln
         30                  35                  40 atg gga aga atc tct cct ttc tcc tgc ctg aag gac aga cat gac ttt       257
Met Gly Arg Ile Ser Pro Phe Ser Cys Leu Lys Asp Arg His Asp Phe
     45                  50                  55 gga ttc ccc caa gag gag ttt gat ggc aac cag ttc cag aag gct caa       305
Gly Phe Pro Gln Glu Glu Phe Asp Gly Asn Gln Phe Gln Lys Ala Gln
 60                  65                  70                  75 gcc atc tct gtc ctc cat gag atg atc cag cag acc ttc aat ctc ttc       353
Ala Ile Ser Val Leu His Glu Met Ile Gln Gln Thr Phe Asn Leu Phe
                 80                  85                  90 agc aca aag gac tca tct gct act tgg gaa cag agc ctc cta gaa aaa       401
Ser Thr Lys Asp Ser Ser Ala Thr Trp Glu Gln Ser Leu Leu Glu Lys
             95                 100                 105 ttt ccc act gaa ctt aac cag cag ctg aat gac ctg gaa gcc tgc gtg       449
Phe Pro Thr Glu Leu Asn Gln Gln Leu Asn Asp Leu Glu Ala Cys Val
         110                 115                 120 ata cag gag gtt ggg gtg gaa gag act ccc ctg atg aat gtg gac tcc       497
Ile Gln Glu Val Gly Val Glu Glu Thr Pro Leu Met Asn Val Asp Ser
     125                 130                 135 atc ctg gct gtg aag aaa tac ttc caa aga atc act ctt tat ctg aca       545
Ile Leu Ala Val Lys Lys Tyr Phe Gln Arg Ile Thr Leu Tyr Leu Thr
 140                 145                 150                 155 gag aag aaa tac agc cct tgt gcc tgg gag gtt gtc aga gca gaa atc       593
Glu Lys Lys Tyr Ser Pro Cys Ala Trp Glu Val Val Arg Ala Glu Ile
                 160                 165                 170 atg aga tcc ttc tct tta tca aaa att ttt caa gaa aga tta agg agg       641
Met Arg Ser Phe Ser Leu Ser Lys Ile Phe Gln Glu Arg Leu Arg Arg
             175                 180                 185 aag gaa tga aacctgtttc aacatggaaa tgatctgta                           679
Lys Glu <210> SEQ ID NO 62
<211> LENGTH: 189
<212> TYPE: PRT
<213> ORGANISM: Homo sapiens

<400> SEQUENCE: 62

Met Ala Leu Ser Phe Ser Leu Leu Met Ala Val Leu Val Leu Ser Tyr
 1               5                  10                  15

Lys Ser Ile Cys Ser Leu Gly Cys Asp Leu Pro Gln Thr His Ser Leu
             20                  25                  30

Gly Asn Arg Arg Ala Leu Ile Leu Leu Ala Gln Met Gly Arg Ile Ser
         35                  40                  45

Pro Phe Ser Cys Leu Lys Asp Arg His Asp Phe Gly Phe Pro Gln Glu
     50                  55                  60

Glu Phe Asp Gly Asn Gln Phe Gln Lys Ala Gln Ala Ile Ser Val Leu
 65                  70                  75                  80

His Glu Met Ile Gln Gln Thr Phe Asn Leu Phe Ser Thr Lys Asp Ser
                 85                  90                  95
```

```
Ser Ala Thr Trp Glu Gln Ser Leu Leu Glu Lys Phe Pro Thr Glu Leu
            100                 105                 110
Asn Gln Gln Leu Asn Asp Leu Glu Ala Cys Val Ile Gln Glu Val Gly
        115                 120                 125
Val Glu Glu Thr Pro Leu Met Asn Val Asp Ser Ile Leu Ala Val Lys
130                 135                 140
Lys Tyr Phe Gln Arg Ile Thr Leu Tyr Leu Thr Glu Lys Lys Tyr Ser
145                 150                 155                 160
Pro Cys Ala Trp Glu Val Val Arg Ala Glu Ile Met Arg Ser Phe Ser
                165                 170                 175
Leu Ser Lys Ile Phe Gln Glu Arg Leu Arg Arg Lys Glu
            180                 185

<210> SEQ ID NO 63
<211> LENGTH: 735
<212> TYPE: DNA
<213> ORGANISM: Homo sapiens
<220> FEATURE:
<221> NAME/KEY: CDS
<222> LOCATION: (67)..(636)

<400> SEQUENCE: 63
tatagctagc atgcgcaaat ttaaagcgct gatctcaagt agcctagcaa tattggcaac      60 atccca atg gcc ctg tcc ttt tct tta ctg atg gcc gtg ctg gtg ctc       108
       Met Ala Leu Ser Phe Ser Leu Leu Met Ala Val Leu Val Leu
         1               5                  10 agc tac aaa tcc atc tgt tct ctg ggc tgt gat ctg cct cag acc cac      156
Ser Tyr Lys Ser Ile Cys Ser Leu Gly Cys Asp Leu Pro Gln Thr His
 15                  20                  25                  30 agc ctg ggt aat agg agg gcc ttg ata ctc ctg gca caa atg gga aga      204
Ser Leu Gly Asn Arg Arg Ala Leu Ile Leu Leu Ala Gln Met Gly Arg
                 35                  40                  45 atc tct cct ttc tcc tgc ctg aag gac aga cat gac ttt gga ttc ccc      252
Ile Ser Pro Phe Ser Cys Leu Lys Asp Arg His Asp Phe Gly Phe Pro
             50                  55                  60 cag gag gag ttt gat ggc aac cag ttc cag aag gct caa gcc atc tct      300
Gln Glu Glu Phe Asp Gly Asn Gln Phe Gln Lys Ala Gln Ala Ile Ser
         65                  70                  75 gtc ctc cat gag atg atc cag cag acc ttc aat ctc ttc agc aca aag      348
Val Leu His Glu Met Ile Gln Gln Thr Phe Asn Leu Phe Ser Thr Lys
 80                  85                  90 gac tca tct gct act tgg gaa cag agc ctc cta gaa aaa ttt tcc act      396
Asp Ser Ser Ala Thr Trp Glu Gln Ser Leu Leu Glu Lys Phe Ser Thr
 95                 100                 105                 110 gaa ctt aac cag cag ctg aat gac ctg gaa gcc tgc gtg ata cag gag      444
Glu Leu Asn Gln Gln Leu Asn Asp Leu Glu Ala Cys Val Ile Gln Glu
                115                 120                 125 gtt ggg gtg gaa gag act ccc ctg atg aat gtg gac tcc atc ctg gct      492
Val Gly Val Glu Glu Thr Pro Leu Met Asn Val Asp Ser Ile Leu Ala
            130                 135                 140 gtg aag aaa tac ttc caa aga atc act ctt tat ctg aca gag aag aaa      540
Val Lys Lys Tyr Phe Gln Arg Ile Thr Leu Tyr Leu Thr Glu Lys Lys
145                 150                 155 tac agc cct tgt gcc tgg gag gtt gtc aga gca gaa atc atg aga tcc      588
Tyr Ser Pro Cys Ala Trp Glu Val Val Arg Ala Glu Ile Met Arg Ser
        160                 165                 170 tcc tct tta tca aaa att ttt caa gaa aga tta agg agg aag gaa tga      636
Ser Ser Leu Ser Lys Ile Phe Gln Glu Arg Leu Arg Arg Lys Glu
175                 180                 185
```

```
aacctgtttc aacatggaaa tgatctgtat tgcgtattag tcaatacaga tcatttccct      696
cgccaatatt gctaggctac ttgagatcga tcgcgcgca                             735
```

<210> SEQ ID NO 64
<211> LENGTH: 189
<212> TYPE: PRT
<213> ORGANISM: Homo sapiens

<400> SEQUENCE: 64

```
Met Ala Leu Ser Phe Ser Leu Leu Met Ala Val Leu Val Leu Ser Tyr
1               5                   10                  15

Lys Ser Ile Cys Ser Leu Gly Cys Asp Leu Pro Gln Thr His Ser Leu
            20                  25                  30

Gly Asn Arg Arg Ala Leu Ile Leu Leu Ala Gln Met Gly Arg Ile Ser
        35                  40                  45

Pro Phe Ser Cys Leu Lys Asp Arg His Asp Phe Gly Phe Pro Gln Glu
    50                  55                  60

Glu Phe Asp Gly Asn Gln Phe Gln Lys Ala Gln Ala Ile Ser Val Leu
65                  70                  75                  80

His Glu Met Ile Gln Gln Thr Phe Asn Leu Phe Ser Thr Lys Asp Ser
                85                  90                  95

Ser Ala Thr Trp Glu Gln Ser Leu Leu Glu Lys Phe Ser Thr Glu Leu
            100                 105                 110

Asn Gln Gln Leu Asn Asp Leu Glu Ala Cys Val Ile Gln Glu Val Gly
        115                 120                 125

Val Glu Glu Thr Pro Leu Met Asn Val Asp Ser Ile Leu Ala Val Lys
    130                 135                 140

Lys Tyr Phe Gln Arg Ile Thr Leu Tyr Leu Thr Glu Lys Lys Tyr Ser
145                 150                 155                 160

Pro Cys Ala Trp Glu Val Val Arg Ala Glu Ile Met Arg Ser Ser Ser
                165                 170                 175

Leu Ser Lys Ile Phe Gln Glu Arg Leu Arg Arg Lys Glu
            180                 185
```

<210> SEQ ID NO 65
<211> LENGTH: 661
<212> TYPE: DNA
<213> ORGANISM: Homo sapiens
<220> FEATURE:
<221> NAME/KEY: modified_base
<222> LOCATION: (1)..(1)
<223> OTHER INFORMATION: a, t, c, g, unknown or other
<220> FEATURE:
<221> NAME/KEY: modified_base
<222> LOCATION: (4)..(4)
<223> OTHER INFORMATION: a, t, c, g, unknown or other
<220> FEATURE:
<221> NAME/KEY: CDS
<222> LOCATION: (56)..(625)

<400> SEQUENCE: 65

```
ntanctagca tgcgcaaatt taaagcgctg atcagcagca tccacaacat ctaca atg      58
                                                              Met
                                                              1 gcc ttg act ttt tat tta ctg gtg gcc cta gtg gtg ctc agc tac aag      106
Ala Leu Thr Phe Tyr Leu Leu Val Ala Leu Val Val Leu Ser Tyr Lys
            5                   10                  15 tca ttc agc tct ctg ggc tgt gat ctg cct cag act cac agc ctg ggt      154
Ser Phe Ser Ser Leu Gly Cys Asp Leu Pro Gln Thr His Ser Leu Gly
        20                  25                  30
```

```
aac agg agg gcc ttg ata ctc ctg gca caa atg cga aga atc tct cct    202
Asn Arg Arg Ala Leu Ile Leu Leu Ala Gln Met Arg Arg Ile Ser Pro
    35                  40                  45 ttc tcc tgc ctg aag gac aga cat gac ttt gaa ttc ccc cag gag gag    250
Phe Ser Cys Leu Lys Asp Arg His Asp Phe Glu Phe Pro Gln Glu Glu
 50                  55                  60                  65 ttt gat gat aaa cag ttc cag aag gct caa gcc atc tct gtc ctc cat    298
Phe Asp Asp Lys Gln Phe Gln Lys Ala Gln Ala Ile Ser Val Leu His
                 70                  75                  80 gag atg atc cag cgg acc ttc aac ctc ttc agc aca aag gac tca tct    346
Glu Met Ile Gln Arg Thr Phe Asn Leu Phe Ser Thr Lys Asp Ser Ser
             85                  90                  95 gct gct ttg gat gag acc ctt cta gat gaa ttc tac atc gaa ctt gac    394
Ala Ala Leu Asp Glu Thr Leu Leu Asp Glu Phe Tyr Ile Glu Leu Asp
         100                 105                 110 cag cag ctg aat gac ctg gag tcc tgt gtg gtg cag gaa gtg ggg gtg    442
Gln Gln Leu Asn Asp Leu Glu Ser Cys Val Val Gln Glu Val Gly Val
     115                 120                 125 ata gag tct ccc ctg atg tac gag gac tcc atc ctg gct gtg agg aaa    490
Ile Glu Ser Pro Leu Met Tyr Glu Asp Ser Ile Leu Ala Val Arg Lys
 130                 135                 140                 145 tac ttc caa aga atc act cta tat ctg aca gag aag aaa tac agc tct    538
Tyr Phe Gln Arg Ile Thr Leu Tyr Leu Thr Glu Lys Lys Tyr Ser Ser
                 150                 155                 160 tgt gcc tgg gag gtt gtc aga gca gaa atc atg aga tcc ttc tct tta    586
Cys Ala Trp Glu Val Val Arg Ala Glu Ile Met Arg Ser Phe Ser Leu
             165                 170                 175 tca atc aac ttg caa aaa aga ttg aag agt aag gaa tga gacctggtac     635
Ser Ile Asn Leu Gln Lys Arg Leu Lys Ser Lys Glu
         180                 185 aacacggaaa tgatcgatcg cgcgca                                       661

<210> SEQ ID NO 66
<211> LENGTH: 189
<212> TYPE: PRT
<213> ORGANISM: Homo sapiens

<400> SEQUENCE: 66

Met Ala Leu Thr Phe Tyr Leu Leu Val Ala Leu Val Val Leu Ser Tyr
 1               5                  10                  15

Lys Ser Phe Ser Ser Leu Gly Cys Asp Leu Pro Gln Thr His Ser Leu
             20                  25                  30

Gly Asn Arg Arg Ala Leu Ile Leu Leu Ala Gln Met Arg Arg Ile Ser
         35                  40                  45

Pro Phe Ser Cys Leu Lys Asp Arg His Asp Phe Glu Phe Pro Gln Glu
     50                  55                  60

Glu Phe Asp Asp Lys Gln Phe Gln Lys Ala Gln Ala Ile Ser Val Leu
 65                  70                  75                  80

His Glu Met Ile Gln Arg Thr Phe Asn Leu Phe Ser Thr Lys Asp Ser
                 85                  90                  95

Ser Ala Ala Leu Asp Glu Thr Leu Leu Asp Glu Phe Tyr Ile Glu Leu
             100                 105                 110

Asp Gln Gln Leu Asn Asp Leu Glu Ser Cys Val Val Gln Glu Val Gly
         115                 120                 125

Val Ile Glu Ser Pro Leu Met Tyr Glu Asp Ser Ile Leu Ala Val Arg
     130                 135                 140

Lys Tyr Phe Gln Arg Ile Thr Leu Tyr Leu Thr Glu Lys Lys Tyr Ser
 145                 150                 155                 160
```

```
Ser Cys Ala Trp Glu Val Val Arg Ala Glu Ile Met Arg Ser Phe Ser
            165                 170                 175

Leu Ser Ile Asn Leu Gln Lys Arg Leu Lys Ser Lys Glu
            180                 185

<210> SEQ ID NO 67
<211> LENGTH: 661
<212> TYPE: DNA
<213> ORGANISM: Homo sapiens
<220> FEATURE:
<221> NAME/KEY: CDS
<222> LOCATION: (38)..(607)

<400> SEQUENCE: 67
tgcgcgcgat cgatcagcag catccacaac atctaca atg gcc ttg act ttt tat        55
                                         Met Ala Leu Thr Phe Tyr
                                          1               5 tta ctg gtg gcc cta gtg gtg ctc agc tac aag tca ttc agc tct ctg        103
Leu Leu Val Ala Leu Val Val Leu Ser Tyr Lys Ser Phe Ser Ser Leu
            10                  15                  20 ggc tgt gat ctg cct cag act cac agc ctg ggt aac agg agg gcc ttg        151
Gly Cys Asp Leu Pro Gln Thr His Ser Leu Gly Asn Arg Arg Ala Leu
        25                  30                  35 ata ctc ctg gca caa atg cga aga atc tct cct ttc tcc tgc ctg aag        199
Ile Leu Leu Ala Gln Met Arg Arg Ile Ser Pro Phe Ser Cys Leu Lys
    40                  45                  50 gac agc cat gac ttt gaa ttc ccc cag gag gag ttt gat gat aaa cag        247
Asp Ser His Asp Phe Glu Phe Pro Gln Glu Glu Phe Asp Asp Lys Gln
55                  60                  65                  70 ttc cag aag gct caa gcc atc tct gtc ctc cat gag atg atc cag cag        295
Phe Gln Lys Ala Gln Ala Ile Ser Val Leu His Glu Met Ile Gln Gln
                75                  80                  85 acc ttc aac ctc ttc agc aca aag gac tca tct gct gct ttg gat gag        343
Thr Phe Asn Leu Phe Ser Thr Lys Asp Ser Ser Ala Ala Leu Asp Glu
            90                  95                  100 acc ctt cta gat gaa ttc tac atc gaa ctt gac cag cag ctg aat gac        391
Thr Leu Leu Asp Glu Phe Tyr Ile Glu Leu Asp Gln Gln Leu Asn Asp
        105                 110                 115 ctg gag tcc tgt gtg atg cag gaa gtg ggg gtg ata gag tct ccc ctg        439
Leu Glu Ser Cys Val Met Gln Glu Val Gly Val Ile Glu Ser Pro Leu
    120                 125                 130 atg tac gag gac tcc atc ctg gct gtg agg aaa tac ttc caa aga atc        487
Met Tyr Glu Asp Ser Ile Leu Ala Val Arg Lys Tyr Phe Gln Arg Ile
135                 140                 145                 150 act cta tat ctg aca gag aag aaa tac agc tct tgt gcc tgg gag gtt        535
Thr Leu Tyr Leu Thr Glu Lys Lys Tyr Ser Ser Cys Ala Trp Glu Val
                155                 160                 165 gtc aga gca gaa atc atg aga tcc ttc tct tta tca atc aac ttg caa        583
Val Arg Ala Glu Ile Met Arg Ser Phe Ser Leu Ser Ile Asn Leu Gln
            170                 175                 180 aaa aga ttg aag agt aag gaa tga gacctggtac aacacggaaa tgatcagcgc       637
Lys Arg Leu Lys Ser Lys Glu
        185 tttaaatttg cgcatgctag ctat                                             661

<210> SEQ ID NO 68
<211> LENGTH: 189
<212> TYPE: PRT
<213> ORGANISM: Homo sapiens

<400> SEQUENCE: 68
```

Met Ala Leu Thr Phe Tyr Leu Leu Val Ala Leu Val Val Leu Ser Tyr
1               5                   10                  15

Lys Ser Phe Ser Ser Leu Gly Cys Asp Leu Pro Gln Thr His Ser Leu
            20                  25                  30

Gly Asn Arg Arg Ala Leu Ile Leu Leu Ala Gln Met Arg Arg Ile Ser
        35                  40                  45

Pro Phe Ser Cys Leu Lys Asp Ser His Asp Phe Glu Phe Pro Gln Glu
    50                  55                  60

Glu Phe Asp Asp Lys Gln Phe Gln Lys Ala Gln Ala Ile Ser Val Leu
65              70                  75                  80

His Glu Met Ile Gln Gln Thr Phe Asn Leu Phe Ser Thr Lys Asp Ser
                85                  90                  95

Ser Ala Ala Leu Asp Glu Thr Leu Leu Asp Glu Phe Tyr Ile Glu Leu
            100                 105                 110

Asp Gln Gln Leu Asn Asp Leu Glu Ser Cys Val Met Gln Glu Val Gly
        115                 120                 125

Val Ile Glu Ser Pro Leu Met Tyr Glu Asp Ser Ile Leu Ala Val Arg
    130                 135                 140

Lys Tyr Phe Gln Arg Ile Thr Leu Tyr Leu Thr Glu Lys Lys Tyr Ser
145             150                 155                 160

Ser Cys Ala Trp Glu Val Val Arg Ala Glu Ile Met Arg Ser Phe Ser
                165                 170                 175

Leu Ser Ile Asn Leu Gln Lys Arg Leu Lys Ser Lys Glu
            180                 185

<210> SEQ ID NO 69
<211> LENGTH: 570
<212> TYPE: DNA
<213> ORGANISM: Homo sapiens
<220> FEATURE:
<221> NAME/KEY: CDS
<222> LOCATION: (1)..(567)

<400> SEQUENCE: 69 atg gcc ttg tcc ttt tct tta ctg atg gtc gtg ctg gta ctc agc tac      48
Met Ala Leu Ser Phe Ser Leu Leu Met Val Val Leu Val Leu Ser Tyr
1               5                   10                  15 aaa tcc atc tgc tct ctg ggc tgt gat ctg cct cag acc cac agc ctg      96
Lys Ser Ile Cys Ser Leu Gly Cys Asp Leu Pro Gln Thr His Ser Leu
            20                  25                  30 cgt aat agg agg gcc ttg ata ctc ctg gca caa atg gga aga atc tct     144
Arg Asn Arg Arg Ala Leu Ile Leu Leu Ala Gln Met Gly Arg Ile Ser
        35                  40                  45 cct ttc tcc tgc ttg aag gac aga cat gaa ttc aga ttc cca gag gag     192
Pro Phe Ser Cys Leu Lys Asp Arg His Glu Phe Arg Phe Pro Glu Glu
    50                  55                  60 gag ttt gat ggc cac cag ttc cag aag act caa gcc atc tct gtc ctc     240
Glu Phe Asp Gly His Gln Phe Gln Lys Thr Gln Ala Ile Ser Val Leu
65              70                  75                  80 cat gag atg atc cag cag acc ttc aat ctc ttc agc aca gag gac tca     288
His Glu Met Ile Gln Gln Thr Phe Asn Leu Phe Ser Thr Glu Asp Ser
                85                  90                  95 tct gct gct tgg gaa cag agc ctc cta gaa aaa ttt tcc act gaa ctt     336
Ser Ala Ala Trp Glu Gln Ser Leu Leu Glu Lys Phe Ser Thr Glu Leu
            100                 105                 110 tac cag caa ctg aat gac ctg gaa gca tgt gtg ata cag gag gtt ggg     384
Tyr Gln Gln Leu Asn Asp Leu Glu Ala Cys Val Ile Gln Glu Val Gly
        115                 120                 125

```
gtg gaa gag act ccc ctg atg aat gag gac tcc atc ctg gct gtg agg      432
Val Glu Glu Thr Pro Leu Met Asn Glu Asp Ser Ile Leu Ala Val Arg
130                 135                 140 aaa tac ttc caa aga atc act ctt tat cta aca gag aag aaa tac agc      480
Lys Tyr Phe Gln Arg Ile Thr Leu Tyr Leu Thr Glu Lys Lys Tyr Ser
145                 150                 155                 160 cct tgt gcc tgg gag gtt gtc aga gca gaa atc atg aga tcc ctc tcg      528
Pro Cys Ala Trp Glu Val Val Arg Ala Glu Ile Met Arg Ser Leu Ser
                165                 170                 175 ttt tca aca aac ttg caa aaa aga tta agg agg aag gat tga              570
Phe Ser Thr Asn Leu Gln Lys Arg Leu Arg Arg Lys Asp
                180                 185
```

<210> SEQ ID NO 70
<211> LENGTH: 189
<212> TYPE: PRT
<213> ORGANISM: Homo sapiens

<400> SEQUENCE: 70

```
Met Ala Leu Ser Phe Ser Leu Leu Met Val Val Leu Val Leu Ser Tyr
1               5                   10                  15

Lys Ser Ile Cys Ser Leu Gly Cys Asp Leu Pro Gln Thr His Ser Leu
            20                  25                  30

Arg Asn Arg Arg Ala Leu Ile Leu Leu Ala Gln Met Gly Arg Ile Ser
        35                  40                  45

Pro Phe Ser Cys Leu Lys Asp Arg His Glu Phe Arg Phe Pro Glu Glu
    50                  55                  60

Glu Phe Asp Gly His Gln Phe Gln Lys Thr Gln Ala Ile Ser Val Leu
65                  70                  75                  80

His Glu Met Ile Gln Gln Thr Phe Asn Leu Phe Ser Thr Glu Asp Ser
                85                  90                  95

Ser Ala Ala Trp Glu Gln Ser Leu Leu Glu Lys Phe Ser Thr Glu Leu
            100                 105                 110

Tyr Gln Gln Leu Asn Asp Leu Glu Ala Cys Val Ile Gln Glu Val Gly
        115                 120                 125

Val Glu Glu Thr Pro Leu Met Asn Glu Asp Ser Ile Leu Ala Val Arg
    130                 135                 140

Lys Tyr Phe Gln Arg Ile Thr Leu Tyr Leu Thr Glu Lys Lys Tyr Ser
145                 150                 155                 160

Pro Cys Ala Trp Glu Val Val Arg Ala Glu Ile Met Arg Ser Leu Ser
                165                 170                 175

Phe Ser Thr Asn Leu Gln Lys Arg Leu Arg Arg Lys Asp
            180                 185
```

<210> SEQ ID NO 71
<211> LENGTH: 679
<212> TYPE: DNA
<213> ORGANISM: Homo sapiens
<220> FEATURE:
<221> NAME/KEY: modified_base
<222> LOCATION: (1)..(1)
<223> OTHER INFORMATION: a, t, c, g, unknown or other
<220> FEATURE:
<221> NAME/KEY: modified_base
<222> LOCATION: (9)..(9)
<223> OTHER INFORMATION: a, t, c, g, unknown or other
<220> FEATURE:
<221> NAME/KEY: modified_base
<222> LOCATION: (11)..(14)
<223> OTHER INFORMATION: a, t, c, g, unknown or other
<220> FEATURE:

```
<221> NAME/KEY: modified_base
<222> LOCATION: (17)..(17)
<223> OTHER INFORMATION: a, t, c, g, unknown or other
<220> FEATURE:
<221> NAME/KEY: modified_base
<222> LOCATION: (21)..(21)
<223> OTHER INFORMATION: a, t, c, g, unknown or other
<220> FEATURE:
<221> NAME/KEY: modified_base
<222> LOCATION: (30)..(30)
<223> OTHER INFORMATION: a, t, c, g, unknown or other
<220> FEATURE:
<221> NAME/KEY: CDS
<222> LOCATION: (81)..(650)

<400> SEQUENCE: 71
nttgttttnt nnnnagngaa ncttttttgcn caaatccaag cgctgatctc aagtagccta      60
gcaatattgg caacatccca atg gcc ctg tcc ttt tct tta ctg atg gcc gtg     113
                         Met Ala Leu Ser Phe Ser Leu Leu Met Ala Val
                         1               5                  10 ctg gtg ctc agc tac aaa tcc atc tgt tct ctg ggc tgt gat ctg cct       161
Leu Val Leu Ser Tyr Lys Ser Ile Cys Ser Leu Gly Cys Asp Leu Pro
             15                  20                  25 cag acc cac agc ctg ggt aat agg agg gcc ttg ata ctc ctg gca caa       209
Gln Thr His Ser Leu Gly Asn Arg Arg Ala Leu Ile Leu Leu Ala Gln
         30                  35                  40 atg gga aga atc tct cct ttc tcc tgc ctg aag gac aga cat gac ttt       257
Met Gly Arg Ile Ser Pro Phe Ser Cys Leu Lys Asp Arg His Asp Phe
45                   50                  55 gga ttc ccc caa gag gag ttt gat ggc aac cag ttc cag aag gct caa       305
Gly Phe Pro Gln Glu Glu Phe Asp Gly Asn Gln Phe Gln Lys Ala Gln
 60                  65                  70                  75 gcc atc tct gtc ctc cat gag atg atc cag cag acc ttc aat ctc ttc       353
Ala Ile Ser Val Leu His Glu Met Ile Gln Gln Thr Phe Asn Leu Phe
             80                  85                  90 agc aca aag gac tca tct gct act tgg gaa cag agc ctc cta gaa aaa       401
Ser Thr Lys Asp Ser Ser Ala Thr Trp Glu Gln Ser Leu Leu Glu Lys
         95                  100                 105 ttt ccc act gaa ctt aac cag cag ctg aat gac ctg gaa gcc tgc gtg       449
Phe Pro Thr Glu Leu Asn Gln Gln Leu Asn Asp Leu Glu Ala Cys Val
    110                 115                 120 ata cag gag gtt ggg gtg gaa gag act ccc ctg atg aat gtg gac tcc       497
Ile Gln Glu Val Gly Val Glu Glu Thr Pro Leu Met Asn Val Asp Ser
125                 130                 135 atc ctg gct gtg aag aaa tac ttc caa aga atc act ctt tat ctg aca       545
Ile Leu Ala Val Lys Lys Tyr Phe Gln Arg Ile Thr Leu Tyr Leu Thr
140                 145                 150                 155 gag aag aaa tac agc cct tgt gcc tgg gag gtt gtc aga gca gaa atc       593
Glu Lys Lys Tyr Ser Pro Cys Ala Trp Glu Val Val Arg Ala Glu Ile
                160                 165                 170 atg aga tcc ttc tct tta tca aaa att ttt caa gaa aga tta agg agg       641
Met Arg Ser Phe Ser Leu Ser Lys Ile Phe Gln Glu Arg Leu Arg Arg
                175                 180                 185 aag gaa tga aacctgtttc aacatggaaa tgatctgta                           679
Lys Glu <210> SEQ ID NO 72
<211> LENGTH: 189
<212> TYPE: PRT
<213> ORGANISM: Homo sapiens

<400> SEQUENCE: 72

Met Ala Leu Ser Phe Ser Leu Leu Met Ala Val Leu Val Leu Ser Tyr
```

```
              1               5                  10                 15
           Lys Ser Ile Cys Ser Leu Gly Cys Asp Leu Pro Gln Thr His Ser Leu
                           20                 25                 30

Gly Asn Arg Arg Ala Leu Ile Leu Leu Ala Gln Met Gly Arg Ile Ser
                           35                 40                 45

Pro Phe Ser Cys Leu Lys Asp Arg His Asp Phe Gly Phe Pro Gln Glu
                           50                 55                 60

Glu Phe Asp Gly Asn Gln Phe Gln Lys Ala Gln Ala Ile Ser Val Leu
            65                 70                 75                 80

His Glu Met Ile Gln Gln Thr Phe Asn Leu Phe Ser Thr Lys Asp Ser
                           85                 90                 95

Ser Ala Thr Trp Glu Gln Ser Leu Leu Glu Lys Phe Pro Thr Glu Leu
                           100                105                110

Asn Gln Gln Leu Asn Asp Leu Glu Ala Cys Val Ile Gln Glu Val Gly
                           115                120                125

Val Glu Glu Thr Pro Leu Met Asn Val Asp Ser Ile Leu Ala Val Lys
                           130                135                140

Lys Tyr Phe Gln Arg Ile Thr Leu Tyr Leu Thr Glu Lys Lys Tyr Ser
           145                150                155                160

Pro Cys Ala Trp Glu Val Val Arg Ala Glu Ile Met Arg Ser Phe Ser
                           165                170                175

Leu Ser Lys Ile Phe Gln Glu Arg Leu Arg Arg Lys Glu
                           180                185
```

<210> SEQ ID NO 73
<211> LENGTH: 523
<212> TYPE: DNA
<213> ORGANISM: Homo sapiens
<220> FEATURE:
<221> NAME/KEY: CDS
<222> LOCATION: (14)..(514)

<400> SEQUENCE: 73

```
agatcttctg atg tgc gac ctg ccg cag acc cac tcc ctg cgt aac cgt         49
               Cys Asp Leu Pro Gln Thr His Ser Leu Arg Asn Arg
                 1               5                  10 cgt gct ctg atc ctg ctg gct cag atg ggt cgt atc tcc ccg ttc tcc        97
Arg Ala Leu Ile Leu Leu Ala Gln Met Gly Arg Ile Ser Pro Phe Ser
         15                  20                  25 tgc ctg aaa gac cgt cac gaa ttc cgt ttc ccg gaa gaa gaa ttc gat       145
Cys Leu Lys Asp Arg His Glu Phe Arg Phe Pro Glu Glu Glu Phe Asp
     30                  35                  40 ggc cac cag ttc cag aaa acc cag gct atc tcc gtt ctg cac gaa atg       193
Gly His Gln Phe Gln Lys Thr Gln Ala Ile Ser Val Leu His Glu Met
 45                  50                  55                  60 atc cag cag acc ttc aac ctg ttc tcc acc gaa gac tcc tcc gcg gct       241
Ile Gln Gln Thr Phe Asn Leu Phe Ser Thr Glu Asp Ser Ser Ala Ala
                 65                  70                  75 tgg gaa cag tcc ctg ctg gaa aaa ttc tcc acc gaa ctg tac cag cag       289
Trp Glu Gln Ser Leu Leu Glu Lys Phe Ser Thr Glu Leu Tyr Gln Gln
             80                  85                  90 ctg aac gac ctg gaa gct tgc gtt atc cag gaa gtt ggt gtt gaa gaa       337
Leu Asn Asp Leu Glu Ala Cys Val Ile Gln Glu Val Gly Val Glu Glu
         95                 100                 105 acc ccg ctg atg aac gaa gac tcc atc ctg gct gtt cgt aaa tac ttc       385
Thr Pro Leu Met Asn Glu Asp Ser Ile Leu Ala Val Arg Lys Tyr Phe
    110                 115                 120 cag cgt atc acc ctg tac ctg acc gaa aaa aaa tac tcc ccg tgc gca       433
```

```
Gln Arg Ile Thr Leu Tyr Leu Thr Glu Lys Lys Tyr Ser Pro Cys Ala
125                 130                 135                 140 tgg gaa gtt gtt cgt gct gaa atc atg cgt tcc ctg tcc ttc tcc acc        481
Trp Glu Val Val Arg Ala Glu Ile Met Arg Ser Leu Ser Phe Ser Thr
                145                 150                 155 aac ctg cag aaa cgt ctg cgt cgt aaa gac tga tgatctaga                   523
Asn Leu Gln Lys Arg Leu Arg Arg Lys Asp
            160                 165

<210> SEQ ID NO 74
<211> LENGTH: 166
<212> TYPE: PRT
<213> ORGANISM: Homo sapiens

<400> SEQUENCE: 74

Cys Asp Leu Pro Gln Thr His Ser Leu Arg Asn Arg Arg Ala Leu Ile
1               5                   10                  15

Leu Leu Ala Gln Met Gly Arg Ile Ser Pro Phe Ser Cys Leu Lys Asp
            20                  25                  30

Arg His Glu Phe Arg Phe Pro Glu Glu Glu Phe Asp Gly His Gln Phe
        35                  40                  45

Gln Lys Thr Gln Ala Ile Ser Val Leu His Glu Met Ile Gln Gln Thr
    50                  55                  60

Phe Asn Leu Phe Ser Thr Glu Asp Ser Ser Ala Ala Trp Glu Gln Ser
65                  70                  75                  80

Leu Leu Glu Lys Phe Ser Thr Glu Leu Tyr Gln Gln Leu Asn Asp Leu
                85                  90                  95

Glu Ala Cys Val Ile Gln Glu Val Gly Val Glu Glu Thr Pro Leu Met
            100                 105                 110

Asn Glu Asp Ser Ile Leu Ala Val Arg Lys Tyr Phe Gln Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Leu Ser Phe Ser Thr Asn Leu Gln Lys
145                 150                 155                 160

Arg Leu Arg Arg Lys Asp
                165

<210> SEQ ID NO 75
<211> LENGTH: 523
<212> TYPE: DNA
<213> ORGANISM: Homo sapiens
<220> FEATURE:
<221> NAME/KEY: CDS
<222> LOCATION: (14)..(514)

<400> SEQUENCE: 75
agatcttctg atg tgc aac ctg tcc cag acc tac tcc ctg aac aac cgt        49
        Cys Asn Leu Ser Gln Thr Tyr Ser Leu Asn Asn Arg
        1               5                   10 cgt acc ctg atg ctg atg gct cag atg cgt cgt atc tcc ccg ttc tcc       97
Arg Thr Leu Met Leu Met Ala Gln Met Arg Arg Ile Ser Pro Phe Ser
            15                  20                  25 tgc ctg aaa gac cgt cac gac ttc gaa ttc ccg cag gaa gaa ttc gac      145
Cys Leu Lys Asp Arg His Asp Phe Glu Phe Pro Gln Glu Glu Phe Asp
        30                  35                  40 ggt aac cag ttc cag aaa gct cag gct atc tcc gtt ctg cac gaa atg      193
Gly Asn Gln Phe Gln Lys Ala Gln Ala Ile Ser Val Leu His Glu Met
45                  50                  55                  60
```

```
atg cag cag acc ttc aac ctg ttc tcc acc aaa aac tcc tct gca gct      241
Met Gln Gln Thr Phe Asn Leu Phe Ser Thr Lys Asn Ser Ser Ala Ala
             65                  70                  75 tgg gac gaa acc ctg ctg gaa aaa ttc tac atc gaa ctg ttc cag cag      289
Trp Asp Glu Thr Leu Leu Glu Lys Phe Tyr Ile Glu Leu Phe Gln Gln
         80                  85                  90 atg aac gac ctg gaa gct tgc gtt atc cag gaa gtt ggt gtt gaa gaa      337
Met Asn Asp Leu Glu Ala Cys Val Ile Gln Glu Val Gly Val Glu Glu
     95                 100                 105 acc ccg ctg atg aac gaa gac tcc atc ctg gct gtt aaa aaa tac ttc      385
Thr Pro Leu Met Asn Glu Asp Ser Ile Leu Ala Val Lys Lys Tyr Phe
110                 115                 120 cag cgt atc acc ctg tac ctg atg gaa aaa aaa tac tcc ccg tgc gca      433
Gln Arg Ile Thr Leu Tyr Leu Met Glu Lys Lys Tyr Ser Pro Cys Ala
125                 130                 135                 140 tgg gaa gtt gtt cgt gct gaa atc atg cgt tcc ctg tcc ttc tcc acc      481
Trp Glu Val Val Arg Ala Glu Ile Met Arg Ser Leu Ser Phe Ser Thr
                145                 150                 155 aac ctg cag aaa cgt ctg cgt cgt aaa gac tga tgatctaga                523
Asn Leu Gln Lys Arg Leu Arg Arg Lys Asp
                160                 165

<210> SEQ ID NO 76
<211> LENGTH: 166
<212> TYPE: PRT
<213> ORGANISM: Homo sapiens

<400> SEQUENCE: 76

Cys Asn Leu Ser Gln Thr Tyr Ser Leu Asn Asn Arg Arg Thr Leu Met
1               5                   10                  15

Leu Met Ala Gln Met Arg Arg Ile Ser Pro Phe Ser Cys Leu Lys Asp
            20                  25                  30

Arg His Asp Phe Glu Phe Pro Gln Glu Glu Phe Asp Gly Asn Gln Phe
        35                  40                  45

Gln Lys Ala Gln Ala Ile Ser Val Leu His Glu Met Met Gln Gln Thr
    50                  55                  60

Phe Asn Leu Phe Ser Thr Lys Asn Ser Ser Ala Ala Trp Asp Glu Thr
65                  70                  75                  80

Leu Leu Glu Lys Phe Tyr Ile Glu Leu Phe Gln Gln Met Asn Asp Leu
                85                  90                  95

Glu Ala Cys Val Ile Gln Glu Val Gly Val Glu Glu Thr Pro Leu Met
            100                 105                 110

Asn Glu Asp Ser Ile Leu Ala Val Lys Lys Tyr Phe Gln Arg Ile Thr
        115                 120                 125

Leu Tyr Leu Met Glu Lys Lys Tyr Ser Pro Cys Ala Trp Glu Val Val
    130                 135                 140

Arg Ala Glu Ile Met Arg Ser Leu Ser Phe Ser Thr Asn Leu Gln Lys
145                 150                 155                 160

Arg Leu Arg Arg Lys Asp
                165

<210> SEQ ID NO 77
<211> LENGTH: 501
<212> TYPE: DNA
<213> ORGANISM: Homo sapiens
<220> FEATURE:
<221> NAME/KEY: CDS
<222> LOCATION: (1)..(498)

<400> SEQUENCE: 77
```

```
tgt gat ctg cct cag acc cac agc ctg cgt aat agg agg gcc ttg ata      48
Cys Asp Leu Pro Gln Thr His Ser Leu Arg Asn Arg Arg Ala Leu Ile
 1               5                  10                  15 ctc ctg gca caa atg gga aga atc tct cct ttc tcc tgc ttg aag gac      96
Leu Leu Ala Gln Met Gly Arg Ile Ser Pro Phe Ser Cys Leu Lys Asp
                 20                  25                  30 aga cat gaa ttc aga ttc cca gag gag gag ttt gat ggc aac cag ttc     144
Arg His Glu Phe Arg Phe Pro Glu Glu Glu Phe Asp Gly Asn Gln Phe
             35                  40                  45 cag aag act caa gcc atc tct gtc ctc cat gag atg atc cag cag acc     192
Gln Lys Thr Gln Ala Ile Ser Val Leu His Glu Met Ile Gln Gln Thr
 50                  55                  60 ttc aat ctc ttc agc aca gag gac tca tct gct gct tgg gaa cag agc     240
Phe Asn Leu Phe Ser Thr Glu Asp Ser Ser Ala Ala Trp Glu Gln Ser
 65                  70                  75                  80 ctc cta gaa aaa ttt tcc act gaa ctt tac cag caa ctg aat aac ttg     288
Leu Leu Glu Lys Phe Ser Thr Glu Leu Tyr Gln Gln Leu Asn Asn Leu
                 85                  90                  95 gaa gca tgt gtg ata cag gag gtt ggg gtg gaa gag act ccc ctg atg     336
Glu Ala Cys Val Ile Gln Glu Val Gly Val Glu Glu Thr Pro Leu Met
            100                 105                 110 aat gag gac tcc atc ctg gct gtg agg aaa tac ttc caa aga atc act     384
Asn Glu Asp Ser Ile Leu Ala Val Arg Lys Tyr Phe Gln Arg Ile Thr
        115                 120                 125 ctt tat cta aca gag aag aaa tac agc cct tgt gcc tgg gag gtt gtc     432
Leu Tyr Leu Thr Glu Lys Lys Tyr Ser Pro Cys Ala Trp Glu Val Val
    130                 135                 140 aga gca gaa atc atg aga tcc ctc tcg ttt tca aca aac ttg caa aaa     480
Arg Ala Glu Ile Met Arg Ser Leu Ser Phe Ser Thr Asn Leu Gln Lys
145                 150                 155                 160 aga tta agg agg aag gat tga                                         501
Arg Leu Arg Arg Lys Asp
                165

<210> SEQ ID NO 78
<211> LENGTH: 166
<212> TYPE: PRT
<213> ORGANISM: Homo sapiens

<400> SEQUENCE: 78

Cys Asp Leu Pro Gln Thr His Ser Leu Arg Asn Arg Arg Ala Leu Ile
 1               5                  10                  15

Leu Leu Ala Gln Met Gly Arg Ile Ser Pro Phe Ser Cys Leu Lys Asp
                 20                  25                  30

Arg His Glu Phe Arg Phe Pro Glu Glu Glu Phe Asp Gly Asn Gln Phe
             35                  40                  45

Gln Lys Thr Gln Ala Ile Ser Val Leu His Glu Met Ile Gln Gln Thr
 50                  55                  60

Phe Asn Leu Phe Ser Thr Glu Asp Ser Ser Ala Ala Trp Glu Gln Ser
 65                  70                  75                  80

Leu Leu Glu Lys Phe Ser Thr Glu Leu Tyr Gln Gln Leu Asn Asn Leu
                 85                  90                  95

Glu Ala Cys Val Ile Gln Glu Val Gly Val Glu Glu Thr Pro Leu Met
            100                 105                 110

Asn Glu Asp Ser Ile Leu Ala Val Arg Lys Tyr Phe Gln Arg Ile Thr
        115                 120                 125

Leu Tyr Leu Thr Glu Lys Lys Tyr Ser Pro Cys Ala Trp Glu Val Val
    130                 135                 140
```

```
Arg Ala Glu Ile Met Arg Ser Leu Ser Phe Ser Thr Asn Leu Gln Lys
145                 150                 155                 160

Arg Leu Arg Arg Lys Asp
                165

<210> SEQ ID NO 79
<211> LENGTH: 501
<212> TYPE: DNA
<213> ORGANISM: Homo sapiens
<220> FEATURE:
<221> NAME/KEY: CDS
<222> LOCATION: (1)..(498)

<400> SEQUENCE: 79 tgt gat ctg cct cag acc cac agc ctg ggt aat agg agg gcc ttg ata      48
Cys Asp Leu Pro Gln Thr His Ser Leu Gly Asn Arg Arg Ala Leu Ile
1               5                   10                  15 ctc ctg gca caa atg gga aga atc tct cct ttc tcc tgc ctg aag gac      96
Leu Leu Ala Gln Met Gly Arg Ile Ser Pro Phe Ser Cys Leu Lys Asp
            20                  25                  30 aga cat gac ttt gga ctt ccc cag gag gag ttt gat ggc aac cag ttc     144
Arg His Asp Phe Gly Leu Pro Gln Glu Glu Phe Asp Gly Asn Gln Phe
        35                  40                  45 cag aag act caa gcc atc tct gtc ctc cat gag atg atc cag cag acc     192
Gln Lys Thr Gln Ala Ile Ser Val Leu His Glu Met Ile Gln Gln Thr
    50                  55                  60 ttc aat ctc ttc agc aca aag gat tca tct gct gct tgg gat gag acc     240
Phe Asn Leu Phe Ser Thr Lys Asp Ser Ser Ala Ala Trp Asp Glu Thr
65                  70                  75                  80 ctc cta gac aaa ttc tac att gaa ctt ttc cag caa ctg aat gtc cta     288
Leu Leu Asp Lys Phe Tyr Ile Glu Leu Phe Gln Gln Leu Asn Val Leu
                85                  90                  95 gaa gcc tgt gtg aca cag gag gtt ggg gtg gaa gag att gcc ctg atg     336
Glu Ala Cys Val Thr Gln Glu Val Gly Val Glu Glu Ile Ala Leu Met
            100                 105                 110 aat gag gac tcc atc ctg gct gtg agg aaa tac ttt caa aga atc act     384
Asn Glu Asp Ser Ile Leu Ala Val Arg Lys Tyr Phe Gln Arg Ile Thr
        115                 120                 125 ctt tat ctg atg ggg aag aaa tac agc cct tgt gcc tgg gag gtt gtc     432
Leu Tyr Leu Met Gly Lys Lys Tyr Ser Pro Cys Ala Trp Glu Val Val
    130                 135                 140 aga gca gaa atc atg aga tcc ttc tct ttt tca aca aac ttg caa aaa     480
Arg Ala Glu Ile Met Arg Ser Phe Ser Phe Ser Thr Asn Leu Gln Lys
145                 150                 155                 160 gga tta aga agg aag gat tga                                         501
Gly Leu Arg Arg Lys Asp
                165

<210> SEQ ID NO 80
<211> LENGTH: 166
<212> TYPE: PRT
<213> ORGANISM: Homo sapiens

<400> SEQUENCE: 80

Cys Asp Leu Pro Gln Thr His Ser Leu Gly Asn Arg Arg Ala Leu Ile
1               5                   10                  15

Leu Leu Ala Gln Met Gly Arg Ile Ser Pro Phe Ser Cys Leu Lys Asp
            20                  25                  30

Arg His Asp Phe Gly Leu Pro Gln Glu Glu Phe Asp Gly Asn Gln Phe
        35                  40                  45
```

```
Gln Lys Thr Gln Ala Ile Ser Val Leu His Glu Met Ile Gln Gln Thr
    50                  55                  60

Phe Asn Leu Phe Ser Thr Lys Asp Ser Ser Ala Ala Trp Asp Glu Thr
65                  70                  75                  80

Leu Leu Asp Lys Phe Tyr Ile Glu Leu Phe Gln Gln Leu Asn Val Leu
                85                  90                  95

Glu Ala Cys Val Thr Gln Glu Val Gly Val Glu Glu Ile Ala Leu Met
            100                 105                 110

Asn Glu Asp Ser Ile Leu Ala Val Arg Lys Tyr Phe Gln Arg Ile Thr
        115                 120                 125

Leu Tyr Leu Met Gly Lys Lys Tyr Ser Pro Cys Ala Trp Glu Val Val
    130                 135                 140

Arg Ala Glu Ile Met Arg Ser Phe Ser Phe Ser Thr Asn Leu Gln Lys
145                 150                 155                 160

Gly Leu Arg Arg Lys Asp
                165

<210> SEQ ID NO 81
<211> LENGTH: 501
<212> TYPE: DNA
<213> ORGANISM: Homo sapiens
<220> FEATURE:
<221> NAME/KEY: CDS
<222> LOCATION: (1)..(498)

<400> SEQUENCE: 81 tgt gat ctg cct cag acc cac agc ctg ggt aat agg agg gcc ttg ata      48
Cys Asp Leu Pro Gln Thr His Ser Leu Gly Asn Arg Arg Ala Leu Ile
1               5                   10                  15 ctc ctg gca caa atg gga aga atc tct cat ttc tcc tgc ctg aag gac      96
Leu Leu Ala Gln Met Gly Arg Ile Ser His Phe Ser Cys Leu Lys Asp
                20                  25                  30 aga cat gat ttc gga ttc ccc gag gag gag ttt gat ggc cac cag ttc     144
Arg His Asp Phe Gly Phe Pro Glu Glu Glu Phe Asp Gly His Gln Phe
            35                  40                  45 cag aag gct caa gcc atc tcc gtc ctc cat gag atg atc cag cag acc     192
Gln Lys Ala Gln Ala Ile Ser Val Leu His Glu Met Ile Gln Gln Thr
    50                  55                  60 ttc aat ctc ttc agc aca gag gac tca tct gct gct tgg gaa cag agc     240
Phe Asn Leu Phe Ser Thr Glu Asp Ser Ser Ala Ala Trp Glu Gln Ser
65                  70                  75                  80 ctc cta gaa aaa ttt tcc act gaa ctt tac cag caa ctg aat gac ctg     288
Leu Leu Glu Lys Phe Ser Thr Glu Leu Tyr Gln Gln Leu Asn Asp Leu
                85                  90                  95 gaa gca tgt gtg ata cag gag gtt ggg gtg gaa gag act ccc ctg atg     336
Glu Ala Cys Val Ile Gln Glu Val Gly Val Glu Glu Thr Pro Leu Met
            100                 105                 110 aat gag gac tcc atc ctg gct gtg agg aaa tac ttc caa aga atc act     384
Asn Glu Asp Ser Ile Leu Ala Val Arg Lys Tyr Phe Gln Arg Ile Thr
        115                 120                 125 ctt tat cta aca gag aag aaa tac agc cct tgt gcc tgg gag gtt gtc     432
Leu Tyr Leu Thr Glu Lys Lys Tyr Ser Pro Cys Ala Trp Glu Val Val
    130                 135                 140 aga gca gaa atc atg aga tcc ctc tcg ttt tca aca aac ttg caa aaa     480
Arg Ala Glu Ile Met Arg Ser Leu Ser Phe Ser Thr Asn Leu Gln Lys
145                 150                 155                 160 aga tta agg agg aag gat tga                                          501
Arg Leu Arg Arg Lys Asp
                165
```

<210> SEQ ID NO 82
<211> LENGTH: 166
<212> TYPE: PRT
<213> ORGANISM: Homo sapiens

<400> SEQUENCE: 82

```
Cys Asp Leu Pro Gln Thr His Ser Leu Gly Asn Arg Arg Ala Leu Ile
1               5                   10                  15

Leu Leu Ala Gln Met Gly Arg Ile Ser His Phe Ser Cys Leu Lys Asp
            20                  25                  30

Arg His Asp Phe Gly Phe Pro Glu Glu Glu Phe Asp Gly His Gln Phe
        35                  40                  45

Gln Lys Ala Gln Ala Ile Ser Val Leu His Glu Met Ile Gln Gln Thr
    50                  55                  60

Phe Asn Leu Phe Ser Thr Glu Asp Ser Ser Ala Ala Trp Glu Gln Ser
65                  70                  75                  80

Leu Leu Glu Lys Phe Ser Thr Glu Leu Tyr Gln Gln Leu Asn Asp Leu
                85                  90                  95

Glu Ala Cys Val Ile Gln Glu Val Gly Val Glu Glu Thr Pro Leu Met
            100                 105                 110

Asn Glu Asp Ser Ile Leu Ala Val Arg Lys Tyr Phe Gln Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Leu Ser Phe Ser Thr Asn Leu Gln Lys
145                 150                 155                 160

Arg Leu Arg Arg Lys Asp
                165
```

<210> SEQ ID NO 83
<211> LENGTH: 501
<212> TYPE: DNA
<213> ORGANISM: Homo sapiens
<220> FEATURE:
<221> NAME/KEY: CDS
<222> LOCATION: (1)..(498)

<400> SEQUENCE: 83

```
tgt gat ctg cct cag acc cac agc ctg ggt aat agg agg gcc ttg ata     48
Cys Asp Leu Pro Gln Thr His Ser Leu Gly Asn Arg Arg Ala Leu Ile
1               5                   10                  15 ctc ctg gca caa atg gga aga atc tct cct ttc tcc tgc ctg aag gac     96
Leu Leu Ala Gln Met Gly Arg Ile Ser Pro Phe Ser Cys Leu Lys Asp
            20                  25                  30 aga cat gac ttt gga ttc ccc cag gag gag ttt gat ggc aac cag ttc    144
Arg His Asp Phe Gly Phe Pro Gln Glu Glu Phe Asp Gly Asn Gln Phe
        35                  40                  45 cag aag gct caa gcc atc tct gtc ctc cat gag acg atc cag cag acc    192
Gln Lys Ala Gln Ala Ile Ser Val Leu His Glu Thr Ile Gln Gln Thr
    50                  55                  60 ttc aat ctc ttc agc aca aag gac tct tct gct act tgg gaa cag agc    240
Phe Asn Leu Phe Ser Thr Lys Asp Ser Ser Ala Thr Trp Glu Gln Ser
65                  70                  75                  80 ctc cta gaa aaa ttt tcc act gaa ctt aac cag cag ctg aat gac ctg    288
Leu Leu Glu Lys Phe Ser Thr Glu Leu Asn Gln Gln Leu Asn Asp Leu
                85                  90                  95 gaa gcc tgc gtg ata cag gag gtt ggg gtg gaa gag act ccc ctg atg    336
Glu Ala Cys Val Ile Gln Glu Val Gly Val Glu Glu Thr Pro Leu Met
            100                 105                 110
```

```
aat gtg gac tcc atc ctg gct gtg aag aaa tac ttc caa aga atc act      384
Asn Val Asp Ser Ile Leu Ala Val Lys Lys Tyr Phe Gln Arg Ile Thr
            115                 120                 125 ctt tat ctg aca gag aag aaa tac agc cct tgt gcc tgg gag gtt gtc      432
Leu Tyr Leu Thr Glu Lys Lys Tyr Ser Pro Cys Ala Trp Glu Val Val
130                 135                 140 aga gca gaa atc atg aga tcc ttc tct tta tca aaa att ttt caa gaa      480
Arg Ala Glu Ile Met Arg Ser Phe Ser Leu Ser Lys Ile Phe Gln Glu
145                 150                 155                 160 aga tta agg agg aag gaa tga                                          501
Arg Leu Arg Arg Lys Glu
                165

<210> SEQ ID NO 84
<211> LENGTH: 166
<212> TYPE: PRT
<213> ORGANISM: Homo sapiens

<400> SEQUENCE: 84

Cys Asp Leu Pro Gln Thr His Ser Leu Gly Asn Arg Arg Ala Leu Ile
1               5                   10                  15

Leu Leu Ala Gln Met Gly Arg Ile Ser Pro Phe Ser Cys Leu Lys Asp
            20                  25                  30

Arg His Asp Phe Gly Phe Pro Gln Glu Glu Phe Asp Gly Asn Gln Phe
        35                  40                  45

Gln Lys Ala Gln Ala Ile Ser Val Leu His Glu Thr Ile Gln Gln Thr
    50                  55                  60

Phe Asn Leu Phe Ser Thr Lys Asp Ser Ser Ala Thr Trp Glu Gln Ser
65                  70                  75                  80

Leu Leu Glu Lys Phe Ser Thr Glu Leu Asn Gln Gln Leu Asn Asp Leu
                85                  90                  95

Glu Ala Cys Val Ile Gln Glu Val Gly Val Glu Glu Thr Pro Leu Met
            100                 105                 110

Asn Val Asp Ser Ile Leu Ala Val Lys Lys Tyr Phe Gln Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Leu Ser Lys Ile Phe Gln Glu
145                 150                 155                 160

Arg Leu Arg Arg Lys Glu
                165

<210> SEQ ID NO 85
<211> LENGTH: 501
<212> TYPE: DNA
<213> ORGANISM: Homo sapiens
<220> FEATURE:
<221> NAME/KEY: CDS
<222> LOCATION: (1)..(498)

<400> SEQUENCE: 85 tgt gat ctg cct cag act cac agc ctg ggt aac agg agg gcc ttg ata      48
Cys Asp Leu Pro Gln Thr His Ser Leu Gly Asn Arg Arg Ala Leu Ile
1               5                   10                  15 ctc ctg gca caa atg cga aga atc tct cct ttc tcc tgc ctg aag gac      96
Leu Leu Ala Gln Met Arg Arg Ile Ser Pro Phe Ser Cys Leu Lys Asp
            20                  25                  30 aga cat gac ttt gaa ttc ccc cag gag gag ttt gat gat aaa cag ttc      144
Arg His Asp Phe Glu Phe Pro Gln Glu Glu Phe Asp Asp Lys Gln Phe
```

```
                 35                  40                  45
cag aag gct caa gcc atc tct gtc ctc cat gag atg atc cag cgg acc       192
Gln Lys Ala Gln Ala Ile Ser Val Leu His Glu Met Ile Gln Arg Thr
 50                  55                  60 ttc aac ctc ttc agc aca aag gac tca tct gct gct ttg gat gag acc       240
Phe Asn Leu Phe Ser Thr Lys Asp Ser Ser Ala Ala Leu Asp Glu Thr
 65                  70                  75                  80 ctt cta gat gaa ttc tac atc gaa ctt gac cag cag ctg aat gac ctg       288
Leu Leu Asp Glu Phe Tyr Ile Glu Leu Asp Gln Gln Leu Asn Asp Leu
                     85                  90                  95 gag tcc tgt gtg atg cag gaa gtg ggg gtg aaa gag tct ccc ctg atg       336
Glu Ser Cys Val Met Gln Glu Val Gly Val Lys Glu Ser Pro Leu Met
            100                 105                 110 tac gag gac tcc atc ctg gct gtg agg aaa tac ttc caa aga atc act       384
Tyr Glu Asp Ser Ile Leu Ala Val Arg Lys Tyr Phe Gln Arg Ile Thr
        115                 120                 125 cta tat ctg aca gag aag aaa tac agc tct tgt gcc tgg gag gtt gtc       432
Leu Tyr Leu Thr Glu Lys Lys Tyr Ser Ser Cys Ala Trp Glu Val Val
    130                 135                 140 aga gca gaa atc atg aga tcc ttc tct tta tca atc aac ttg caa aaa       480
Arg Ala Glu Ile Met Arg Ser Phe Ser Leu Ser Ile Asn Leu Gln Lys
145                 150                 155                 160 aga ttg aag agt aag gaa tga                                           501
Arg Leu Lys Ser Lys Glu
                165

<210> SEQ ID NO 86
<211> LENGTH: 166
<212> TYPE: PRT
<213> ORGANISM: Homo sapiens

<400> SEQUENCE: 86

Cys Asp Leu Pro Gln Thr His Ser Leu Gly Asn Arg Arg Ala Leu Ile
  1               5                  10                  15

Leu Leu Ala Gln Met Arg Arg Ile Ser Pro Phe Ser Cys Leu Lys Asp
                 20                  25                  30

Arg His Asp Phe Glu Phe Pro Gln Glu Glu Phe Asp Asp Lys Gln Phe
             35                  40                  45

Gln Lys Ala Gln Ala Ile Ser Val Leu His Glu Met Ile Gln Arg Thr
 50                  55                  60

Phe Asn Leu Phe Ser Thr Lys Asp Ser Ser Ala Ala Leu Asp Glu Thr
 65                  70                  75                  80

Leu Leu Asp Glu Phe Tyr Ile Glu Leu Asp Gln Gln Leu Asn Asp Leu
                     85                  90                  95

Glu Ser Cys Val Met Gln Glu Val Gly Val Lys Glu Ser Pro Leu Met
            100                 105                 110

Tyr Glu Asp Ser Ile Leu Ala Val Arg Lys Tyr Phe Gln Arg Ile Thr
        115                 120                 125

Leu Tyr Leu Thr Glu Lys Lys Tyr Ser Ser Cys Ala Trp Glu Val Val
    130                 135                 140

Arg Ala Glu Ile Met Arg Ser Phe Ser Leu Ser Ile Asn Leu Gln Lys
145                 150                 155                 160

Arg Leu Lys Ser Lys Glu
                165

<210> SEQ ID NO 87
<211> LENGTH: 25
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 87
gcgggcccca atggccytgy ccttt                                           25

<210> SEQ ID NO 88
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
gctctagaay tcatgaaagy gtga                                            24

<210> SEQ ID NO 89
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
gctcagcagc atccrcaaca tc                                              22

<210> SEQ ID NO 90
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
catttccgtg ttgtaccagg tc                                              22

<210> SEQ ID NO 91
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
tcagaaaacc tagaggccg                                                  19

<210> SEQ ID NO 92
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
tggaagaact catgaaagtg tg                                              22

<210> SEQ ID NO 93
<211> LENGTH: 24
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 93
ctcaagtagc ctagcaatat tggc                                              24

<210> SEQ ID NO 94
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
gtattagtca atacagatca tttcc                                             25

<210> SEQ ID NO 95
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
gttacccctc atcaaccagc                                                   20

<210> SEQ ID NO 96
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
gaatcatttc catgatgaac ca                                                22

<210> SEQ ID NO 97
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
ctcttccttc ttggtggccc tg                                                22

<210> SEQ ID NO 98
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
gtgatgagtc agtgagaatc atttc                                             25

<210> SEQ ID NO 99
<211> LENGTH: 19
<212> TYPE: DNA
<213> ORGANISM: Artificial Sequence
<220> FEATURE:
```

-continued

```
<223> OTHER INFORMATION: Description of Artificial Sequence: Synthetic
      primer

<400> SEQUENCE: 99
cttcagagaa cctggagcc                                                      19

<210> SEQ ID NO 100
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
aatcatttcc atgttgaacc ag                                                  22

<210> SEQ ID NO 101
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
agaagcatct gcctgcaata tc                                                  22

<210> SEQ ID NO 102
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
gctatgacca tgattacgaa ttc                                                 23
```